US012403104B2

(12) United States Patent
Tesar et al.

(10) Patent No.: US 12,403,104 B2
(45) Date of Patent: Sep. 2, 2025

(54) COMPOUNDS AND METHODS OF PROMOTING MYELINATION

(71) Applicant: Case Western Reserve University, Cleveland, OH (US)

(72) Inventors: Paul J. Tesar, Wickliffe, OH (US); Drew Adams, Cleveland, OH (US); Zita Hubler, Cleveland, OH (US); Matthew Elitt, St. Louis, MO (US); Dharmaraja Allimuthu, Cleveland, OH (US); Steven B. Landau, Wellesley, MA (US)

(73) Assignee: Case Western Reserve University, Cleveland, OH (US)

( * ) Notice: Subject to any disclaimer, the term of this patent is extended or adjusted under 35 U.S.C. 154(b) by 324 days.

(21) Appl. No.: 17/826,252

(22) Filed: May 27, 2022

(65) Prior Publication Data
US 2023/0000798 A1 Jan. 5, 2023

Related U.S. Application Data

(62) Division of application No. 16/320,554, filed as application No. PCT/US2017/044205 on Jul. 27, 2017, now Pat. No. 11,344,511.

(60) Provisional application No. 62/452,204, filed on Jan. 30, 2017, provisional application No. 62/367,416, filed on Jul. 27, 2016.

(51) Int. Cl.
| A61K 31/137 | (2006.01) |
| A61K 31/136 | (2006.01) |
| A61K 31/138 | (2006.01) |
| A61K 31/198 | (2006.01) |
| A61K 31/4174 | (2006.01) |
| A61K 31/4196 | (2006.01) |
| A61K 31/4535 | (2006.01) |
| A61K 31/4545 | (2006.01) |
| A61K 31/496 | (2006.01) |
| A61K 31/5375 | (2006.01) |
| A61K 31/7105 | (2006.01) |
| A61K 38/16 | (2006.01) |
| A61K 38/21 | (2006.01) |
| A61K 39/395 | (2006.01) |
| A61K 45/06 | (2006.01) |
| A61P 25/14 | (2006.01) |
| A61P 25/28 | (2006.01) |
| C12N 9/50 | (2006.01) |
| C12N 15/113 | (2010.01) |

(52) U.S. Cl.
CPC .......... *A61K 31/137* (2013.01); *A61K 31/136* (2013.01); *A61K 31/138* (2013.01); *A61K 31/198* (2013.01); *A61K 31/4174* (2013.01); *A61K 31/4196* (2013.01); *A61K 31/4535* (2013.01); *A61K 31/4545* (2013.01); *A61K 31/496* (2013.01); *A61K 31/5375* (2013.01); *A61K 31/7105* (2013.01); *A61K 38/16* (2013.01); *A61K 38/215* (2013.01); *A61K 39/3955* (2013.01); *A61K 45/06* (2013.01); *A61P 25/14* (2018.01); *A61P 25/28* (2018.01); *C12N 9/50* (2013.01); *C12N 15/1137* (2013.01)

(58) Field of Classification Search
CPC ....... A61P 25/28; A61K 39/3955; C12N 9/30; C12N 15/1137; C12N 19/34
USPC ............... 435/6.1, 91.1, 91.31, 455, 458; 514/44 A; 530/350; 536/23.1, 24.5
See application file for complete search history.

(56) References Cited

U.S. PATENT DOCUMENTS

| 5,354,781 A | 10/1994 | Breliere et al. |
| 6,482,986 B1 | 11/2002 | Boigegrain et al. |
| 10,918,610 B2 | 2/2021 | Tesar et al. |
| 11,344,511 B2 | 5/2022 | Tesar et al. |
| 2007/0123556 A1 | 5/2007 | Pennypacker et al. |
| 2008/0089861 A1 | 4/2008 | Went et al. |
| 2010/0009970 A1 | 1/2010 | Johansen et al. |
| 2010/0092479 A1 | 4/2010 | Johansen et al. |
| 2010/0183613 A1* | 7/2010 | Borawski ................ A61P 31/14 514/452 |
| 2010/0298394 A1 | 11/2010 | Steiner et al. |
| 2015/0232444 A1 | 8/2015 | De Brabander et al. |
| 2016/0015707 A1 | 1/2016 | Tesar et al. |
| 2016/0313302 A1 | 10/2016 | DeBrabander et al. |
| 2018/0228743 A1 | 8/2018 | Tesar et al. |

FOREIGN PATENT DOCUMENTS

| EP | 0376850 A1 | 7/1990 | |
| WO | 2000/25767 A2 | 5/2000 | |
| WO | WO-0025767 A2 * | 5/2000 | .......... A61K 31/138 |
| WO | 2008/021970 A2 | 2/2008 | |
| WO | 2008/124131 A1 | 10/2008 | |

(Continued)

OTHER PUBLICATIONS

U.S. Appl. No. 15/880,184, filed Jan. 25, 2018, 2018/0228743, Abandoned.

(Continued)

*Primary Examiner* — Jane J Zara
(74) *Attorney, Agent, or Firm* — McCarter & English, LLP; Yu Lu

(57) ABSTRACT

A method of promoting the generation of oligodendrocytes from oligodendrocyte precursor cells by enhancing their survival and/or maturation includes administering to the cell an effective amount of an agent that enhances and/or induces accumulation of Δ8,9-unsaturated sterol intermediates of the cholesterol biosynthesis pathway in the oligodendrocyte precursor cells.

10 Claims, 47 Drawing Sheets

(56) References Cited

FOREIGN PATENT DOCUMENTS

| | | |
|---|---|---|
| WO | 2010/021681 A2 | 2/2010 |
| WO | 2015/088625 A2 | 6/2015 |
| WO | 2018/022904 A2 | 2/2018 |

OTHER PUBLICATIONS

U.S. Appl. No. 16/320,554, filed Jan. 25, 2019, U.S. Pat. No. 11,344,511, Granted.

U.S. Appl. No. 16/229,875, filed Dec. 21, 2018, U.S. Pat. No. 10,918,610, Granted.

Allimuthu et al., Diverse Chemical Scaffolds Enhance Oligodendrocyte Formation by Inhibiting CYP51, TM7SF2, or EBP. Cell Chem Biol. Apr. 18, 2019;26(4):593-599.

Bourrie et al., Enhancement of endotoxin-induced interleukin-10 production by SR 31747A, a sigma ligand. Eur J Immunol. Oct. 1995;25(10):2882-7.

Bourrie et al., SSR125329A, a high affinity sigma receptor ligand with potent anti-inflammatory properties. Eur J Pharmacol. Dec. 5, 2002;456(1-3):123-31.

Bradl et al., Oligodendrocytes: biology and pathology. Acta Neuropathol. Jan. 2010;119(1):37-53.

Casellas et al., Immunopharmacological profile of SR 31747: in vitro and in vivo studies on humoral and cellular responses. J Neuroimmunol. Jul. 1994;52(2):193-203.

Chao et al., Increased Hippocampal Myelin Content in Veterans with Posttraumatic Stress Disorder. Front Behav Neurosci. Dec. 2, 2015;9:333. 8 pages.

Chao et al., Preliminary Evidence of Increased Hippocampal Myelin Content in Veterans with Posttraumatic Stress Disorder. Front Behav Neurosci. Dec. 2, 2015;9:333. 8 pages.

Ekins et al., Three-dimensional quantitative structure-activity relationship analysis of human CYP51 inhibitors. Drug Metab Dispos. Mar. 2007;35(3):493-500.

Genetics Home Reference, Metachromatic leukodystrophy. Retrieved online at: https://ghr.nlm.nih.gov/condition/metachromatic-leukodystrophy, 6 pages, Feb. 2013.

Google.com, relieve. 1 page, accessed Oct. 9, 2018.

Guggenberger et al., Functional analysis of cholesterol biosynthesis by RNA interference. J Steroid Biochem Mol Biol. May 2007;104(3-5):105-9.

Harlow et al., Remyelination Therapy in Multiple Sclerosis. Front Neurol. Dec. 1, 2015;6:257, 13 pages.

Hubler et al., Accumulation of 8,9-unsaturated sterols drives oligodendrocyte formation and remyelination. Nature. Aug. 2018;560(7718):372-376.

Labit-Le Bouteiller et al., Antiproliferative effects of SR31747A in animal cell lines are mediated by inhibition of cholesterol biosynthesis at the sterol isomerase step. Eur J Biochem. Sep. 1, 1998;256(2):342-9.

Paul et al., Allosteric modulation of peripheral sigma binding sites by a new selective ligand: SR 31747. J Neuroimmunol. Jul. 1994;52(2):183-92.

Rankin et al., Selective Estrogen Receptor Modulators Enhance CNS Remyelination Independent of Estrogen Receptors. J Neurosci. Mar. 20, 2019;39(12):2184-2194.

Reitz, Toward precision medicine in Alzheimer's disease. Ann Transl Med. Mar. 2016;4(6):107. 7 pages.

Stanford Health Now, Alzheimer's Prevention, Treatment and Research—A Q&A with Dr. Frank Longo. Retrieved online at: https://stanfordhealthcare.org/stanford-health-now/2016/alzheimers-prevention-treatment-research-qa-longo.html, 2 pages, Jan. 29, 2016.

Stankiewicz et al., Role of immunosuppressive therapy for the treatment of multiple sclerosis. Neurotherapeutics. Jan. 2013;10(1):77-88.

Stanley, Myelin and multiple sclerosis. Lipid Technology. Mar. 4, 2011;23(3):64-66.

Wang et al., Reducing CYP51 inhibits follicle-stimulating hormone induced resumption of mouse oocyte meiosis in vitro. J Lipid Res. Nov. 2009;50(11):2164-72.

Xu et al., Silencing of mouse hepatic lanosterol 14-alpha demethylase down-regulated plasma low-density lipoprotein cholesterol levels by short-term treatment of siRNA. Biol Pharm Bull. Jun. 2008;31(6):1182-91.

Supplementary European Search Report for Application No. 17835280.3, dated Mar. 17, 2020, 11 pages.

Saher et al., High cholesterol level is essential for myelin membrane growth. Nat Neurosci. Apr. 2005;8(4):468-75.

Zhao et al., Dual regulatory switch through interactions of Tcf7l2/Tcf4 with stage-specific partners propels oligodendroglial maturation. Nat Commun. Mar. 9, 2016;7:10883, 15 pages.

Hayashi et al., Lipid metabolism in the central nervous system and neurodegenerative diseases]. Nihon Yakurigaku Zasshi. Jun. 2011;137(6):227-31.

Yamauchi, Signaling mechanism underlying myelination in peripheral nervous system. Seikagaku. Jul. 2009;81 (7):565-80.

\* cited by examiner

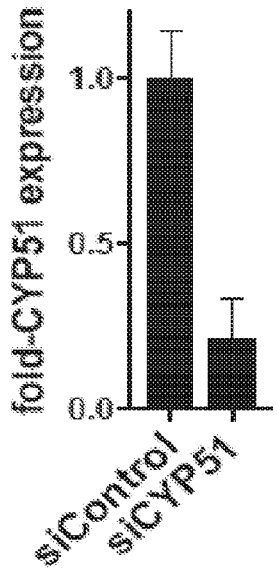
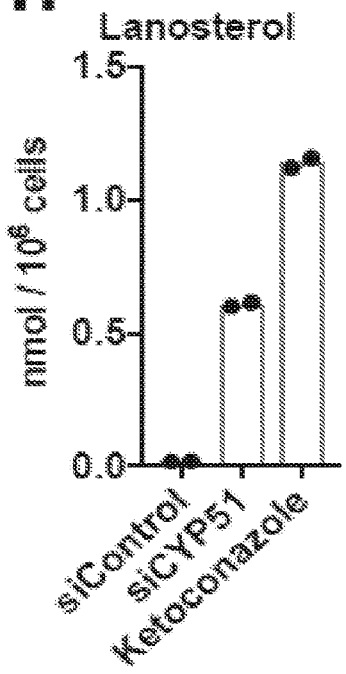
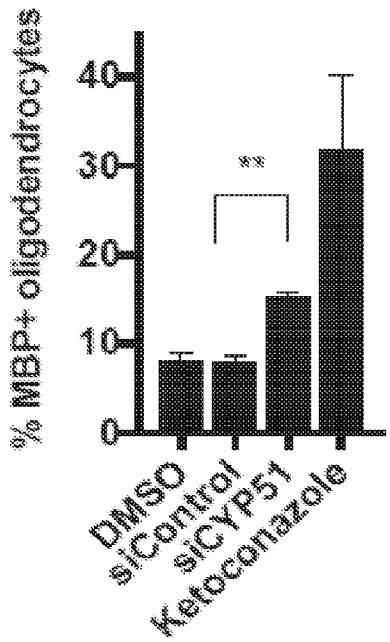
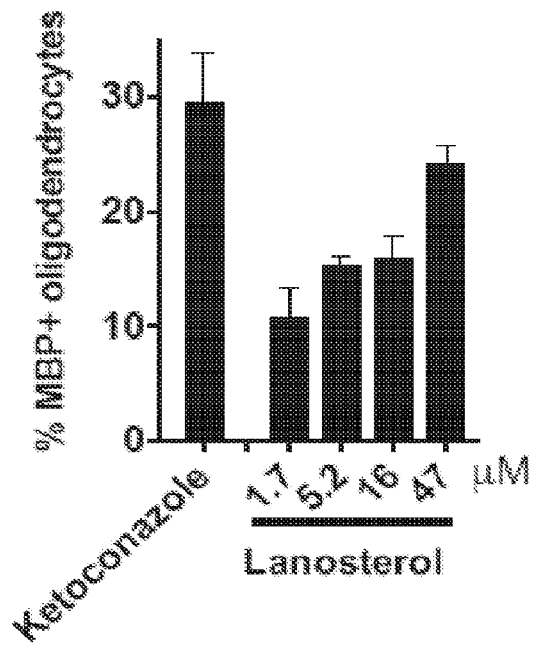
Figs. 1G-J

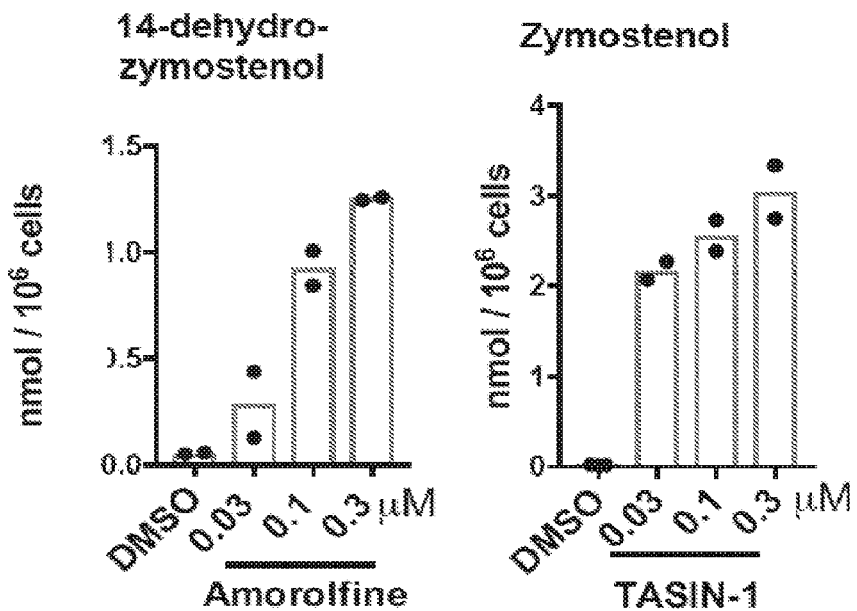
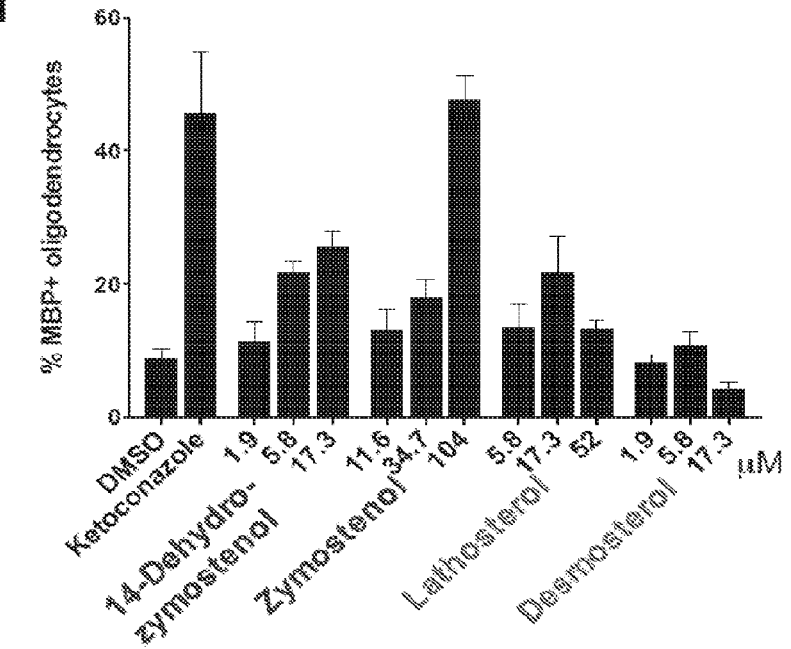
Fig. 2C-D

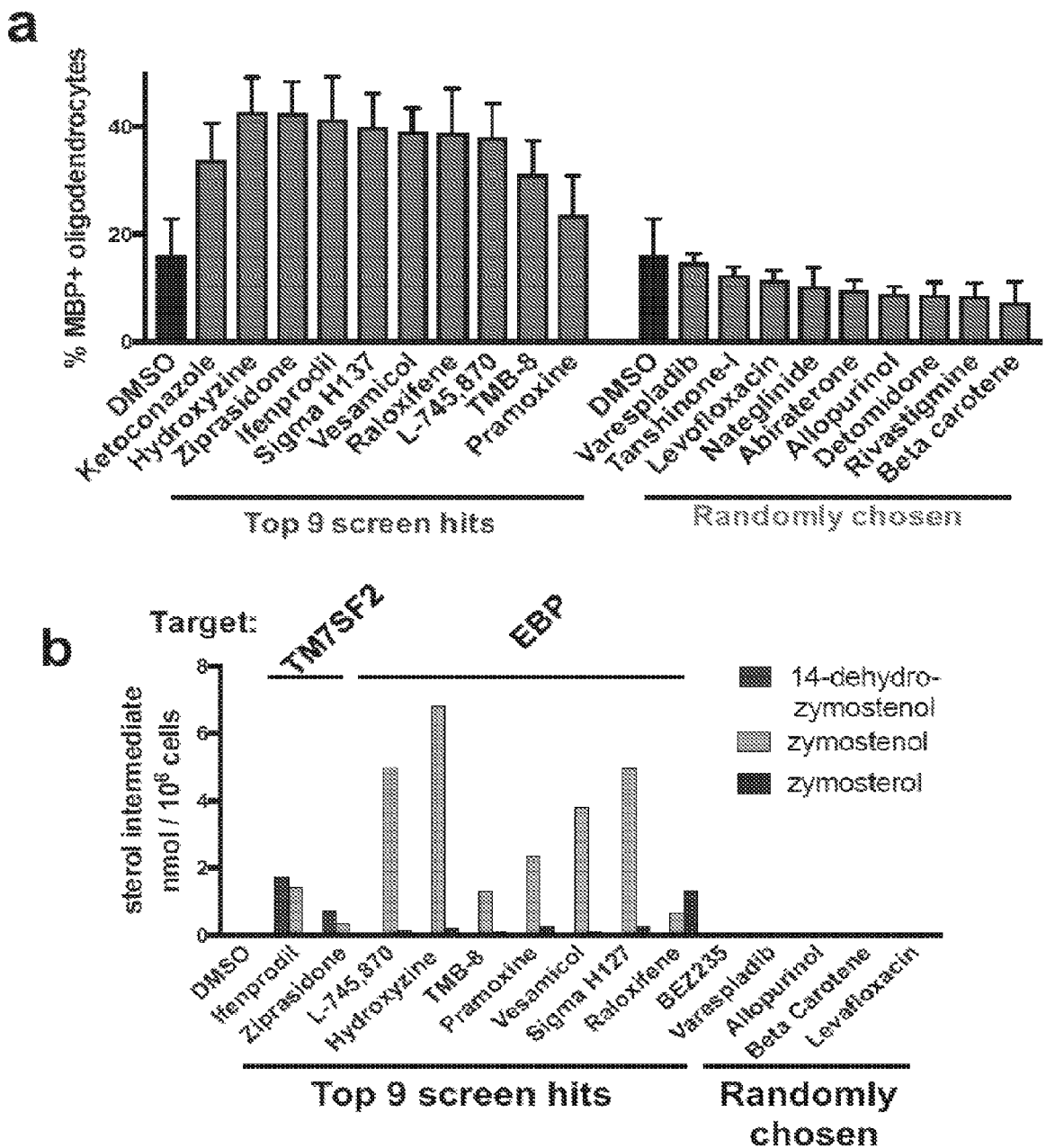
Figs. 3A-B

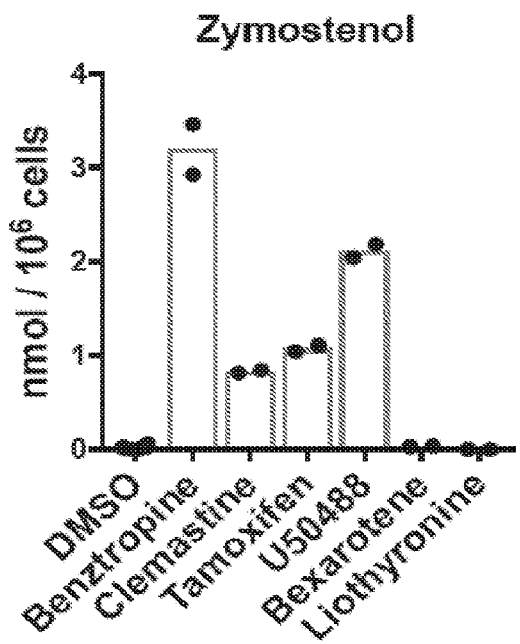
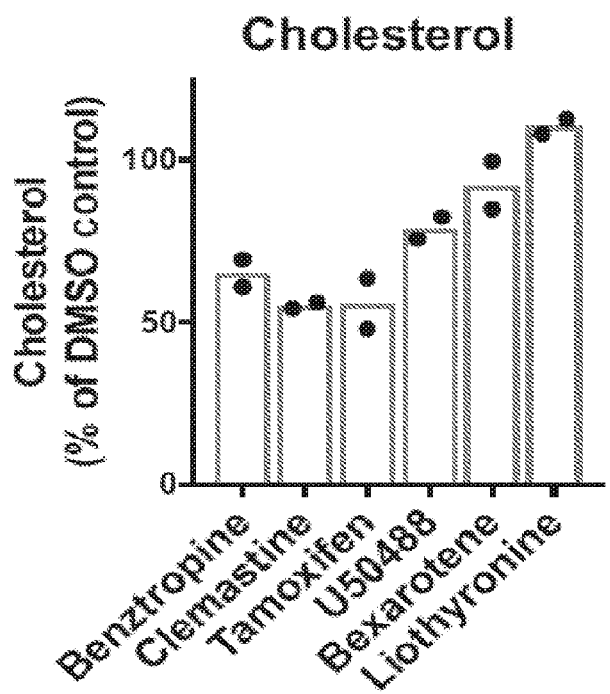
Figs. 3C-D

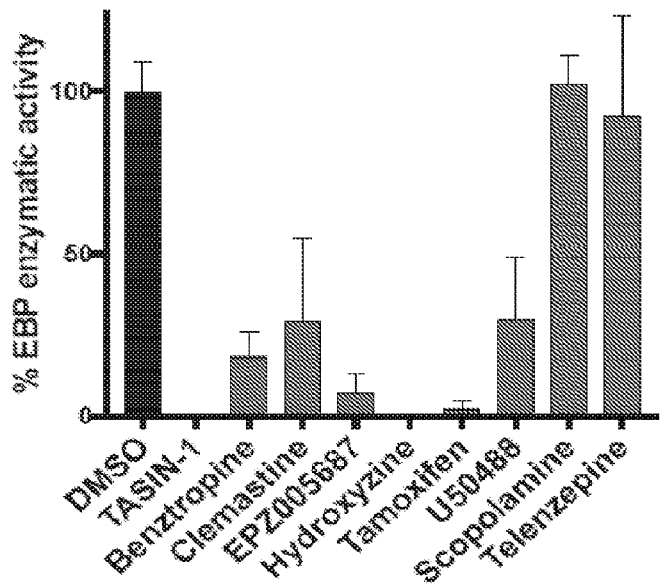
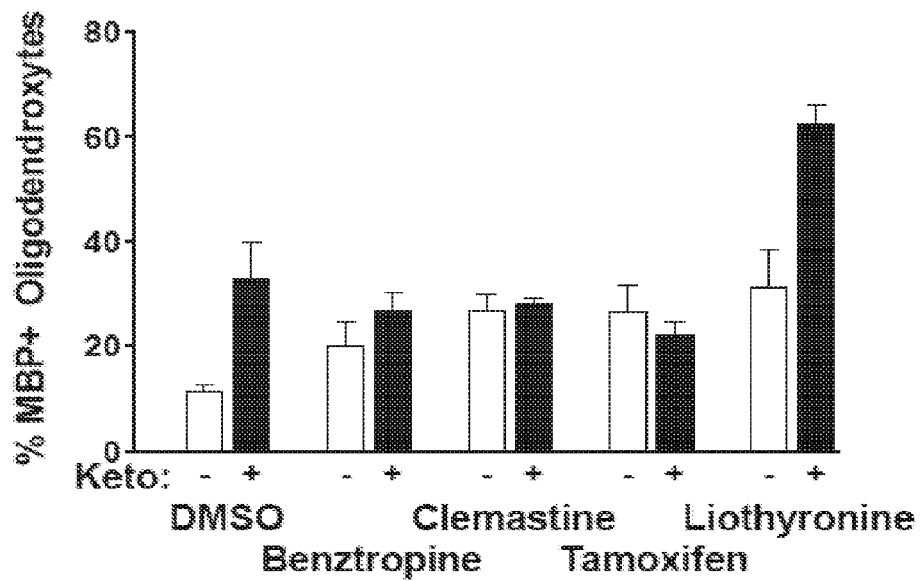
Figs. 3E-F

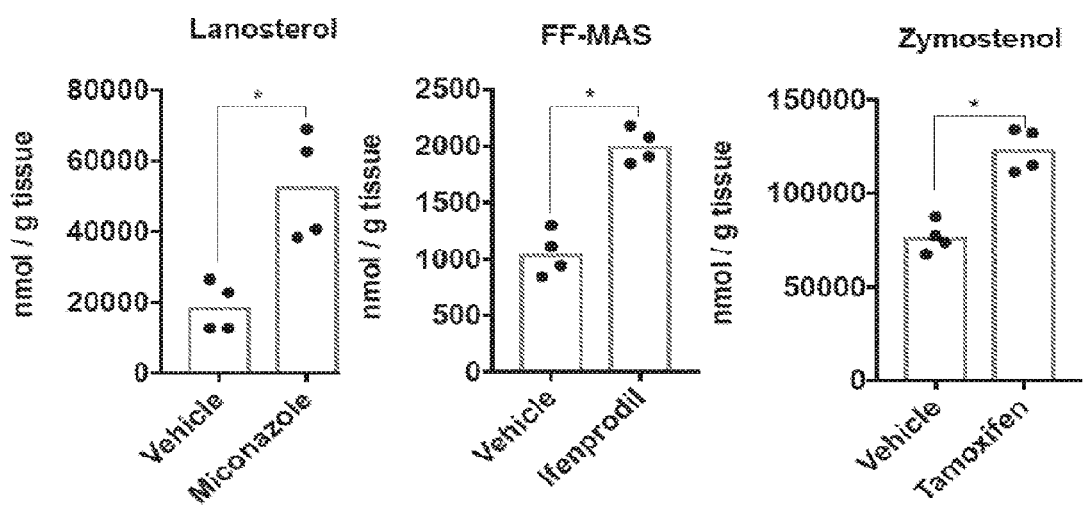
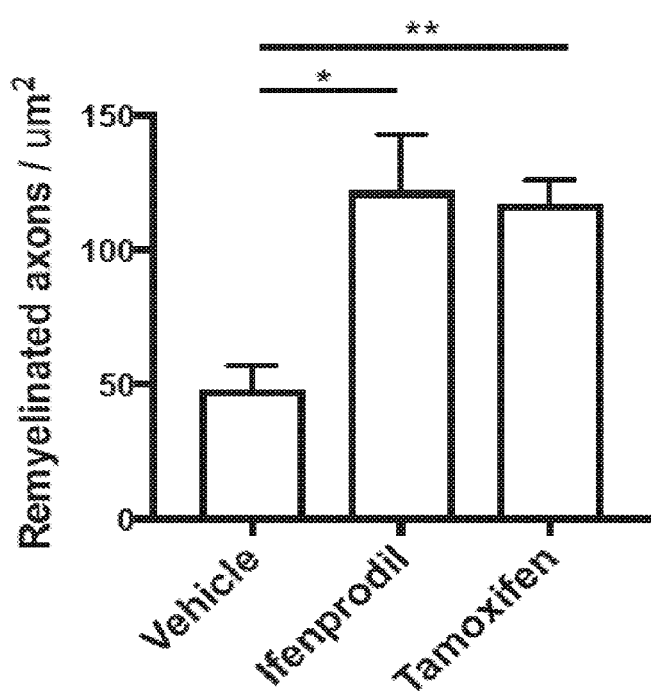
Figs. 4A-B c d

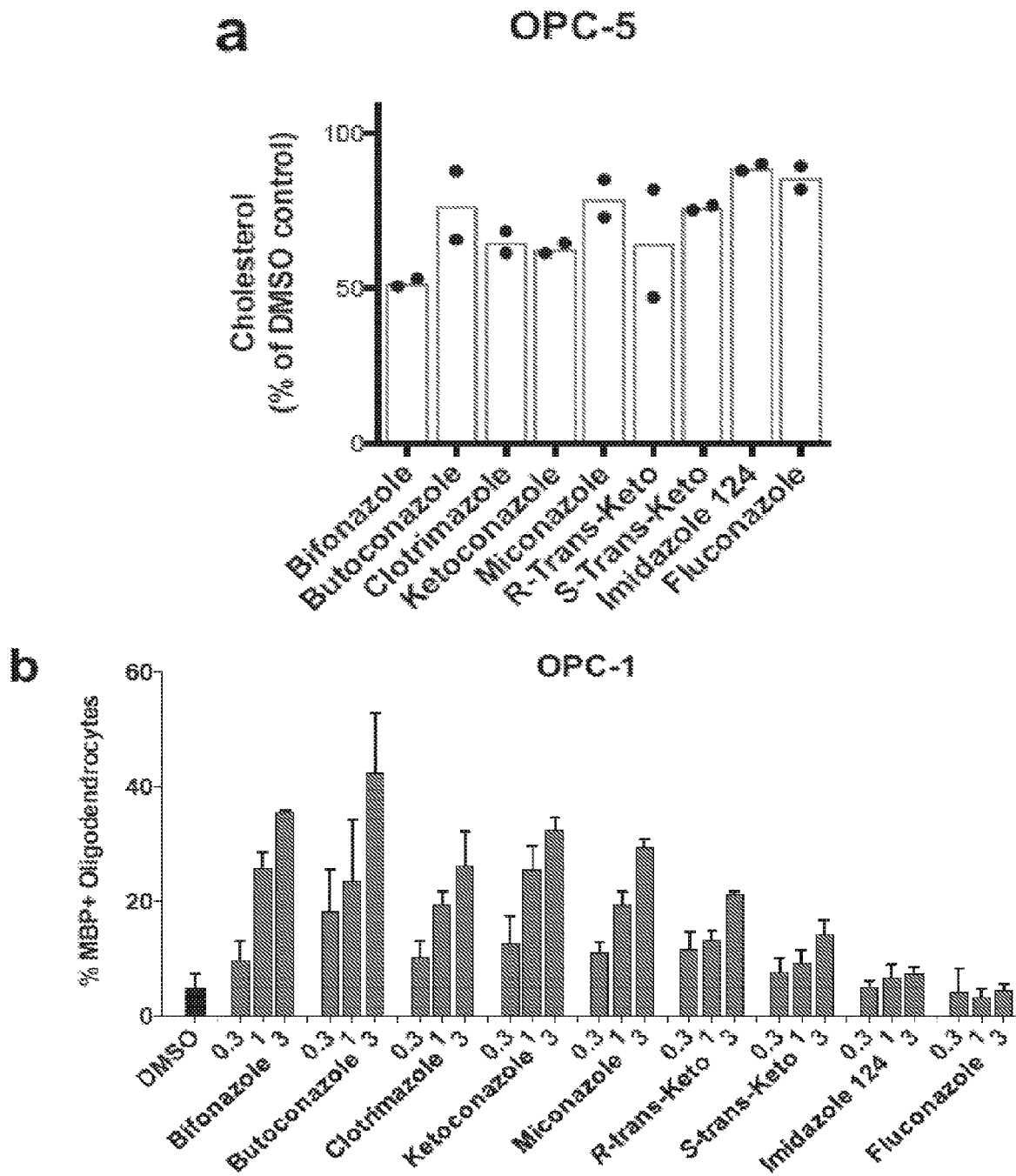
Figs. 5A-B

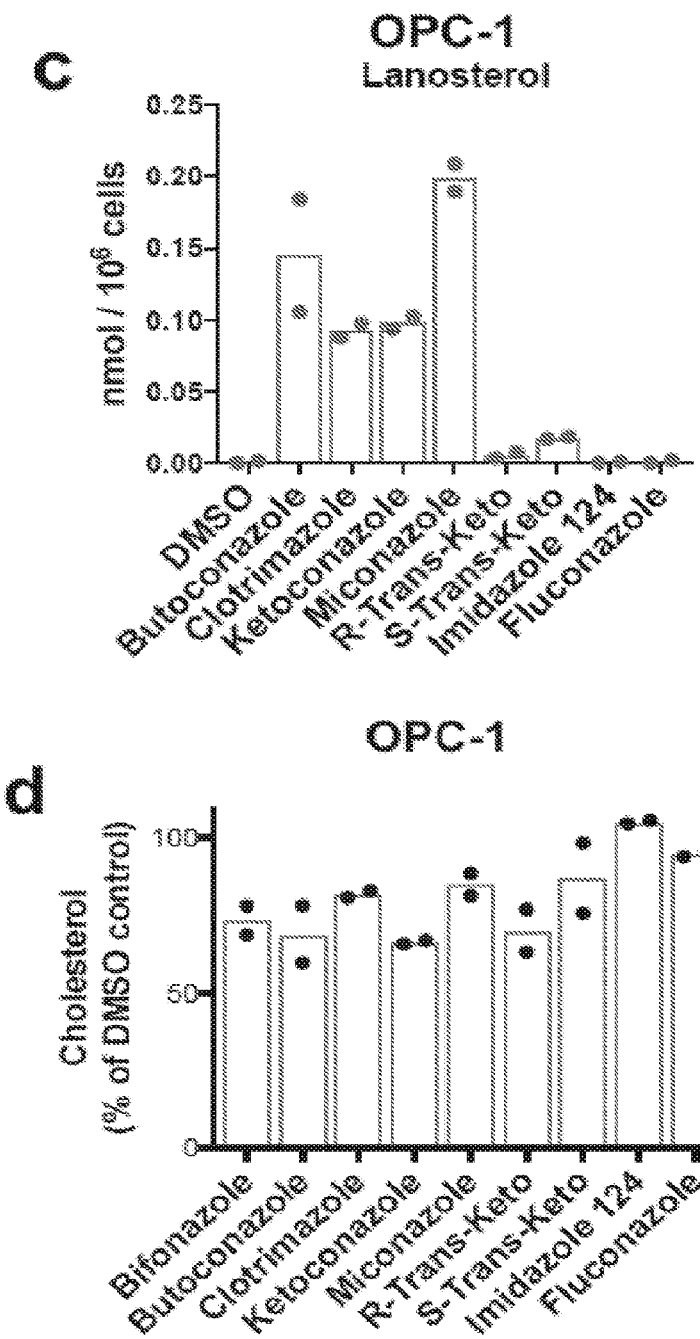
Figs. 5C-D

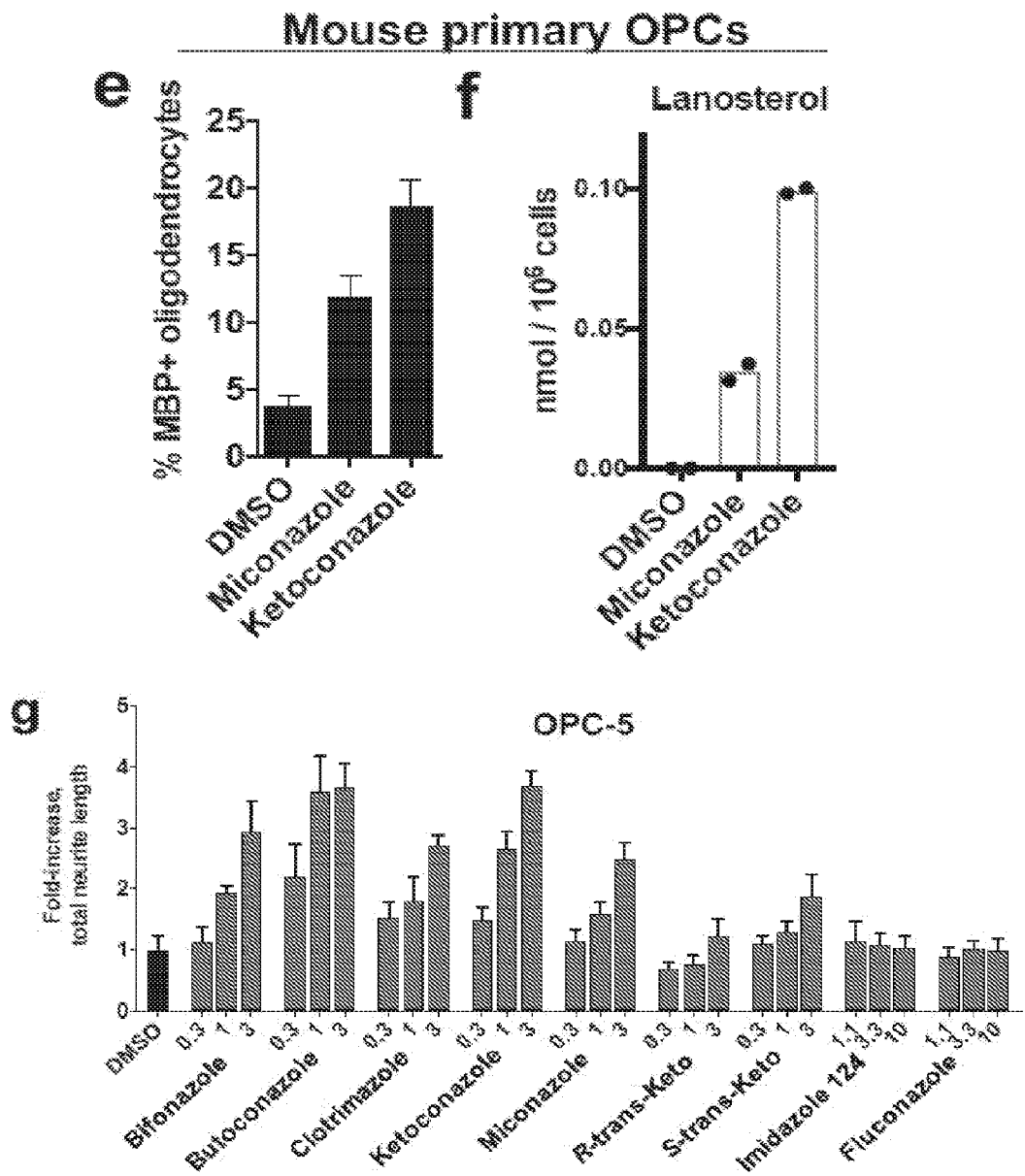
Figs. 5E-G

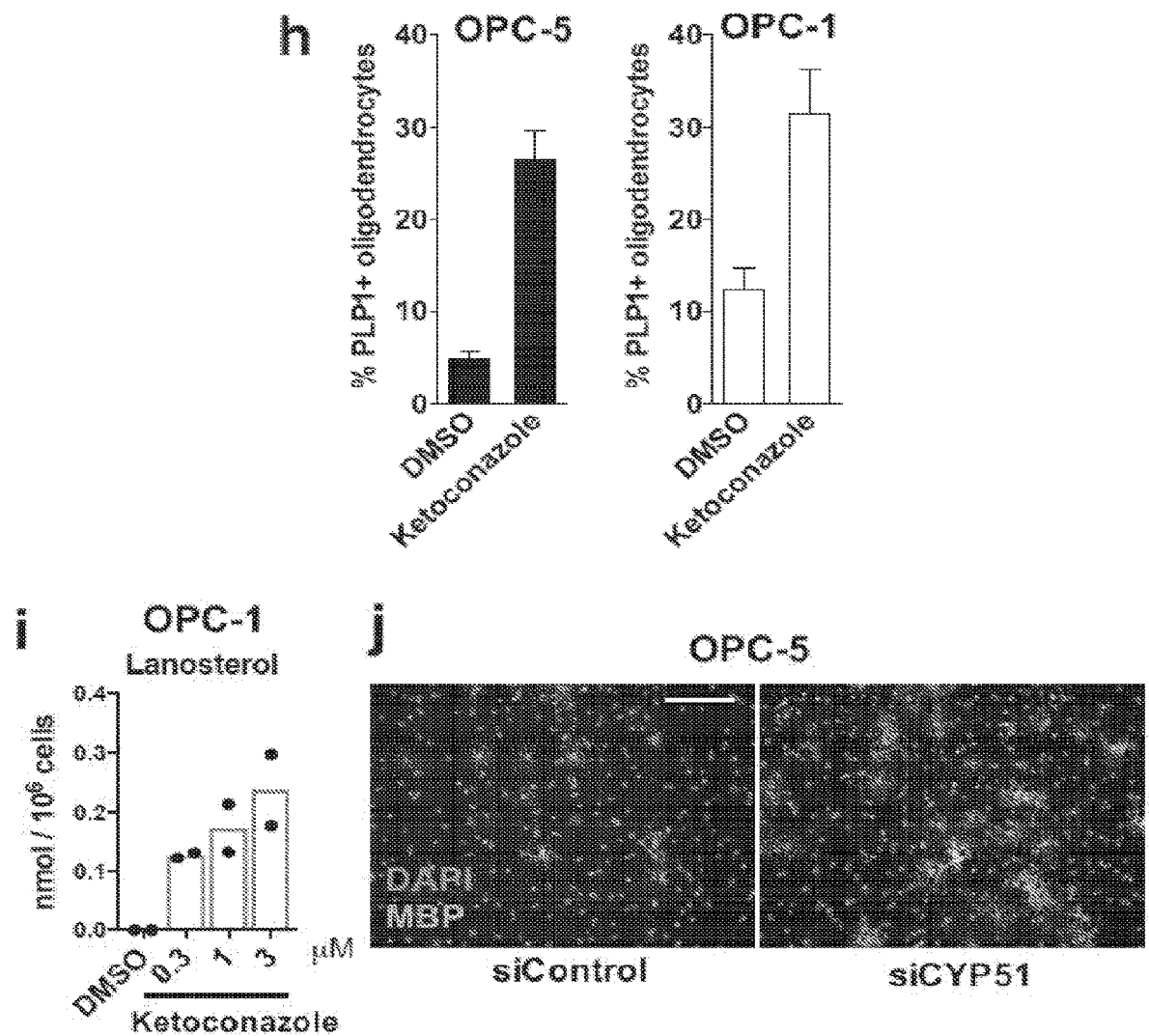
Figs. 5H-J

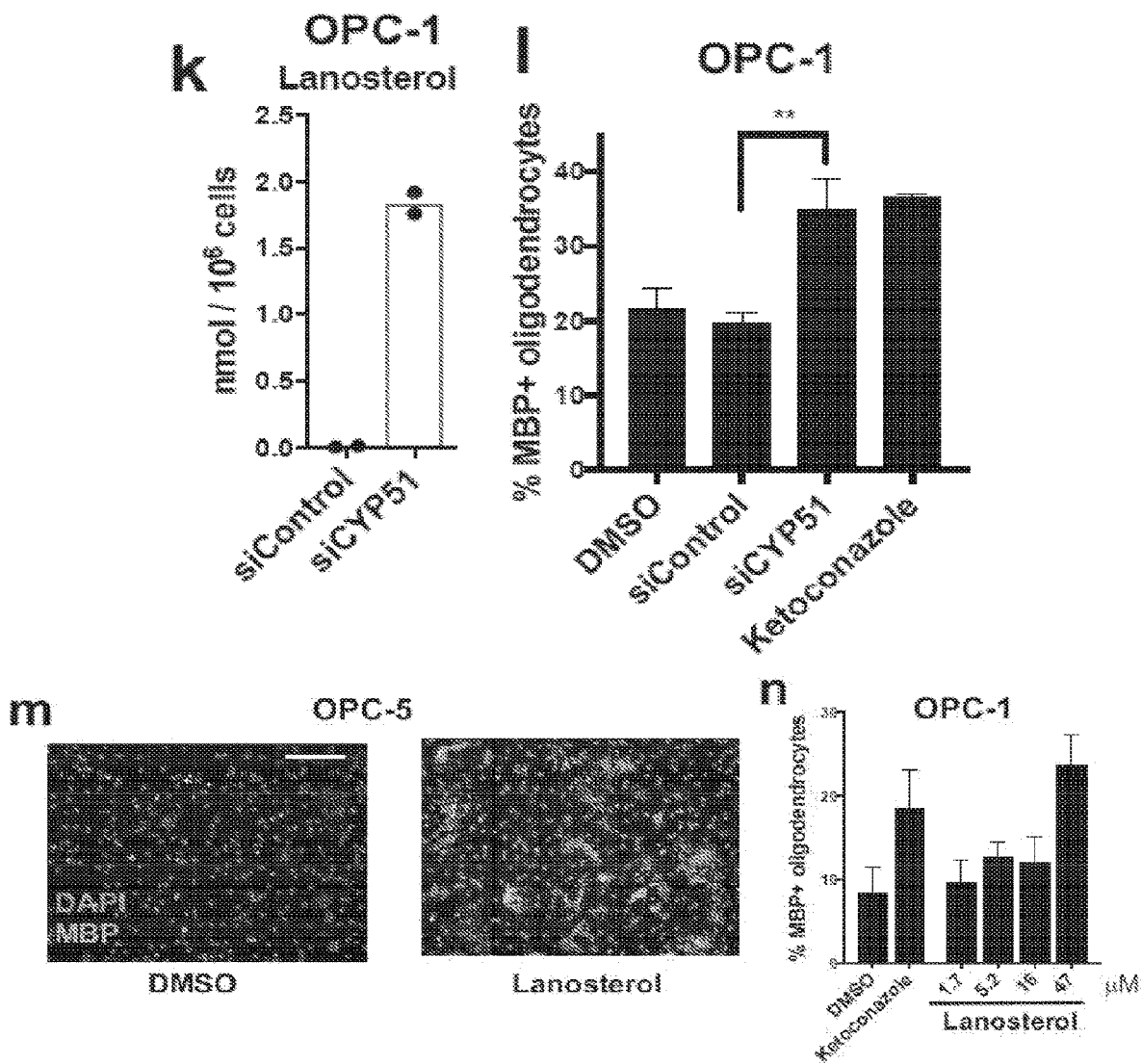
Figs. 5K-N

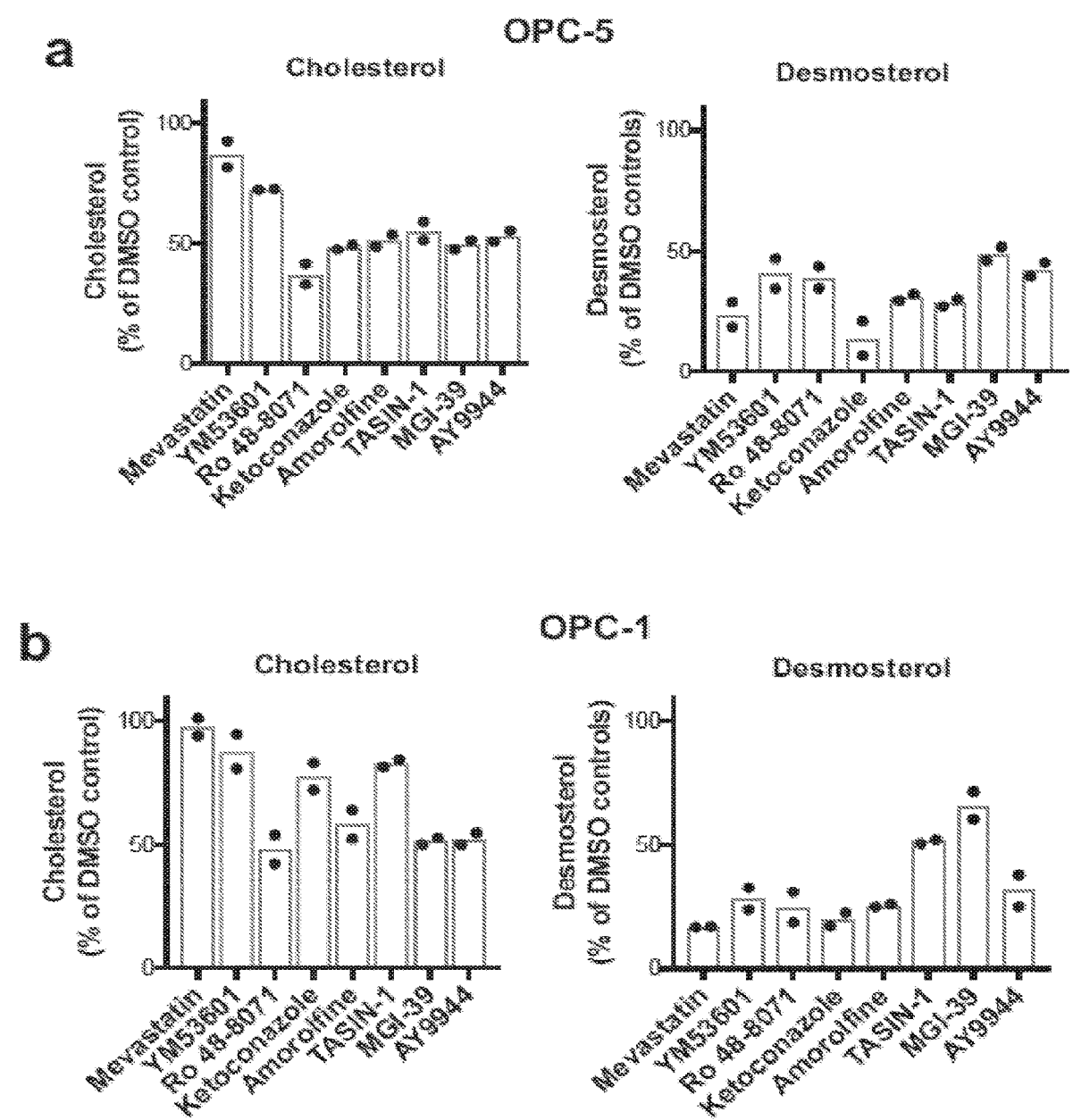
Figs. 7A-B

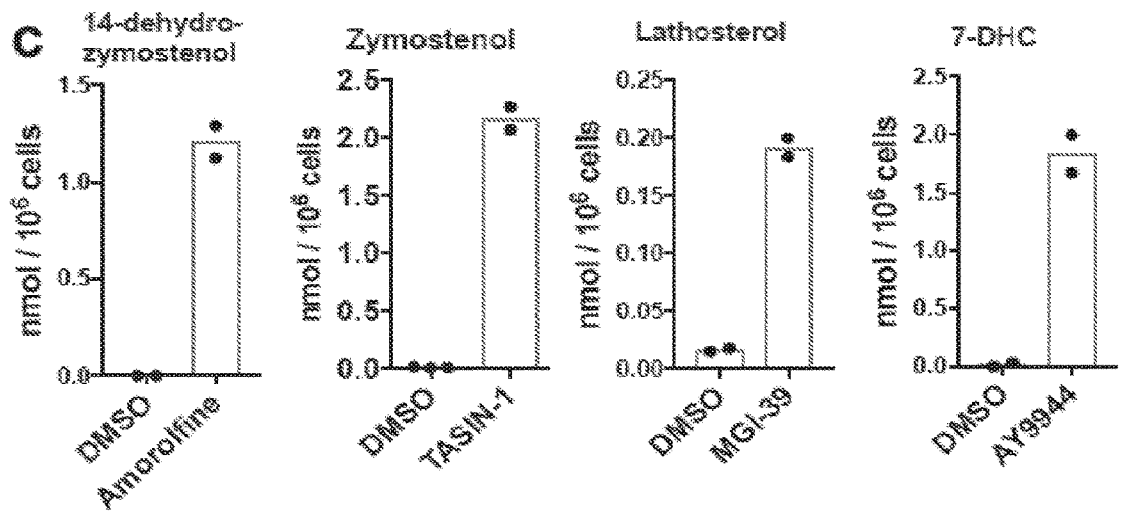
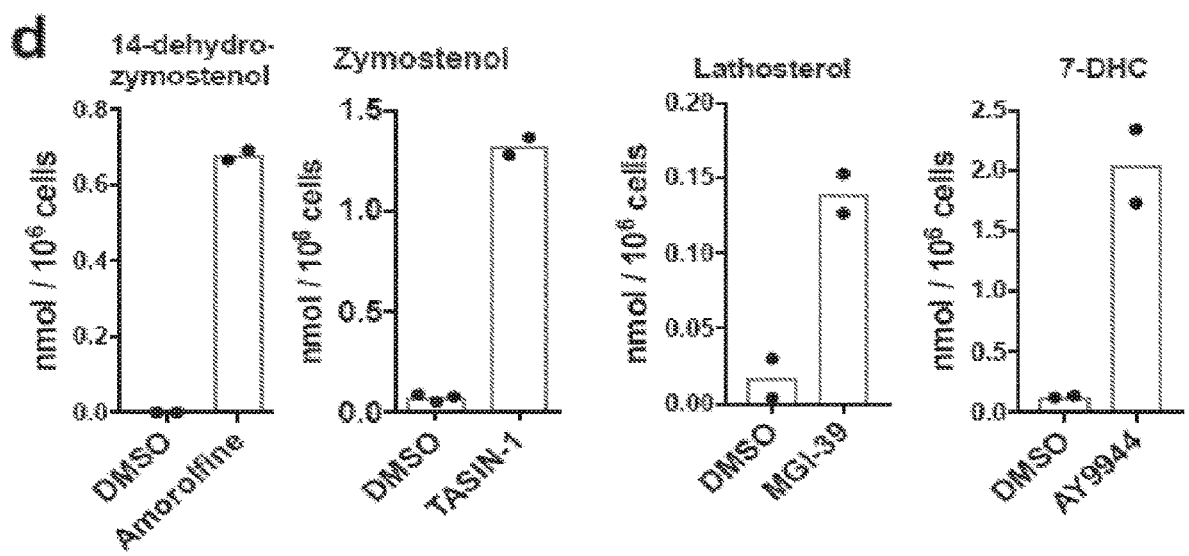
Figs. 7C-D

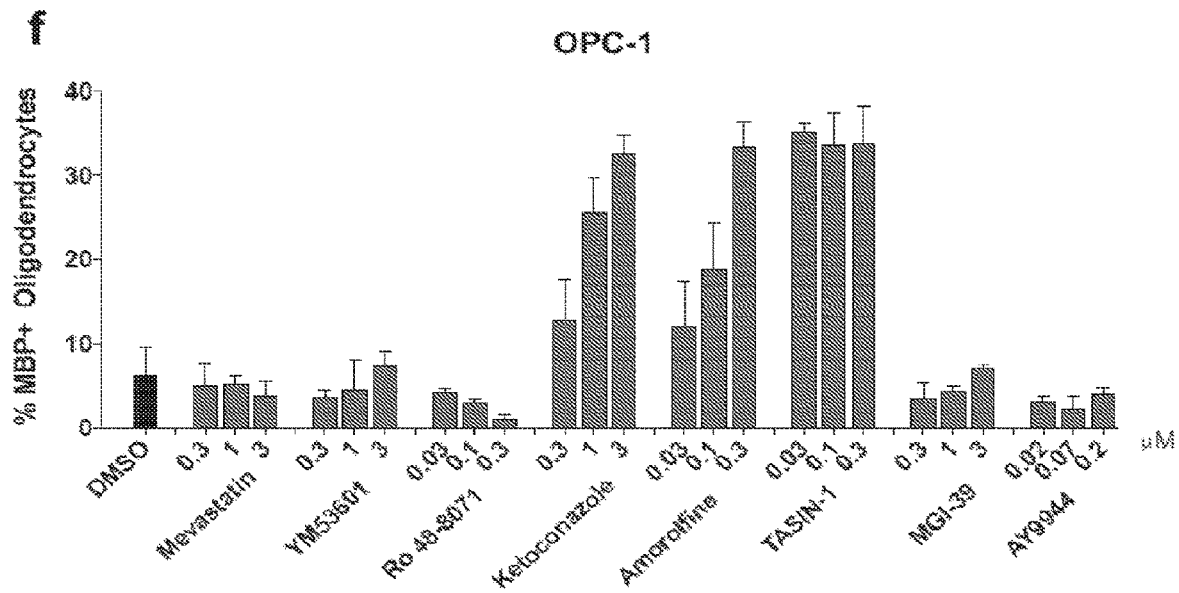
Fig. 7F
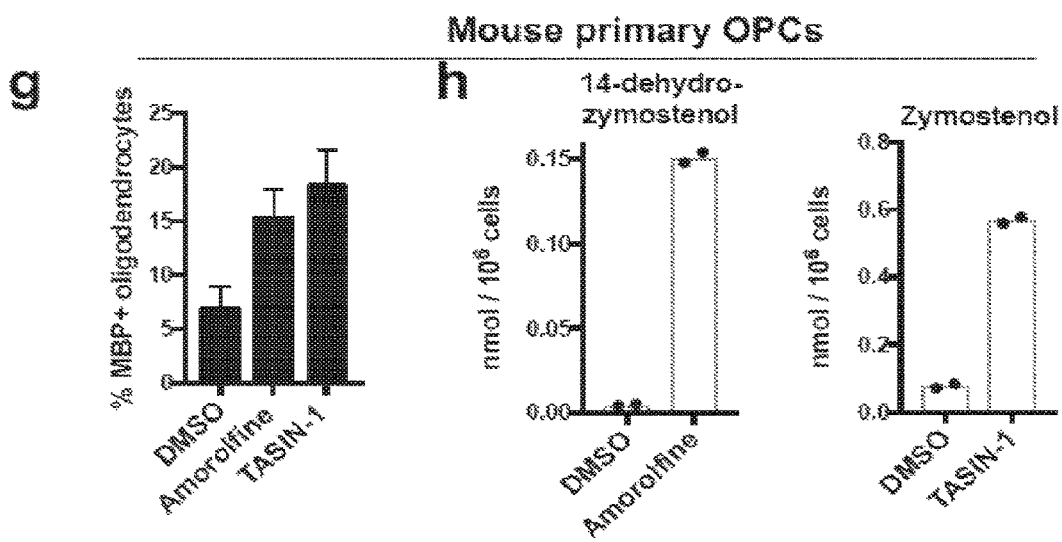
Figs. 7G-H

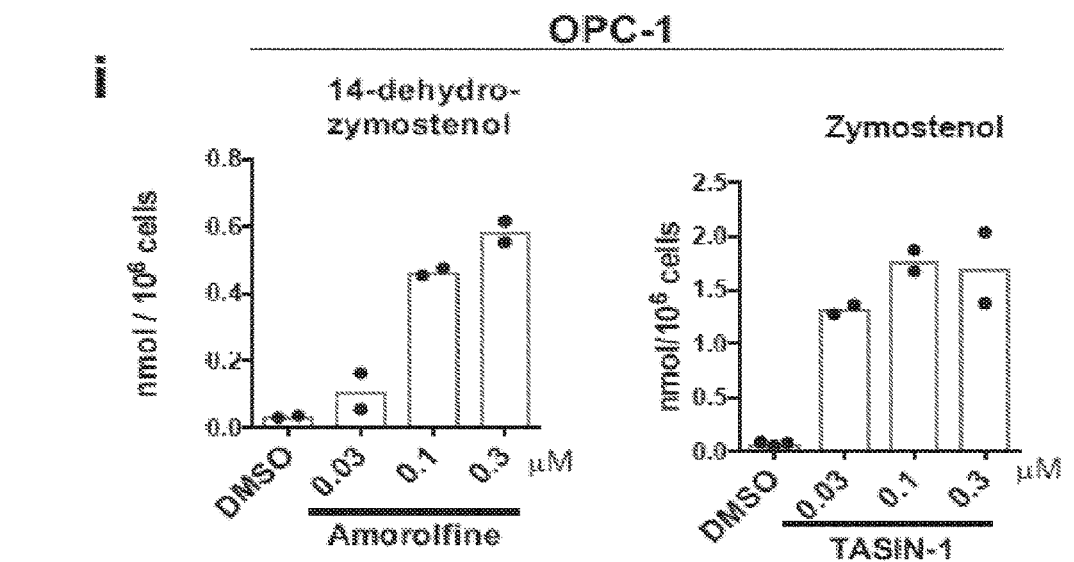
Fig. 7I
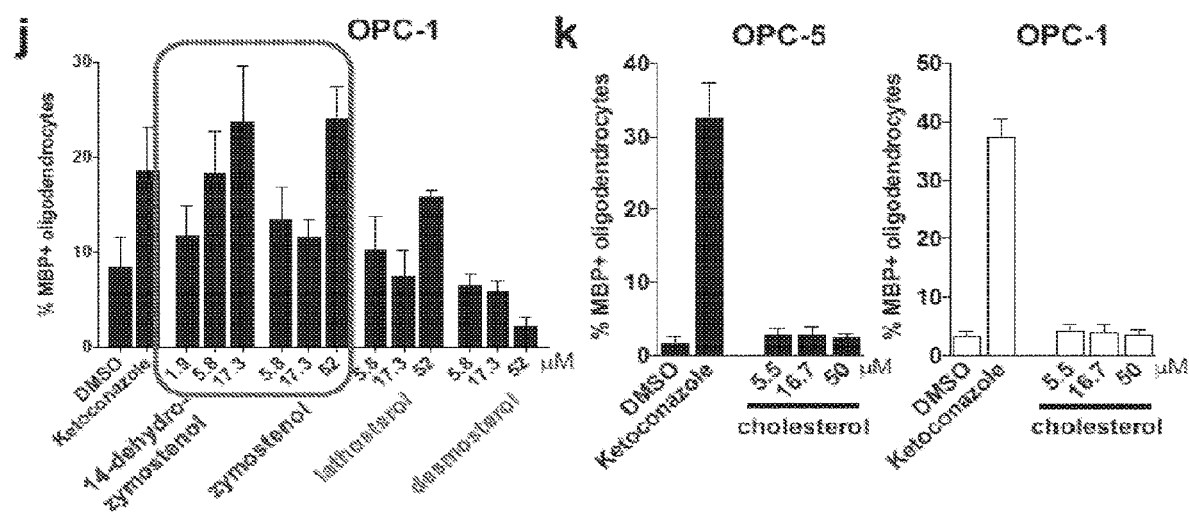
Figs. 7J-K

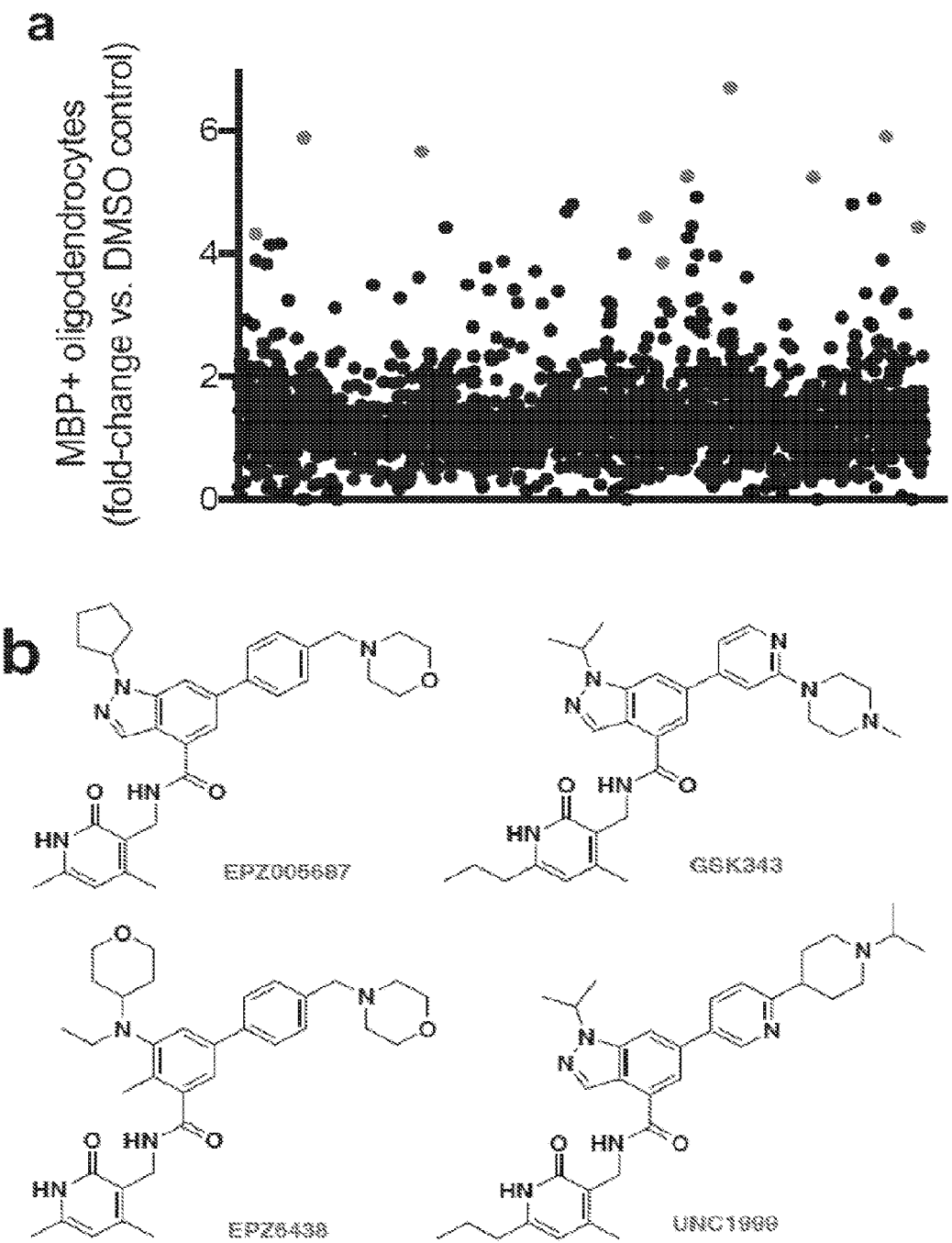
Figs. 8A-B

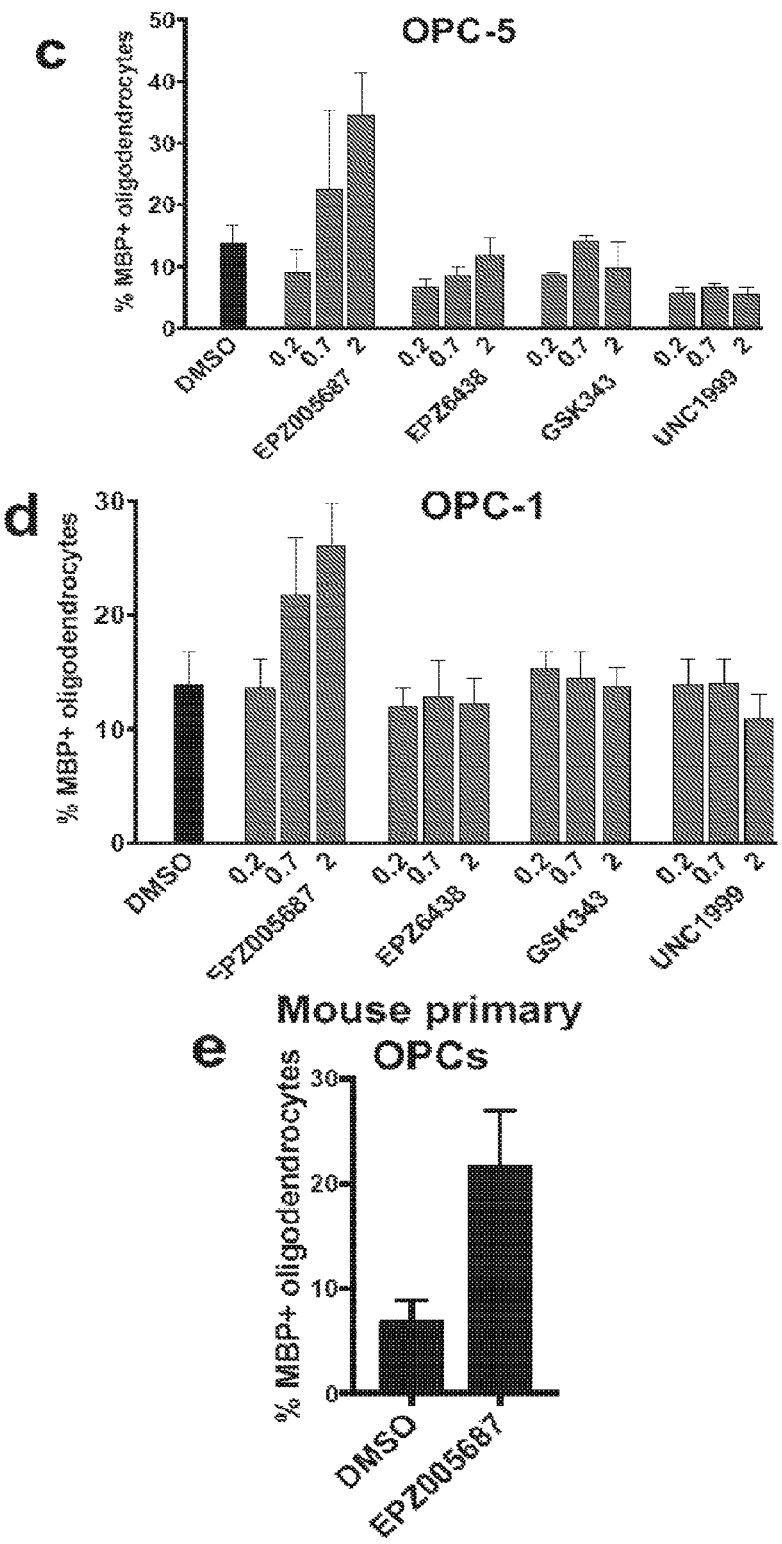
Figs. 8C-E

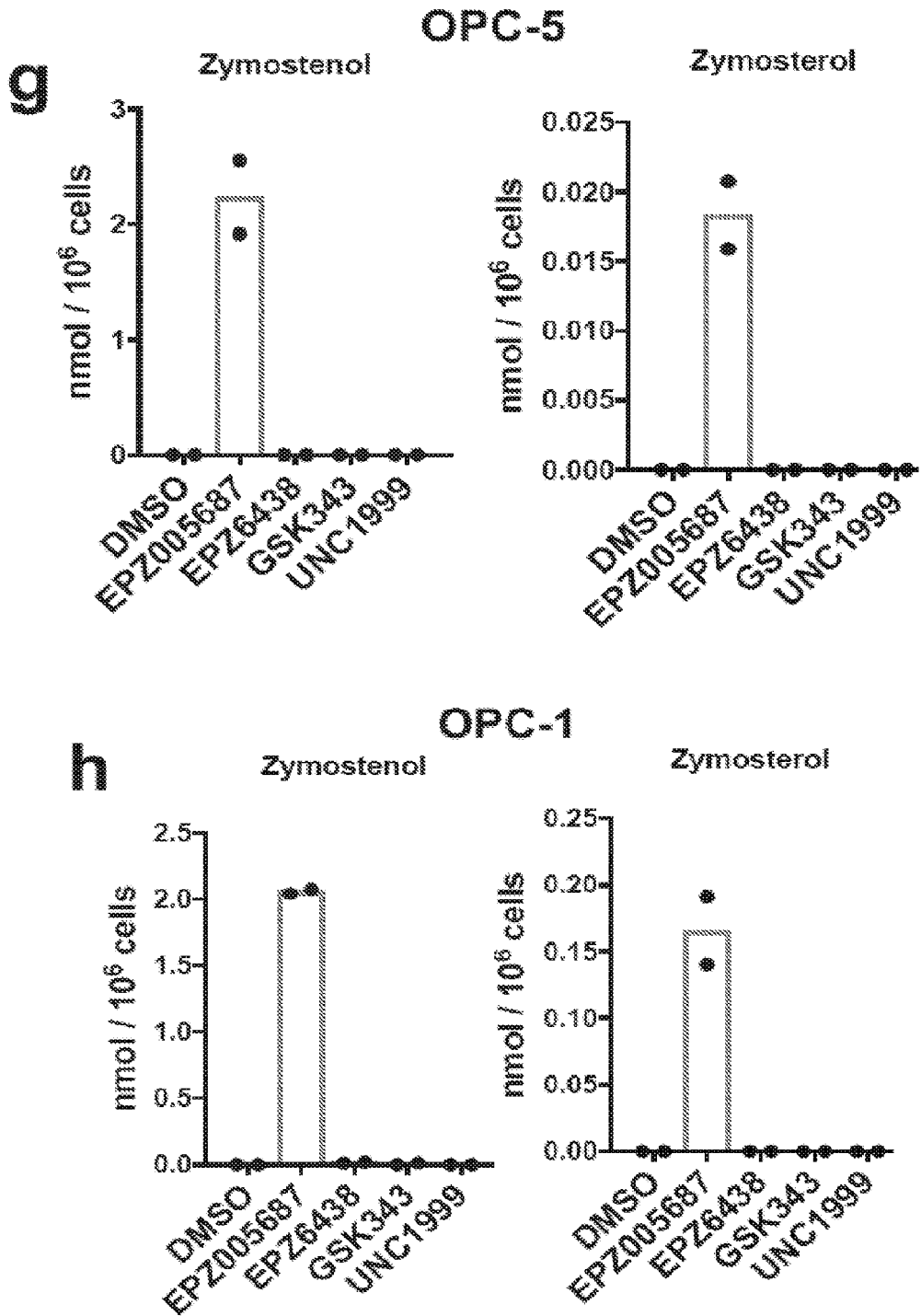
Figs. 8G-H

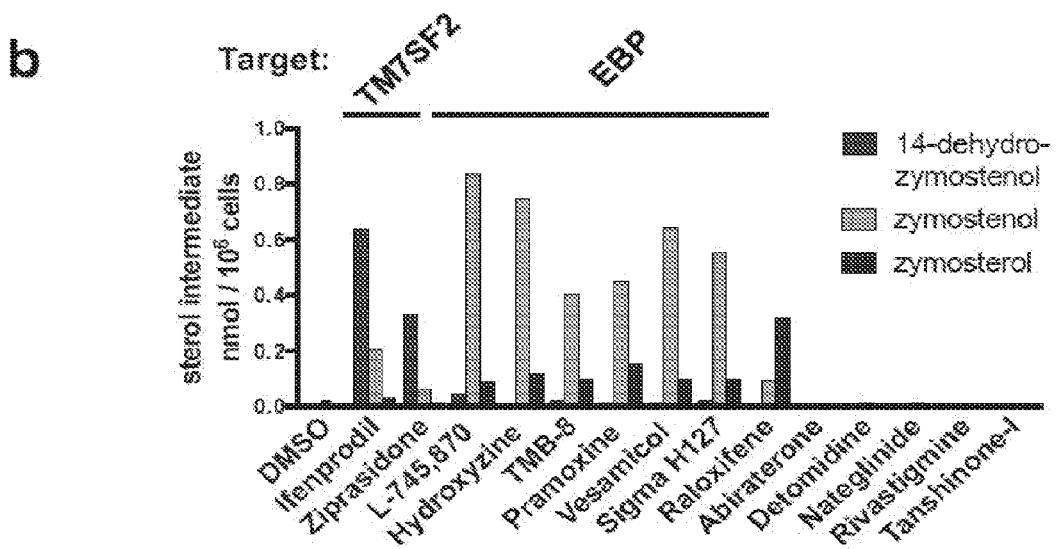
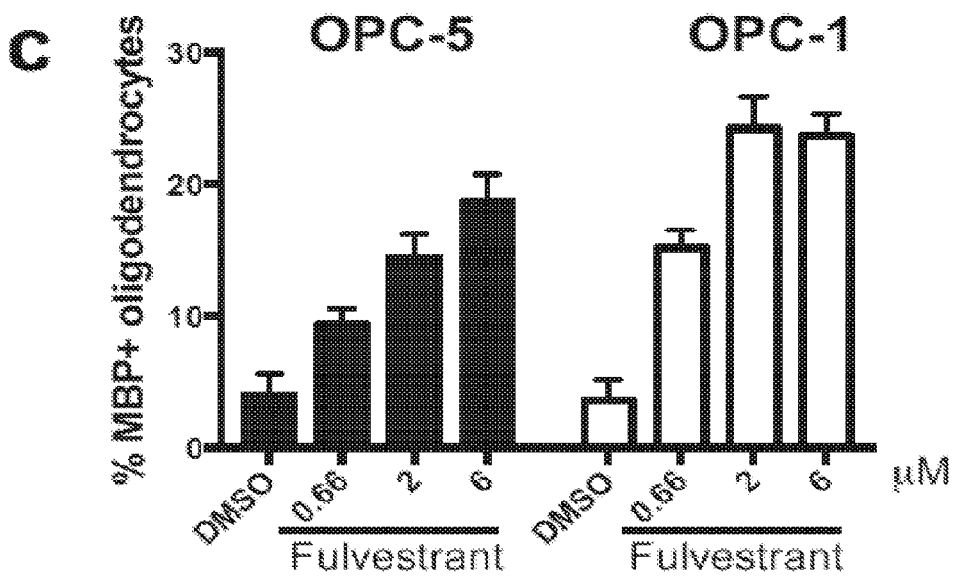
Figs. 9B-C

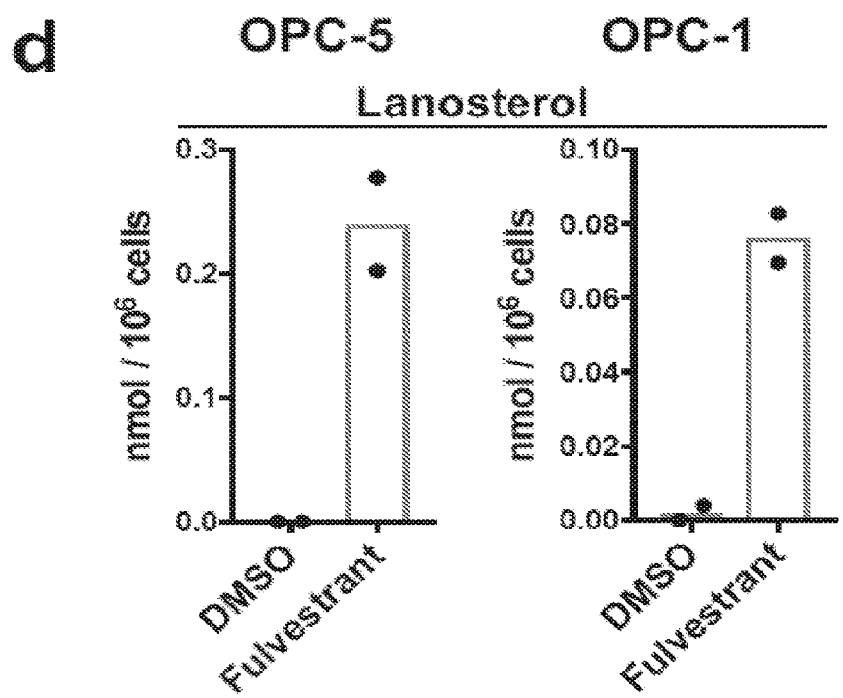
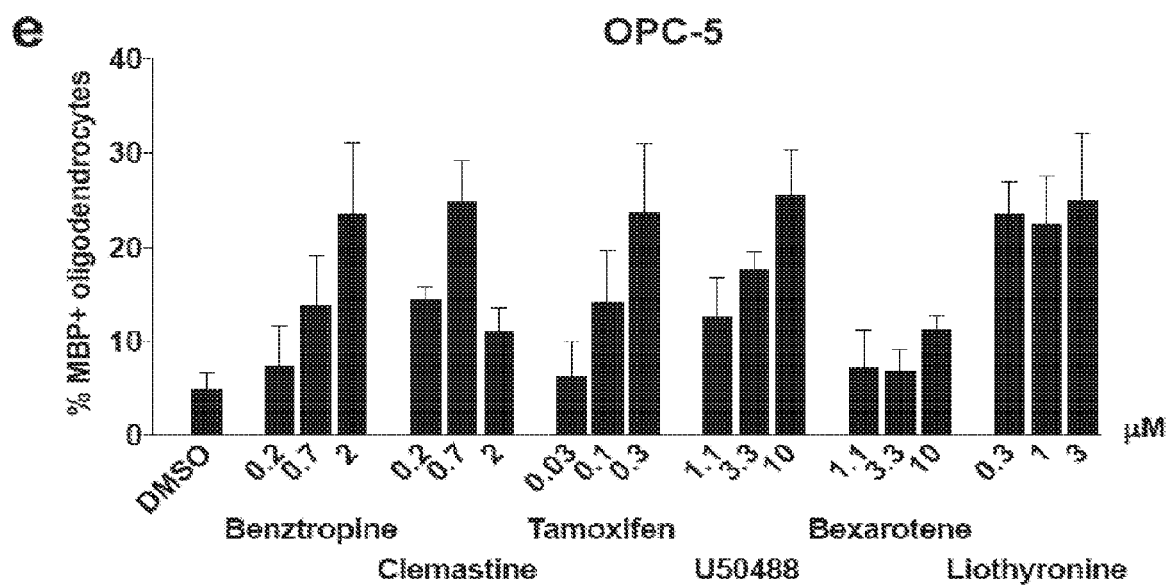
Figs. 9D-E

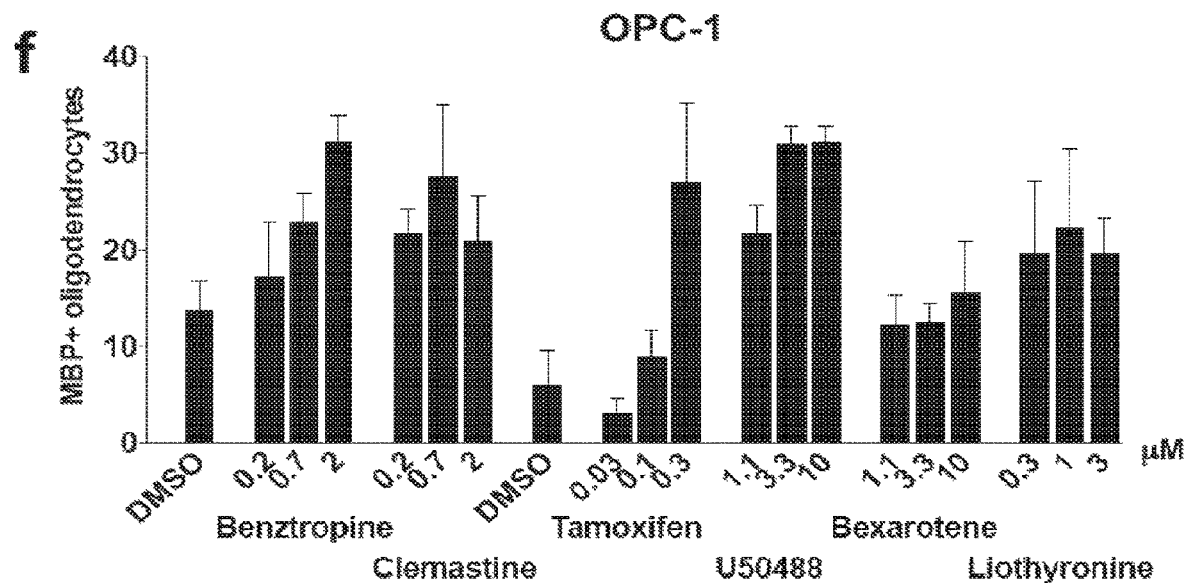
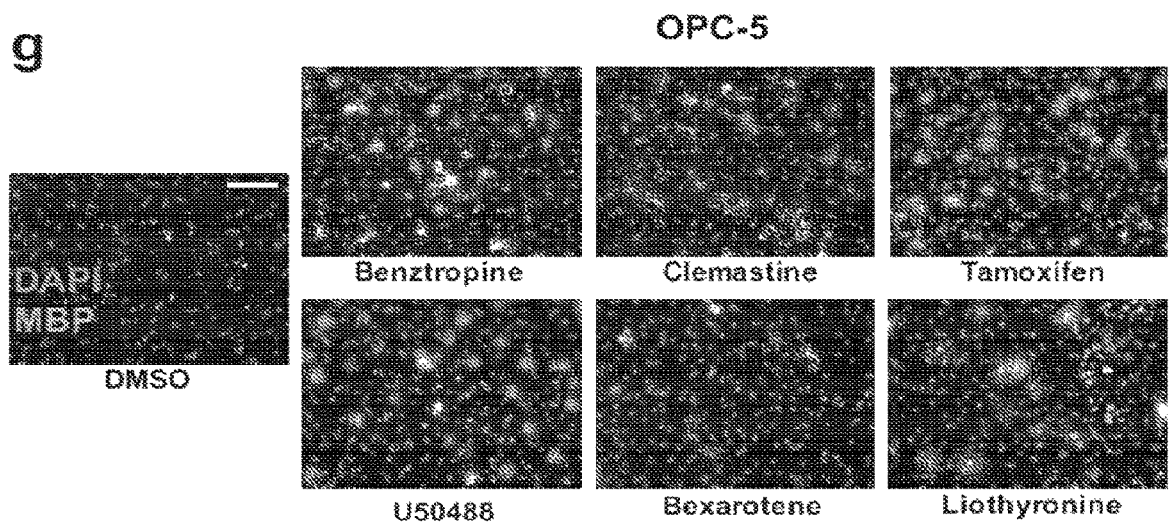
Figs. 9F-G

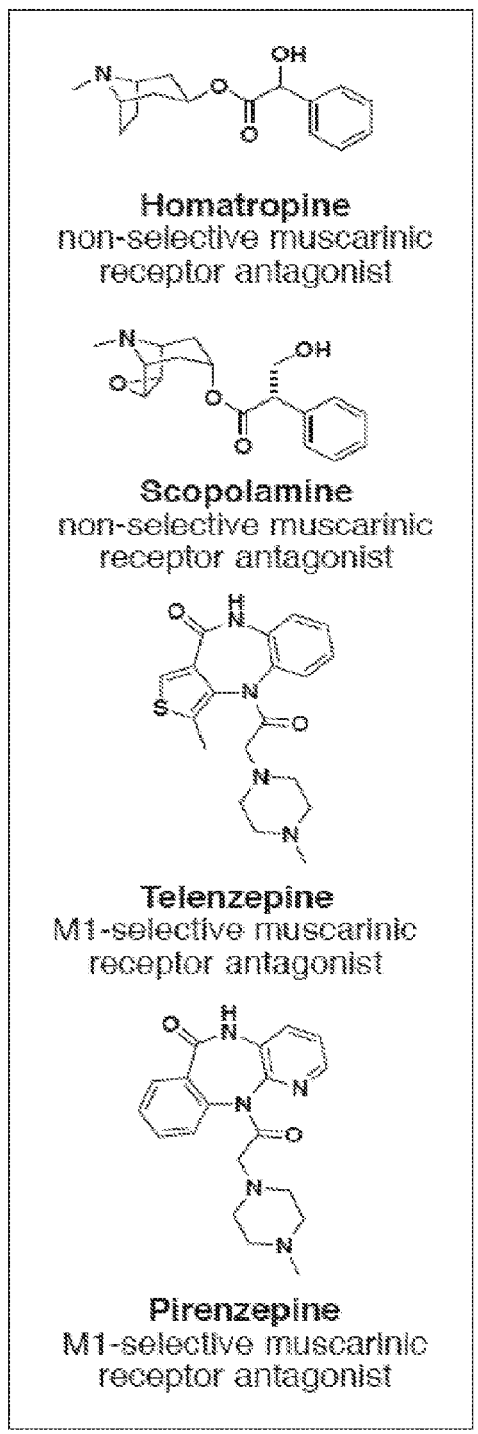
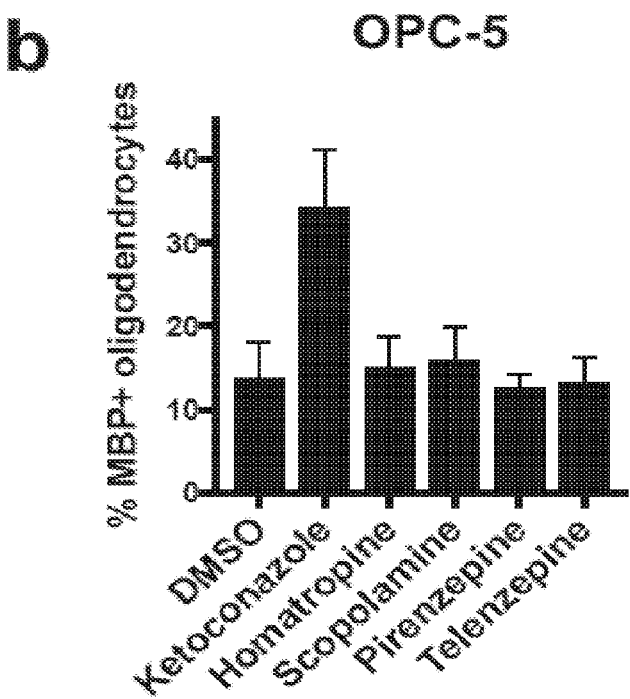
Figs. 10A-B

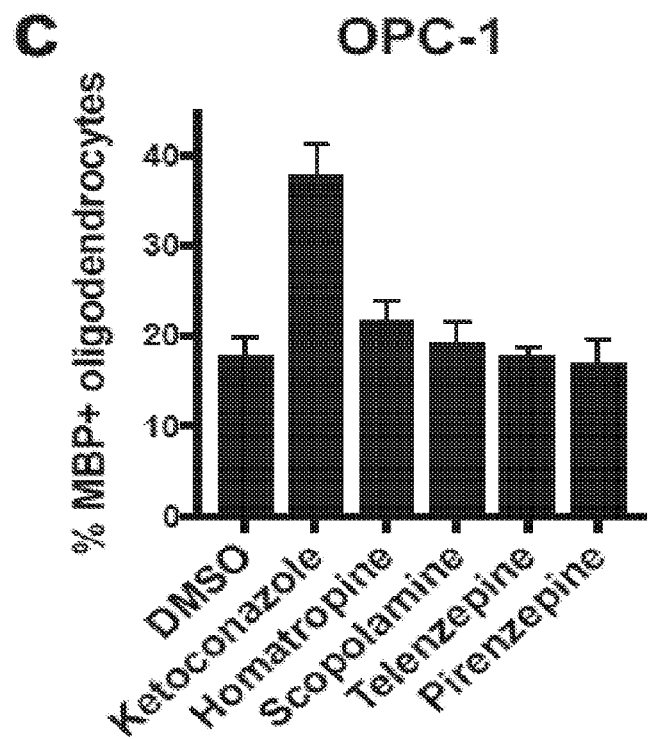
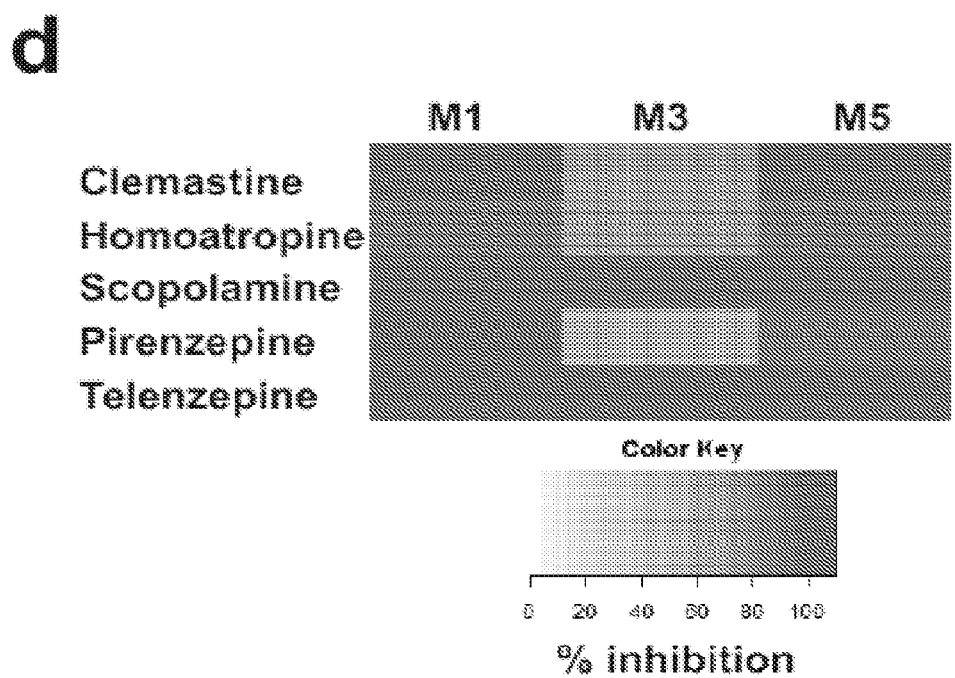
Figs. 10C-D

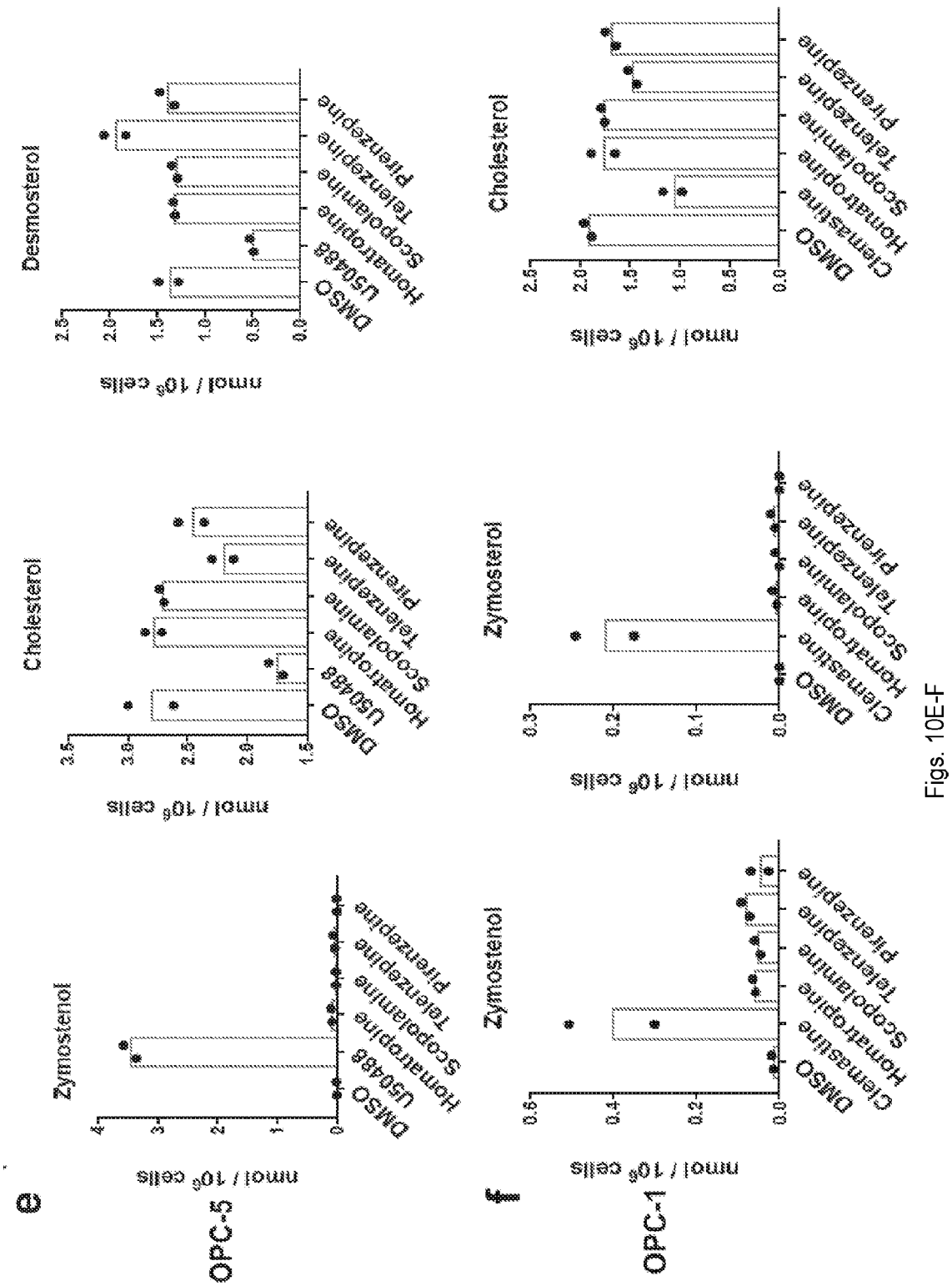
Figs. 10E-F

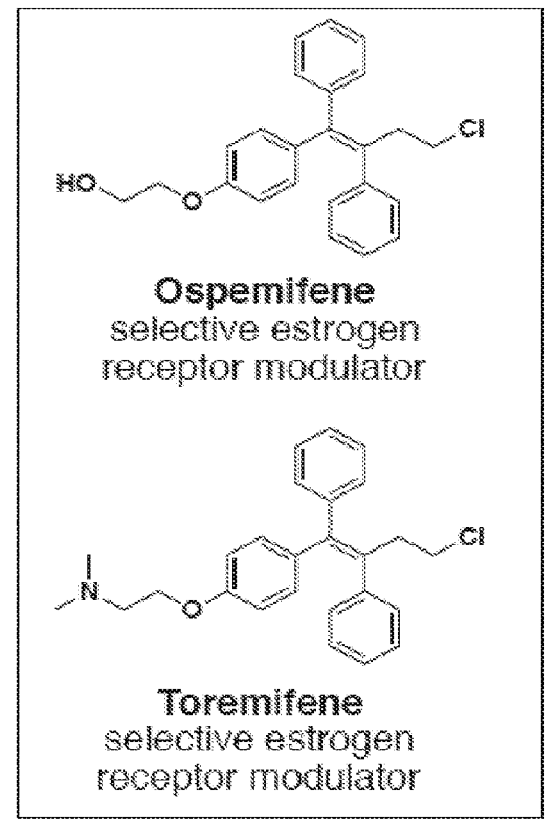
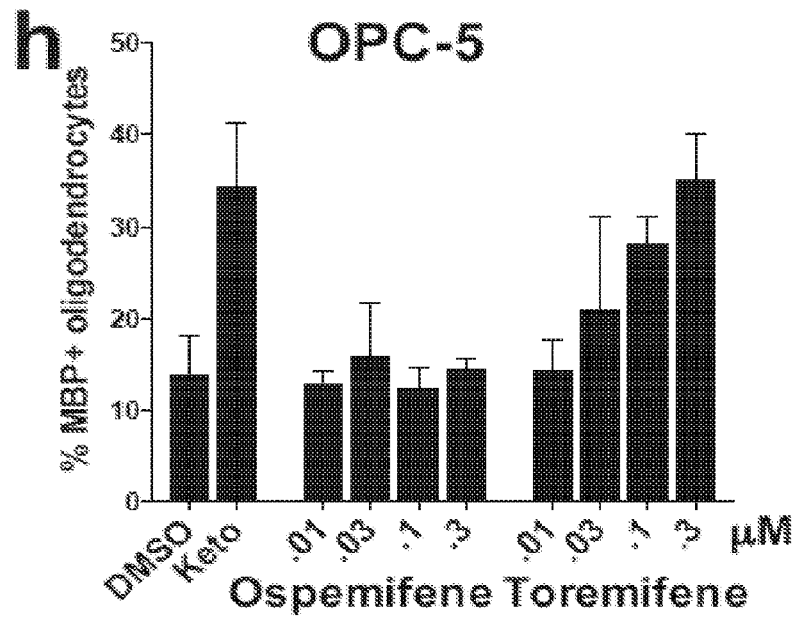
Figs. 10G-H

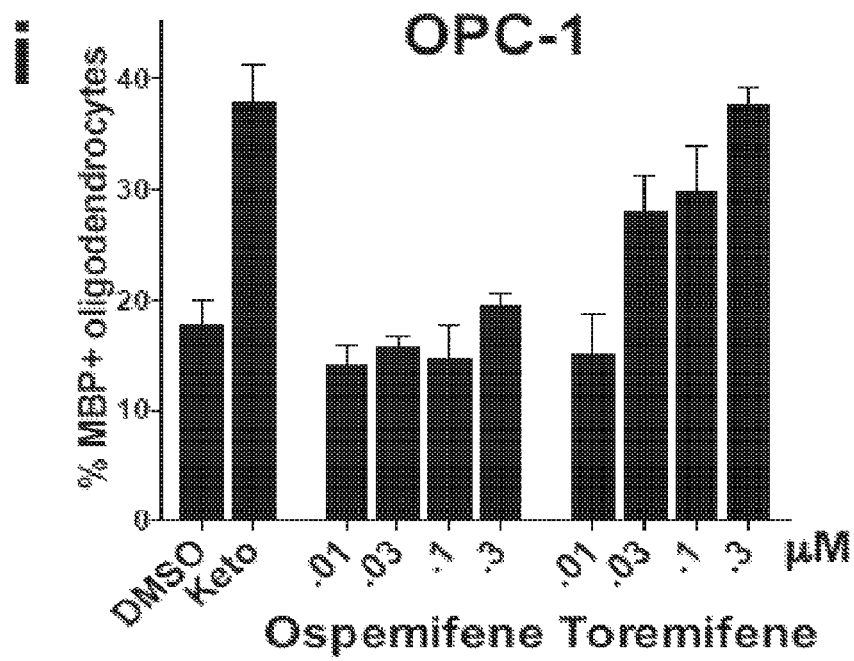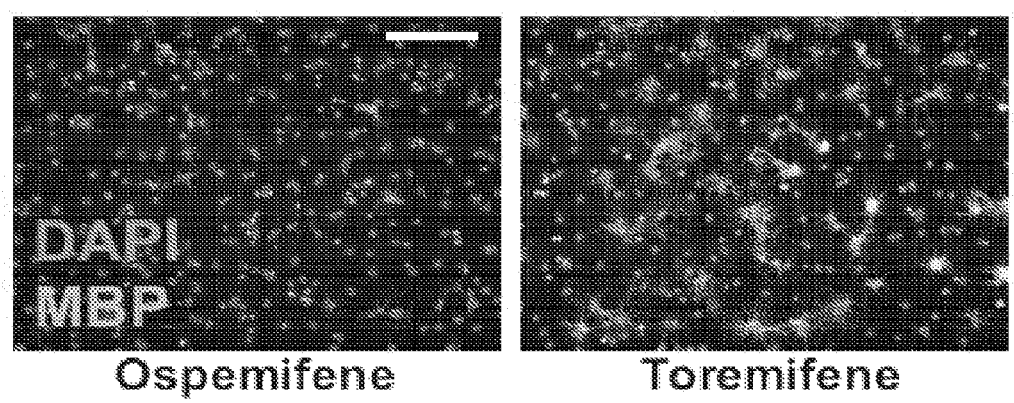
Figs. 10I-J

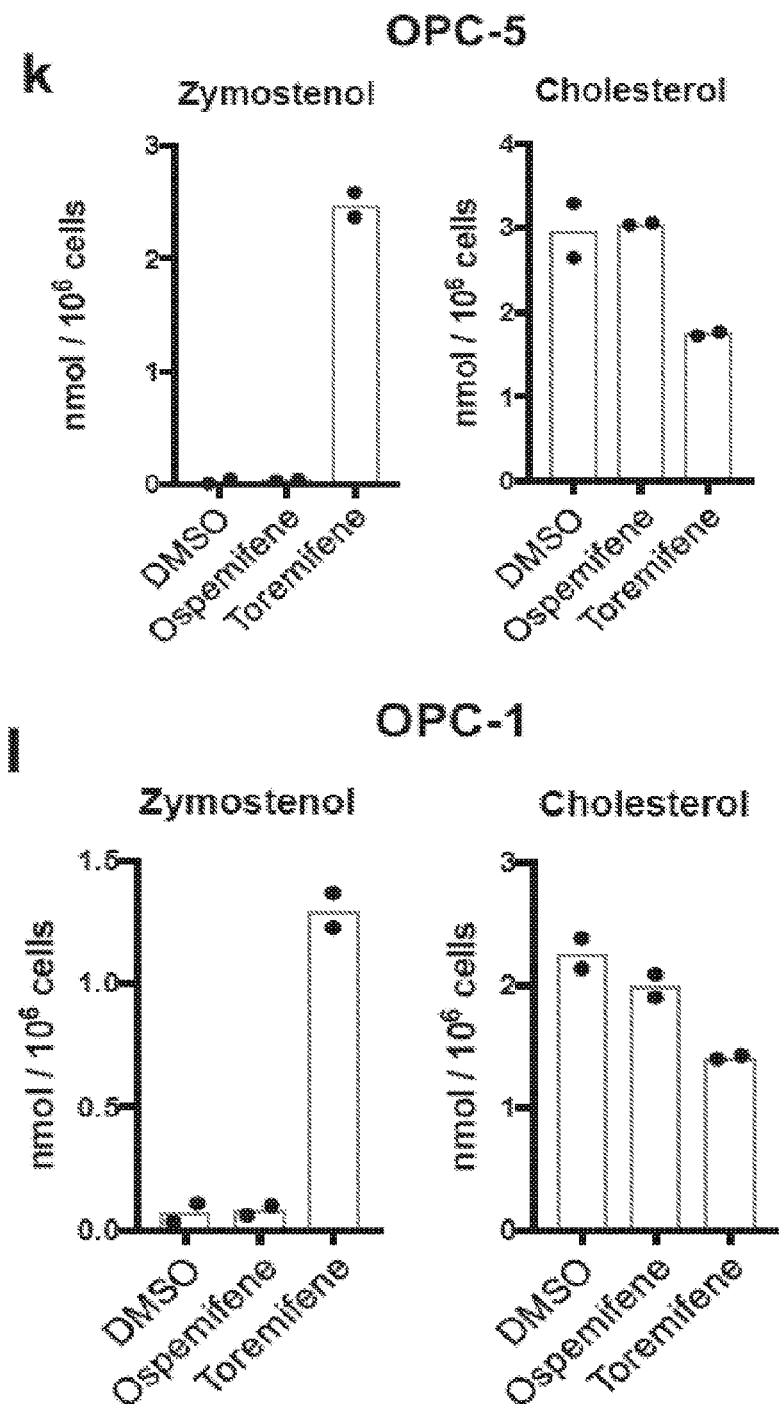
Figs. 10K-L

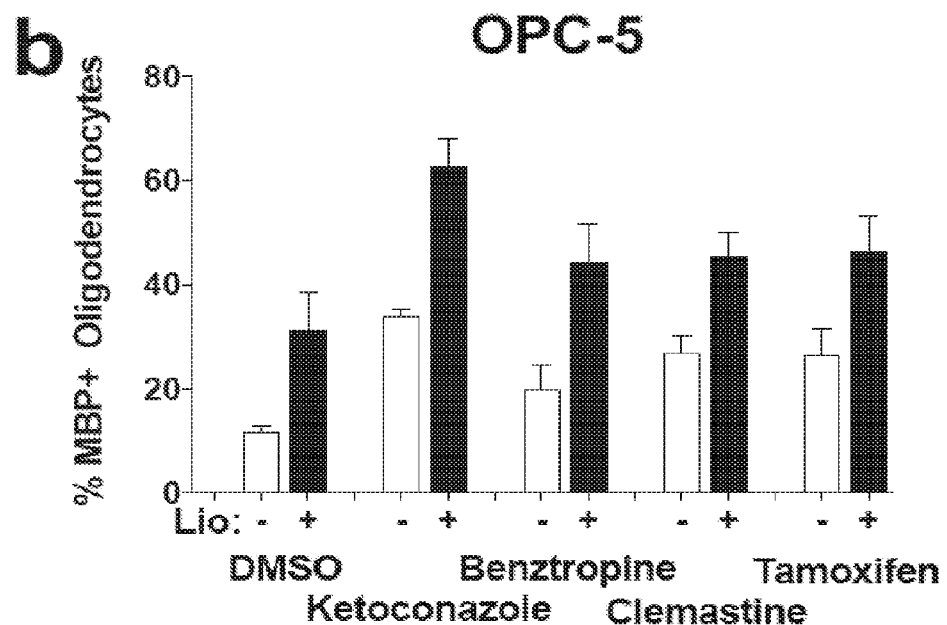
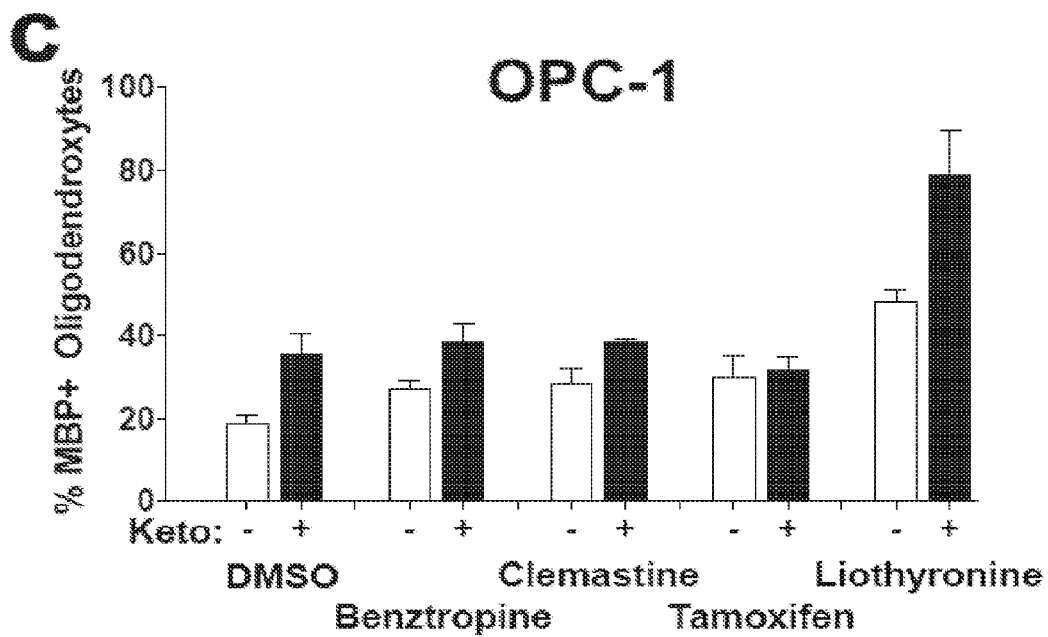
Figs. 11B-C

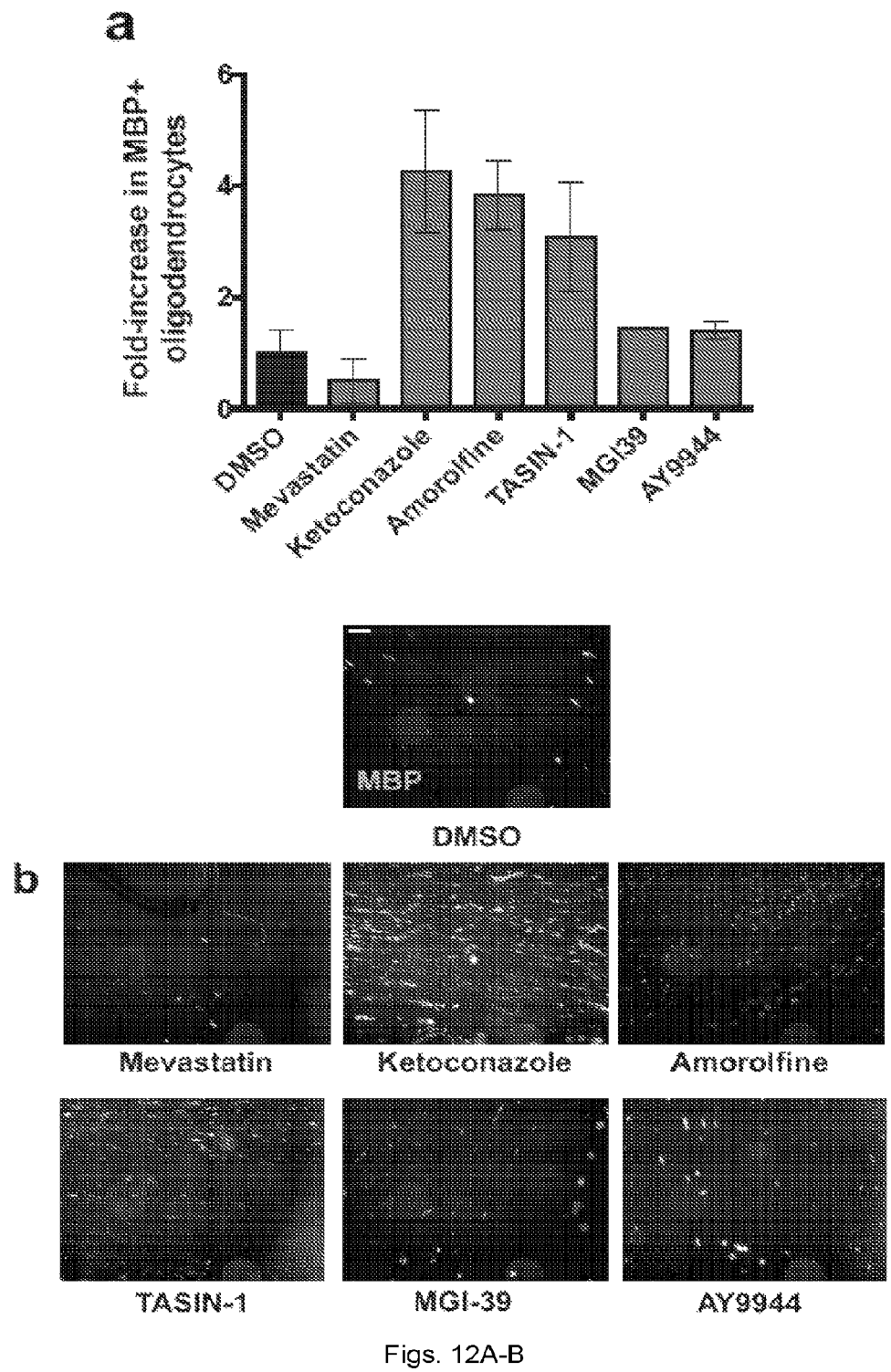
Figs. 12A-B

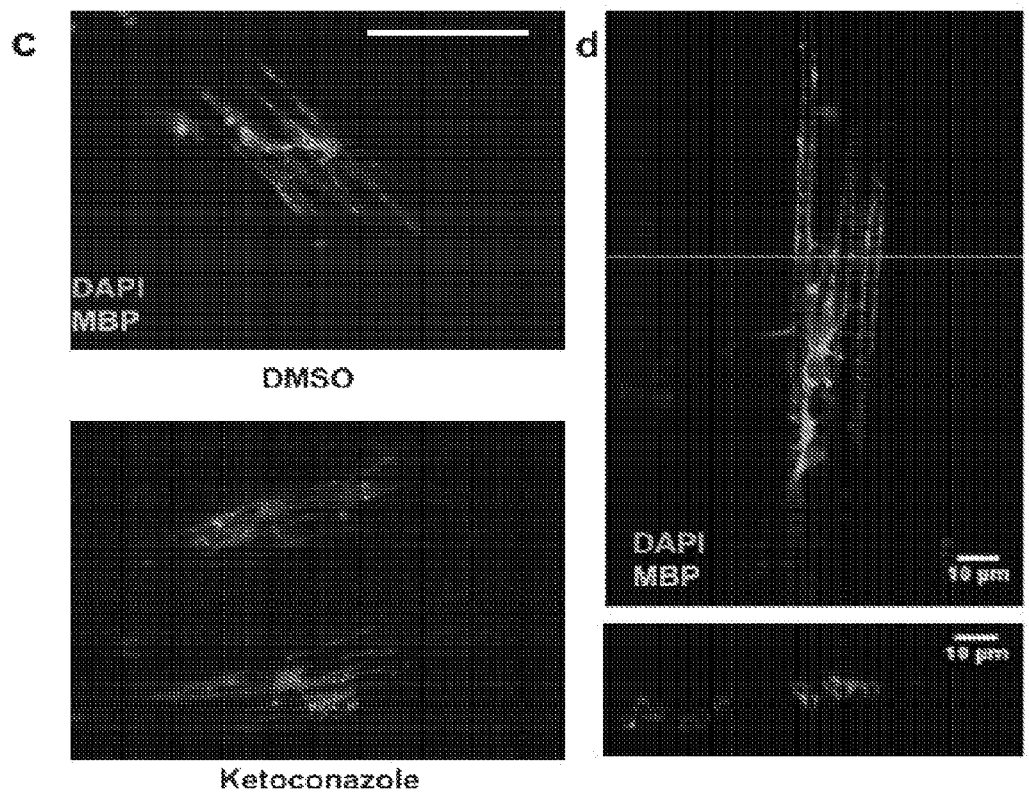
Figs. 12C-D
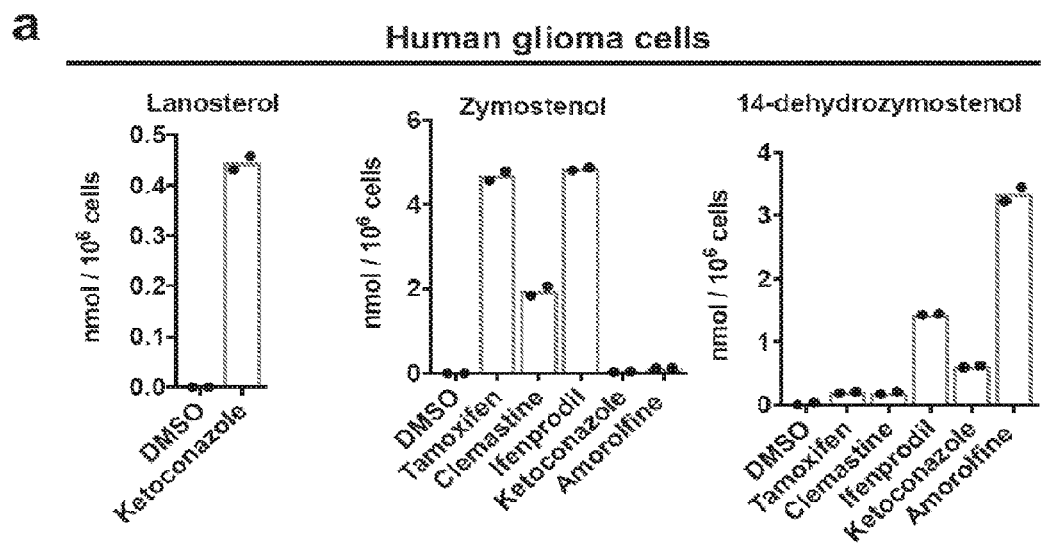
Fig. 13A

CYP51
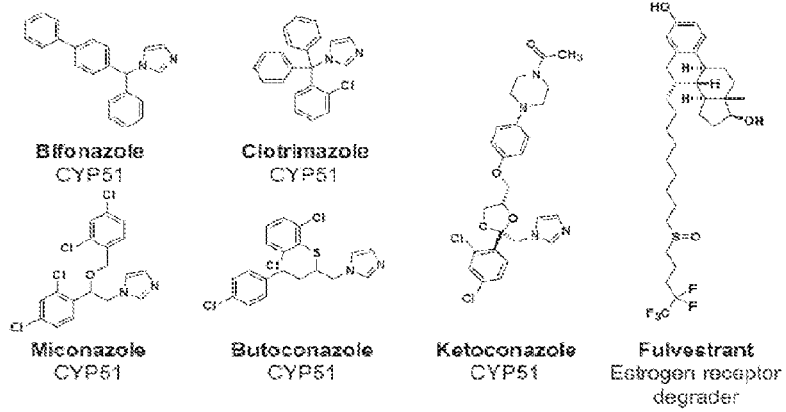
Sterol 14-reductase (TM7SF2 / LBR)
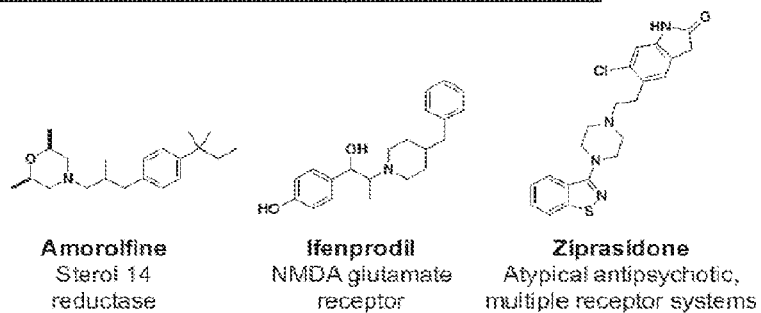
EBP
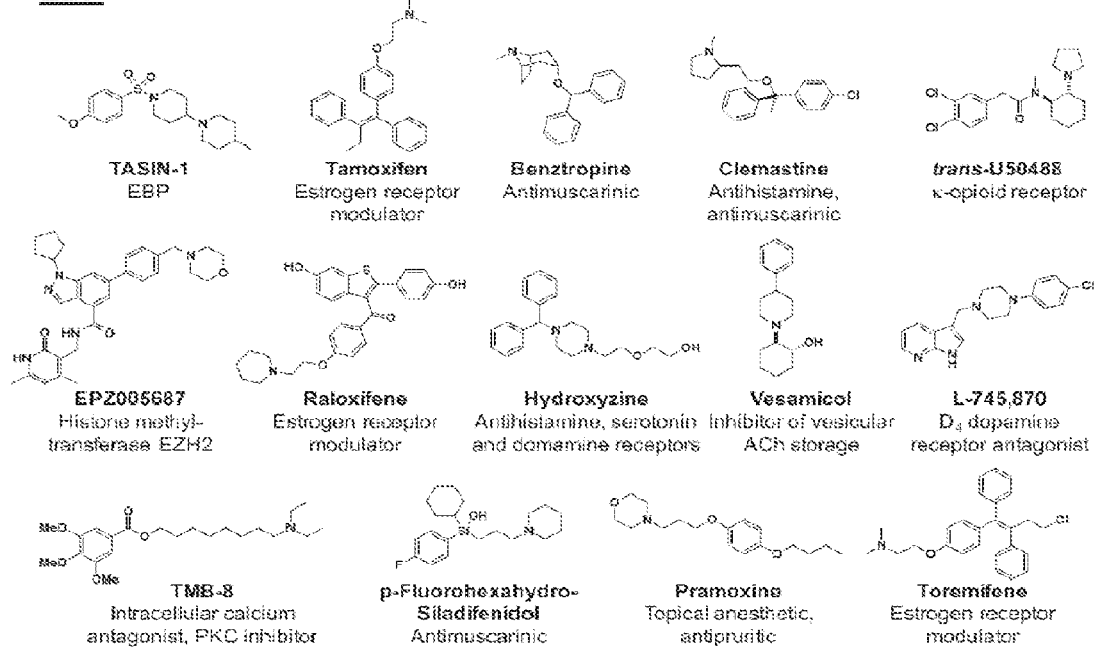
Fig. 14

Other hits from bioactive screening inhibit cholesterol synthesis

Inhibition at at least three steps leads to OPC differentiation:

COMPOUNDS AND METHODS OF PROMOTING MYELINATION

RELATED APPLICATIONS

This Application is a divisional application of U.S. patent application Ser. No. 16/320,554, filed Jan. 25, 2019, which is a U.S. national stage filing, under 35 U.S.C. § 371(c), of International Application No. PCT/US2017/044205, filed on Jul. 27, 2017, which claims priority from U.S. Provisional Application Nos. 62/367,416, filed on Jul. 27, 2016 and 62/452,204 filed on Jan. 30, 2017, the entire contents of each of the above applications are incorporated herein by reference in their entirety.

GOVERNMENT FUNDING

This invention was made with government support under Grant No. R01NS095280, awarded by the National Institute of Health. The government has certain rights in the invention.

BACKGROUND

Multiple sclerosis (MS) is a complex neurological disease characterized by deterioration of central nervous system (CNS) myelin. This insulating material, composed in its majority by lipids (70% lipids, 30% protein), protects axons and makes possible the saltatory conduction, which speeds axonal electric impulse. Demyelination of axons in chronic MS may result in axon degeneration and neuronal cell death, but more specifically, MS destroys oligodendrocytes, the highly specialized CNS cells that generate and maintain myelin.

Oligodendrocyte precursors (PDGFRα+, NG2-proteoglycan+), the immature oligodendrocytes, are generated in ventral areas of the developing brain from a common glial progenitor, actively migrate and proliferate populating the CNS to finally differentiate to premyelinating oligodendrocytes (O4+). At this maturation point, oligodendrocytes both target and extend myelin sheaths along axons or they die. Less explored has been however, the hypothesis of enhanced myelination and/or remyelination by either endogenous oligodendrocyte precursors or transplanted cells.

Inducing differentiation and/or promoting survival during the maturation of endogenous oligodendrocyte progenitors can stimulate and enhance the generation of new oligodendrocytes and intrinsic myelination and/or remyelination. Therefore, there is a need for compounds and therapeutic methods capable of enhancing the generation of new oligodendrocytes.

SUMMARY

Embodiments described herein generally relate to agents, compounds, and methods for enhancing oligodendrocyte generation by inducing, promoting, and/or modulating oligodendrocyte precursor cell differentiation, proliferation and/or maturation as well as to methods for the treatment of disease or disorders in subjects where myelination or remyelination is beneficial to the subject.

It was found that the enhancement and/or inducement of the accumulation of Δ8,9-unsaturated sterol intermediates of the cholesterol biosynthesis pathway in oligodendrocyte progenitor cells (OPCs) can induce Oligodendrocyte generation. Enhancement and/or inducement of the accumulation of Δ8,9-unsaturated sterol intermediates can be provided by modulating and/or inhibiting enzymes within the cholesterol biosynthesis pathway in OPCs that inhibit Δ8,9-unsaturated sterol intermediate accumulation and/or for which the Δ8,9-unsaturated sterol intermediates are substrates as well as directly and/or indirectly administering Δ8,9-unsaturated sterol intermediates to the OPCs. Enhancement and/or inducement of the accumulation of Δ8,9-unsaturated sterol intermediates can promote OPC differentiation, survival, proliferation and/or maturation and treat diseases and/or disorders in subjects where myelination or remyelination is beneficial to the subject.

In some embodiments, an agent that enhances and/or induces accumulation of Δ8,9-unsaturated sterol intermediates of the cholesterol biosynthesis pathway in the OPCs can be administered to a subject and/or the OPCs at an amount effective to promote and/or induce OPC differentiation, proliferation and/or maturation as well as oligodendrocyte generation. In one example, the agent can include at least one compound that inhibits enzyme mediated synthesis of one or more sterol intermediates in the cholesterol biosynthesis pathway of the OPCs and/or promotes accumulation of Δ8,9-unsaturated sterol intermediates.

In some embodiments, the compound can modulate and/or inhibit one or more enzyme mediated conversion steps of the cholesterol biosynthesis pathway from lanosterol to cholesterol, for example, between lanosterol and/or lathosterol, of OPCs to promote and/or induce oligodendrocyte generation. For example, the compound can inhibit CYP51, sterol 14-reductase, and/or EBP enzyme mediated synthesis of sterol intermediates in the cholesterol biosynthesis pathway. In yet another example, the compound can modulate and/or inhibit enzyme mediated conversion of lanosterol to 4,4-dimethylcholesta-8(9),14,24-trien-3β-ol, 4,4-dimethylcholesta-8(9),14,24-trien-3β-ol to zymostenol, and/or zymostenol to lathosterol to enhance oligodendrocyte generation.

In some embodiments, the compound can modulate and/or inhibit one or more enzyme mediated conversion steps of the cholesterol biosynthesis pathway from lanosterol to dehydrolathosterol or lathosterol.

In some embodiments, a compound used in the methods described herein can inhibit enzyme mediated conversion of zymostenol to lathosterol through the inhibition of emopamil binding protein (EBP) isomerase enzyme activity. Alternatively, a compound used in the methods described herein can inhibit sterol C14 reductase enzyme activity or CYP51 enzyme activity in the cholesterol biosynthesis pathway.

In some embodiments, the compound is selected from the group consisting of bifonazole, clotrimazole, miconazole, butoconazole, ketoconazole, Fulvestrant, amorolfine, ifenprodil, ziprasidone, Tasin-1, tamoxifen, benztropine, clemastine, trans-U50488, EPZ005687, raloxifene, hydroxyzine, vesamicol, L-745,870, TMB-8, Cis-N-cyclohexyl-N-ethyl-3-(3-chloro-4-cyclohexylphenyl)prop-2-enylamine, pFluorohexahydro-Siladifenidol, pramoxine, toremifene, and combinations thereof.

In other embodiments, the compound can include interfering RNA, such as siRNA, or CRISPR/Cas nuclease that inhibits expression of an enzyme that synthesizes one or more sterol intermediates in the cholesterol biosynthesis pathway of the OPCs. For example, the interfering RNA CRISPR/Cas nuclease can inhibit CYP51, sterol 14-reductase, and/or EBP enzyme expression.

In other embodiments, the agent can include at least one Δ8,9-unsaturated sterol intermediate of the cholesterol biosynthesis pathway in OPCs or a derivative thereof that enhances generation of oligodendrocytes from the OPCs. The Δ8,9-unsaturated sterol intermediate can include at least one of lanosterol, 14-dehydrozymostenol, FF-MAS, MAS-412, zymosterol, zymostenol and derivatives thereof.

In some embodiments, the compounds described herein can be used to treat neurodegenerative diseases and disorders in a subject in need thereof. In some embodiments, the neurodegenerative disease or disorder is a myelin related disorder. Myelin related diseases or disorders include diseases, disorders or injuries which relate to dysmyelination or demyelination in a subject's neural cells, e.g., CNS neurons. Examples of myelin related diseases and disorders are multiple sclerosis (MS), neuromyelisits optica (NMO), progressive multifocal leukoencephalopathy (PML), encephalomyelitis (EPL), central pontine myelolysis (CPM), adrenoleukodystrophy, Alexander's disease, Pelizaeus Merzbacher disease (PMD), Vanishing White Matter Disease, Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, Bassen-Kornzweig syndrome, Marchiafava-Bignami syndrome, metachromatic leukodystrophy, trigeminal neuralgia, acute dissmeminated encephalitis, Guillian-Barre syndrome, Charcot-Marie-Tooth disease Bell's palsy, and mental health disorders such as schizophrenia.

BRIEF DESCRIPTION OF THE DRAWINGS

FIGS. 3(A-F) illustrate graphs showing inhibiting steps between CYP51 and EBP is a unifying mechanism for many small enhancers of oligodendrocyte formation identified by high-throughput screening. A) Percentage of MBP+ oligodendrocytes generated from OPCs at 72 h following treatment with ketoconazole, nine molecules identified by bioactives screening, and nine randomly chosen library members at a uniform dose of 5 n=4 replicates per condition, with >1,000 cells analyzed per replicate. B) GC/MS-based quantitation of zymosterol, zymostenol, and 14-dehydrozymostenol levels in OPCs treated 24 h with the indicated screening hits and randomly chosen library members at 2 μM. One replicate per condition, with findings confirmed in a second OPC derivation (FIG. 9B). Molecules are clustered by enzyme targeted (lop labels). C) GC/MS-based quantitation of zymostenol levels in OPCs treated 24 h with the indicated previously-reported enhancers of oligodendrocyte formation. Unless otherwise noted, the following concentrations were used: benztropine, 2 μM; clemastine 1 μM; tamoxifen 100 nM; U50488 5 μM; bexarotene, 1 μM; liothyronine, 3 μM. D) GC/MS-based quantitation of cholesterol levels in OPCs treated 24 h with the indicated previously-reported enhancers of oligodendrocyte formation. E) GC/MS-based quantitation of EBP enzymatic activity in a biochemical assay following treatment with small molecules (10 μM) that inhibit EBP in OPCs or do not inhibit EBP in OPCs. n=3. F) Percentage of MBP+ oligodendrocytes generated from OPCs at 72 h following treatment with the indicated combinations of enhancers of oligodendrocyte formation. n=4 replicates per treatment condition, with >1,000 cells analyzed per replicate. Keto=ketoconazole, 2.5 μM.

Figure 1A:
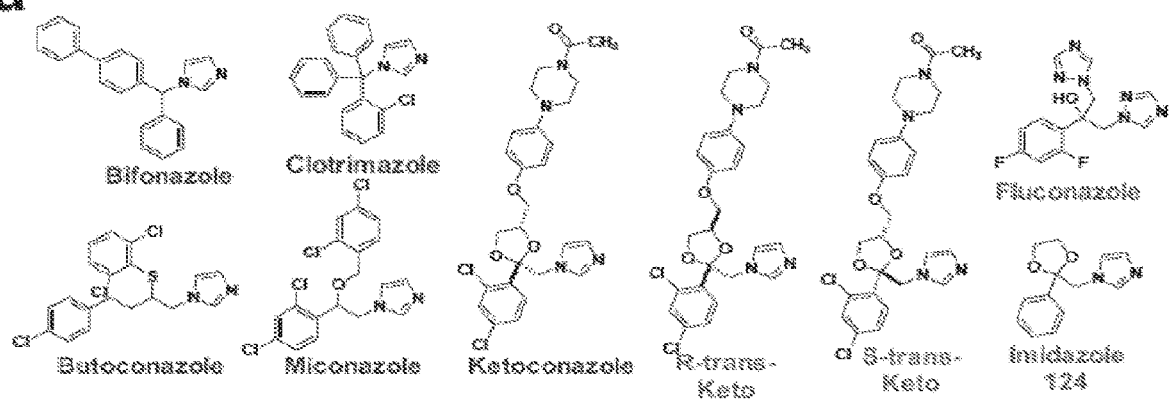
FIGS. 1(A-J) illustrate structures, plots, graphs, and images showing CYP51 is the functional target by which imidazole antifungals enhance oligodendrocyte formation. A) Azole molecules with varying degrees of potency for mammalian CYP51 inhibition. B) Rat CYP51 enzymatic activity following treatment with azoles as measured by LC/MS-based quantitation of the CYP51 product FF-MAS (4,4-dimethyl-5a-cholesta-8,14,24-trien-3(3β-ol). n=2 independent enzymatic assays. C) Percentage of MBP+ oligodendrocytes generated from OPCs at 72 h following treatment with azoles. n=4 replicates per condition, with >1,000 cells analyzed per replicate. D) Representative images of OPCs treated 72 h with the indicated imidazole antifungals. E) GC/MS-based quantitation of lanosterol levels in OPCs treated 24 h with the indicated azoles at 2.5 μM. n=2 replicates per condition. F) GC/MS-based quantitation of lanosterol levels in OPCs treated 24 h with the indicated doses of ketoconazole. n=2 replicates per condition. G) CYP51 mRNA levels measured by RT-qPCR following 4 d treatment with non-targeting or CYP51-targeting pools of cell-permeable siRNAs. n=2 replicates, with quadruplicate qPCR measurements per replicate. H) GC/MS-based quantitation of lanosterol levels in OPCs treated 96 h with the indicated reagents. n=2 replicates per condition, Ketoconazole, 2.5 μM. I) Percentage of MBP+ oligodendrocytes generated from OPCs at 72 h following treatment with the indicated reagents. n=2 independent experiments, 4 replicates per condition, with >1,000 cells analyzed per replicate. Two-tailed t-test, **P<0.01 for siRNA groups compared with their respective non-targeting control-treated group. J) Percentage of MBP+ oligodendrocytes generated from OPCs at 72 h following treatment with exogenous lanosterol. n=4 replicates per condition, with >1,000 cells analyzed per replicate.

Mann-Whitney, *U<0.05 and **U<0.01 for drug-treated groups compared with their respective vehicle-treated group.

FIGS. 5(A-N) illustrate graphs and images showing CYP51 is the functional target by which imidazole antifungals enhance oligodendrocyte formation. A) GC/MS-based quantitation of cholesterol levels in OPCs (OPC-5) treated 24 h with the indicated azoles at 2.5 µM. n=2 replicates per condition. B) Percentage of MBP+ oligodendrocytes generated from a second, independent derivation of OPCs (OPC-1) at 72 h following treatment with the indicated concentrations of azoles. n=4 replicates per condition, with >1,000 cells analyzed per replicate. C) GC/MS-based quantitation of lanosterol levels in a second derivation of OPCs (OPC-1) treated 24 h with the indicated azoles at 2.5 n=2 replicates per condition. D) GC/MS-based quantitation of cholesterol levels in OPCs (OPC-1) treated 24 h with the indicated azoles at 2.5 µM. n=2 replicates per condition. E) Percentage of MBP+oligodendrocytes generated from mouse primary OPCs at 72 h following treatment with the indicated imidazole antifungals at 3 µM. n=4 replicates per condition, with >1,000 cells analyzed per replicate. F) GC/MS-based quantitation of lanosterol levels in mouse primary OPCs treated 24 h with the indicated imidazole antifungals at 3 µM. n=2 replicates per condition. C) Assessment of oligodendrocyte formation using an alternative image quantitation metric, fold increase in total neurite length. Panel is a re-analysis of data shown in FIG. 1C. n=4 replicates per condition, with >1,000 cells analyzed per replicate. H) Percentage of oligodendrocytes generated from OPCs at 72 h following treatment with the indicated concentrations of azoles as measured by PLP1 immunostaining. Left, OPC-5; right, OPC-1. n=4 replicates per condition, with >1,000 cells analyzed per replicate. I) GC/MS-based quantitation of lanosterol levels in a second independent batch of OPCs treated 24 h with the indicated doses of ketoconazole. n=2 replicates per condition. Concentrations shown in panel i mirror those shown in panel b. J) Representative images of OPC-5 cells treated 72 h with the indicated siRNA reagents. Nuclei are labeled with DAPI (blue), and oligodendrocytes are indicated by immunostaining for myelin basic protein (green). Scale bar, 100 µm. K) GC/MS-based quantitation of lanosterol levels in a second, independent batch of OPCs (OPC-1) treated 96 h with the indicated pooled siRNA reagents. n=2 replicates per condition. L) Percentage of MBP+ oligodendrocytes generated from a second, independent batch of OPCs (OPC-1) at 72 h following treatment with the indicated reagents. n=4 replicates per condition, with >1,000 cells analyzed per replicate. Two-tailed t-test, **P<0.01 for siRNA groups compared with their respective non-targeting control-treated group. M) Representative images of OPC-5 OPCs treated 72 h with lanosterol (47 µM). Nuclei are labeled with DAPI, and oligodendrocytes are indicated by immunostaining for myelin basic protein.

Figure 6:
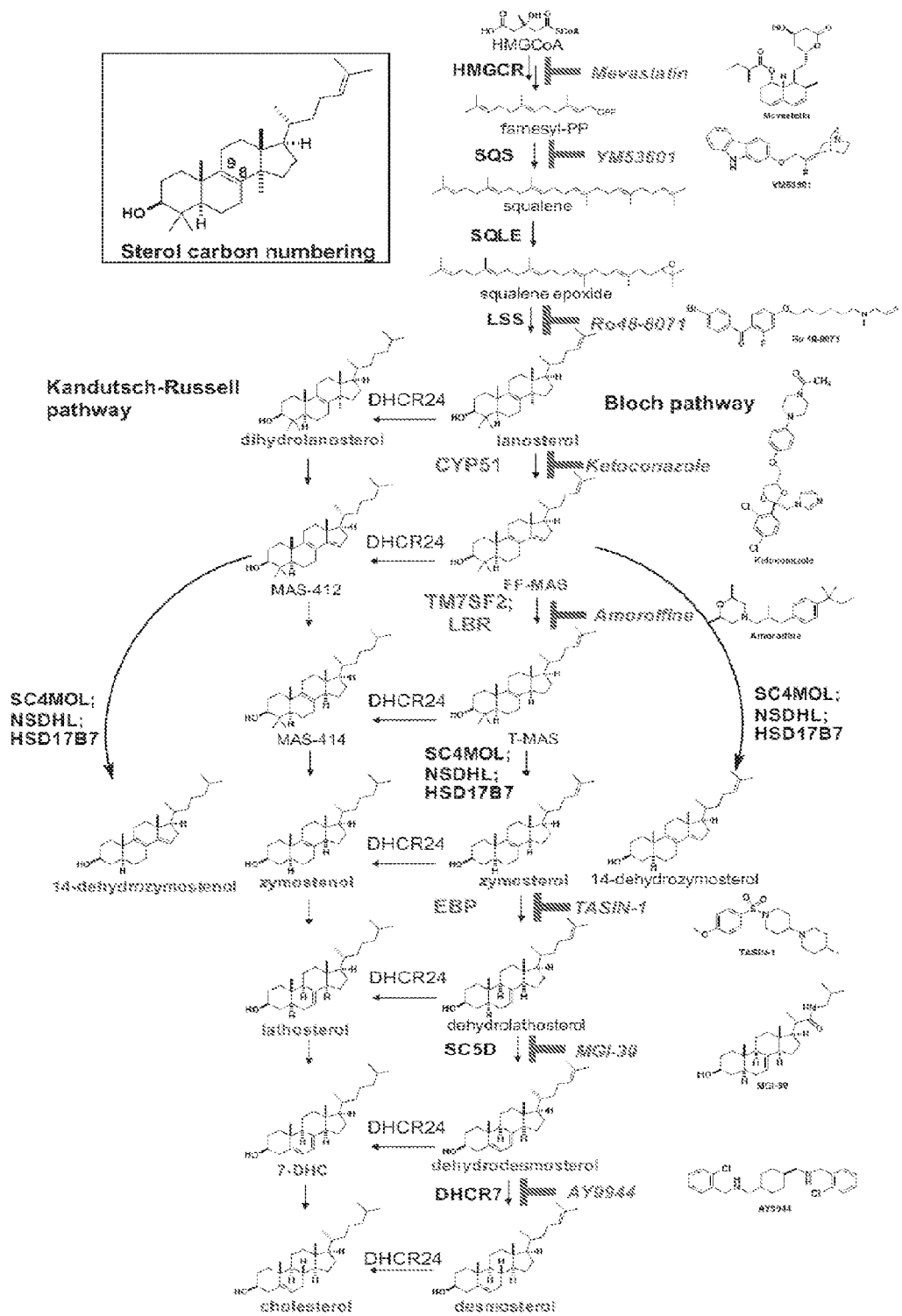

FIG. 6 illustrates a schematic drawing showing an expanded cholesterol synthesis pathway diagram. The cascade cyclization of squalene epoxide, catalyzed by lanosterol synthase (LSS), provides the first sterol, lanosterol. Processing of lanosterol to cholesterol can proceed via either the Kandutsch-Russell or Bloch pathways, which use the same enzymes and process substrates that vary only in the presence or absence of the C24 double bond. Intermediates in blue have been confirmed in our GC/MS-based sterol profiling assay using authentic standards. Sterol 14-reductase activity in mouse is shared by two genes, TM7SF2 and LBR.

FIGS. 7(A-K) illustrate graphs and images showing the effect of small-molecule targeting of enzymes in the cholesterol biosynthesis pathway on enhancing oligodendrocyte formation. A) GC/MS-based quantitation of basal sterol levels in OPCs treated 24 h with the indicated inhibitors of cholesterol biosynthesis. Left, cholesterol; right, desmosterol. n=2 replicates per condition. Inhibitors were used at the following doses unless otherwise noted: mevastatin, ketoconazole, MGI-39, 2.5 µM; YM53601, 2 µM; Ro 48-8071, amorolfine, TASIN-1, 100 nM; AY9944, 200 nM. B) GC/MS-based quantitation of basal sterol levels in a second batch of OPCs (OPC-1). Left, cholesterol; right, desmosterol. n=2 replicates per condition. C) GC/MS-based quantitation of the sterol intermediates expected to accumulate following treatment of OPCs with the indicated inhibitors of cholesterol biosynthesis for 24 h. n=2 replicates per condition. D) GC/MS-based quantitation of the sterol intermediates expected to accumulate following treatment of a second derivation of OPCs (OPC-1) with the indicated inhibitors of cholesterol biosynthesis for 24 h. n=2 replicates per condition. In C and D, no accumulation of other sterol intermediates indicative of off-target effects within the cholesterol pathway were observed. E) Representative images of OPC-5 cells treated 72 h with the indicated small molecules. All treatments are at the highest concentration shown in FIG. 2B. Scale bar, 100 µm. F) Percentage of MBP+ oligodendrocytes generated from a second batch OPCs (OPC-1) at 72 h following treatment with the indicated cholesterol pathway inhibitors. n=4 replicates per condition, with >1,000 cells analyzed per replicate. G) Percentage of MBP+ oligodendrocytes generated from mouse primary OPCs at 72 h following treatment with the indicated cholesterol pathway inhibitors at 300 nM. n=4 replicates per condition, with >1,000 cells analyzed per replicate. H) GC/MS-based quantitation of sterol intermediate levels in mouse primary OPCs treated 24 h with the indicated inhibitors of cholesterol biosynthesis at 300 nM. Left, 14-dehydrozymostenol levels following treatment with amorolfine; Right, zymostenol levels following treatment with TASIN-1. n=2 replicates per condition. I) GC/MS-based quantitation of sterol intermediate levels in OPC-1 OPCs treated 24 h with the indicated doses of inhibitors of cholesterol biosynthesis. Left, 14-dehydrozymostenol levels following treatment with amorolfine; Right, zymostenol levels following treatment with TASIN-1. n=2 replicates per condition. Concentrations shown in panel i mirror those shown in panel f. J) Percentage of MBP+ oligodendrocytes generated from OPC-1 OPCs at 72 h following treatment with the indicated purified sterol intermediates. n=4 replicates per condition, with >1,000 cells analyzed per replicate. Green box highlights metabolites that accumulate after treatments that enhance oligodendrocyte formation in panel e. K) Percentage of MBP+ oligodendrocytes generated from OPC-5 and OPC-1 OPCs at 72 h following treatment with the indicated concentrations of cholesterol. n=4 replicates per condition, with >1,000 cells analyzed per replicate.

FIGS. 8(A-I) illustrate plots, graphs, and images showing the effect of EPZ005687 and related EZH2 inhibitors on cellular EBP function and oligodendrocyte formation. A) Percentage of MBP+ oligodendrocytes (relative to DMSO control replicates) generated from OPCs (OPC-1 derivation) at 72 h following treatment with a library of 3,000 bioactive small molecules, each at 2 µM. B) Four structurally analogous EZH2 inhibitors contained within the bioactives library screened in panel a. C) Percentage of MBP+ oligodendrocytes generated from OPCs at 72 h following treatment with the indicated structurally analogous EZH2 inhibitors. n=4 replicates per condition, with >1,000 cells analyzed per replicate. D) Percentage of MBP+oligodendrocytes generated from a second batch of OPCs at 72 h following treatment with the indicated structurally analogous EZH2 inhibitors. n=4 replicates per condition, with >1,000 cells analyzed per replicate. E) Percentage of MBP+ oligodendrocytes generated from mouse primary OPCs at 72 h following treatment with EPZ005687. n=4 replicates per condition, with >1,000 cells analyzed per replicate. F) Representative images of OPCs treated 72 h with the indicated EZH2 inhibitors. All treatments are at 2 µM. Scale bar, 100 µm. G) GC/MS-based quantitation of two sterol intermediates following treatment of OPCs with the indicated EZH2 inhibitors at 1 µM for 24 h. Left, zymostenol; right, zymosterol. n=2 replicates per condition. H) GC/MS-based quantitation of two sterol intermediates following treatment of a second derivation of OPCs with the indicated EZH2 inhibitors at 1 µM for 24 h. Left, zymostenol; right, zymosterol. n=2 replicates per condition. I) GC/MS-based quantitation of two sterol intermediates following treatment of mouse primary OPCs with EPZ005687 at 2 µM for 24 h. Left, zymostenol; right, zymosterol. n=2 replicates per condition.

Figure 9A:
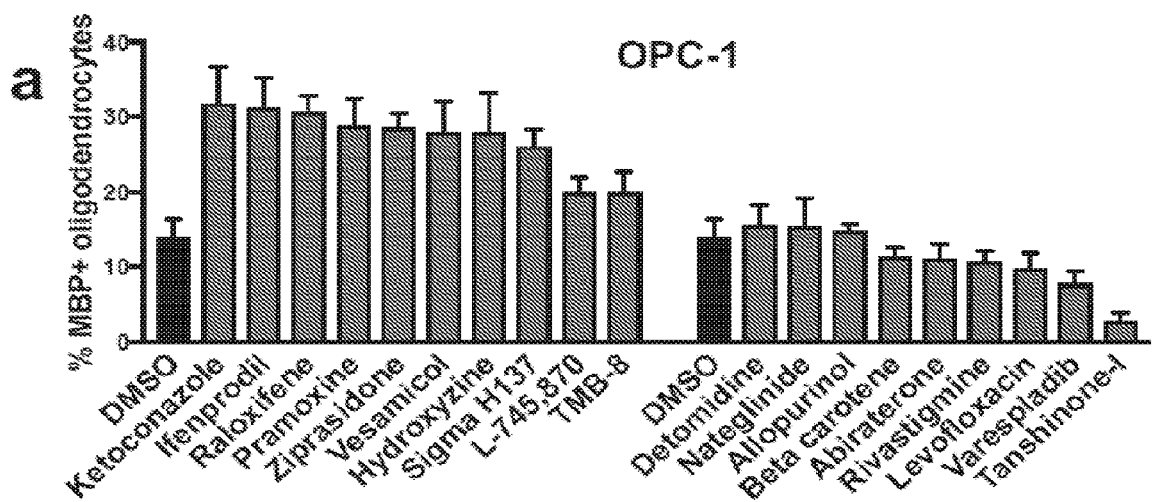

FIGS. 9(A-H) illustrate inhibiting steps between CYP51 and EBP is a unifying mechanism for many small enhancers of oligodendrocyte formation identified by high-throughput screening. A) Percentage of MBP+ oligodendrocytes generated from a second derivation of OPCs at 72 h following treatment with ketoconazole, nine molecules identified by bioactives screening, and nine randomly chosen library members at a uniform dose of 5 µM. n=4 replicates per condition, with >1,000 cells analyzed per replicate. B) GC/MS-based quantitation of zymosterol, zymostenol, and 14-dehydrozymostenol levels in a second batch of OPCs treated 24 h with the indicated screening hits and randomly chosen library members at 2 n=2 replicates per condition. Molecules are clustered by enzyme targeted (top labels). C) Percentage of MBP+ oligodendrocytes generated from OPCs at 72 h following treatment with the indicated doses of fulvestrant. n=4 replicates per condition, with >1,000 cells analyzed per replicate. D) GC/MS-based quantitation of lanosterol levels in OPCs treated 24 h with fulvestrant at 2 µM. n=2 replicates per condition. E) Percentage of MBP+ oligodendrocytes generated from OPCs at 72 h following treatment with the indicated previously-reported enhancers of oligodendrocyte formation. n=4 replicates per condition, with >1,000 cells analyzed per replicate. F) Percentage of MBP+ oligodendrocytes generated from a second derivation of OPCs at 72 h following treatment with the indicated previously-reported enhancers of oligodendrocyte formation. n=4 replicates per condition, with >1,000 cells analyzed per replicate. G) Representative images of OPCs treated 72 h with the indicated small molecules. All treatments in G are at the highest concentration shown in panel E. Scale bar, 100 µm. H) GC/MS-based quantitation of two metabolite levels in a second derivation of OPCs treated 24 h with the indicated previously-reported enhancers of oligodendrocyte formation at the following doses: Benztropine, 2 µM; Clemastine 1 µM; Tamoxifen 100 nM; U50488 5 µM; bexarotene, 1 µM; liothyronine, 3 µM. Left, zymostenol; right, cholesterol.

Figure 10M:
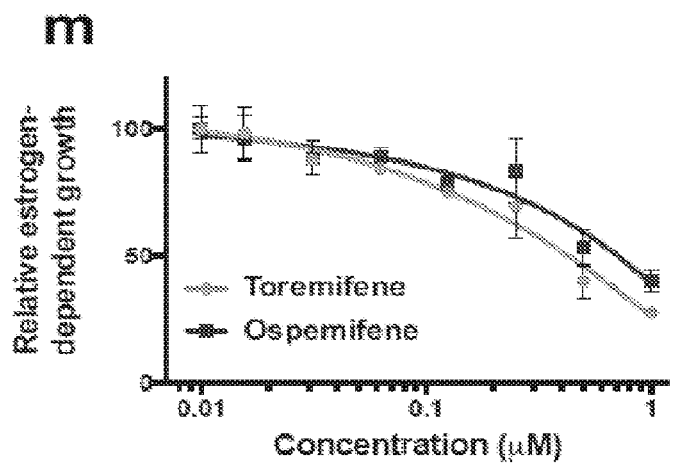

FIGS. 10(A-M) illustrate graphs and images showing the effect of muscarinic receptor antagonists and selective estrogen receptor modulators on cellular EBP function and oligodendrocyte formation. A) Structures of muscarinic receptor antagonists used in this study. B) Percentage of MBP+ oligodendrocytes generated from OPCs at 72 h following treatment with ketoconazole or the indicated muscarinic receptor modulators at 2 µM, the concentration used during screening. n=4 replicates per condition, with >1,000 cells analyzed per replicate. C) Percentage of MBP+ oligodendrocytes generated from a second independent batch of OPCs at 72 h following treatment with ketoconazole or the indicated muscarinic receptor modulators at 2 µM, the concentration used during screening. n=4 replicates per condition, with >1,000 cells analyzed per replicate. D) Heatmap indicating inhibition of muscarinic receptor isoforms M1, M3, and M5 by the indicated small molecules (2 µM) assayed using GeneBLAzer NFAT—bla CHO-K1 cells. n=2 replicates per condition. E) GC/MS-based quantitation of three metabolite levels in OPC-5 OPCs treated 24 h with U50488 (5 µM) or the indicated muscarinic receptor modulators (2 µM). Left, zymostenol; center, cholesterol; right, desmosterol. F) GC/MS-based quantitation of three metabolite levels in OPC-1 OPCs treated 24 h with clemastine (1 µM) or the indicated muscarinic receptor modulators at 2 µM. Left, zymostenol; center, zymosterol; right, cholesterol. G) Structures of two selective estrogen receptor modulators used in this study. H) Percentage of MBP+ oligodendrocytes generated from OPCs at 72 h following treatment with ospemifene and toremifene. n=4 replicates per condition, with >1,000 cells analyzed per replicate. I) Percentage of MBP+ oligodendrocytes generated from a second derivation of OPCs at 72 h following treatment with ospemifene and toremifene. n=4 replicates per condition, with >1,000 cells analyzed per replicate. J) Representative images of OPCs treated 72 h with the indicated small molecules. All molecules were treated at 300 nM. Scale bar, 100 µm. K) GC/MS-based quantitation of two metabolite levels in OPCs treated 24 h with ospemifene and toremifene at 300 nM. Left, zymostenol; right, cholesterol. L) GC/MS-based quantitation of two metabolite levels in a second derivation of OPCs treated 24 h with ospemifene and toremifene at 300 nM. Left, zymostenol; right, cholesterol. M) Effects of ospemifene and toremifene on the estrogen-dependent growth of T47D cells. n=3 replicates per condition. All graphs indicate mean+/−standard deviation.

Figure 11A:
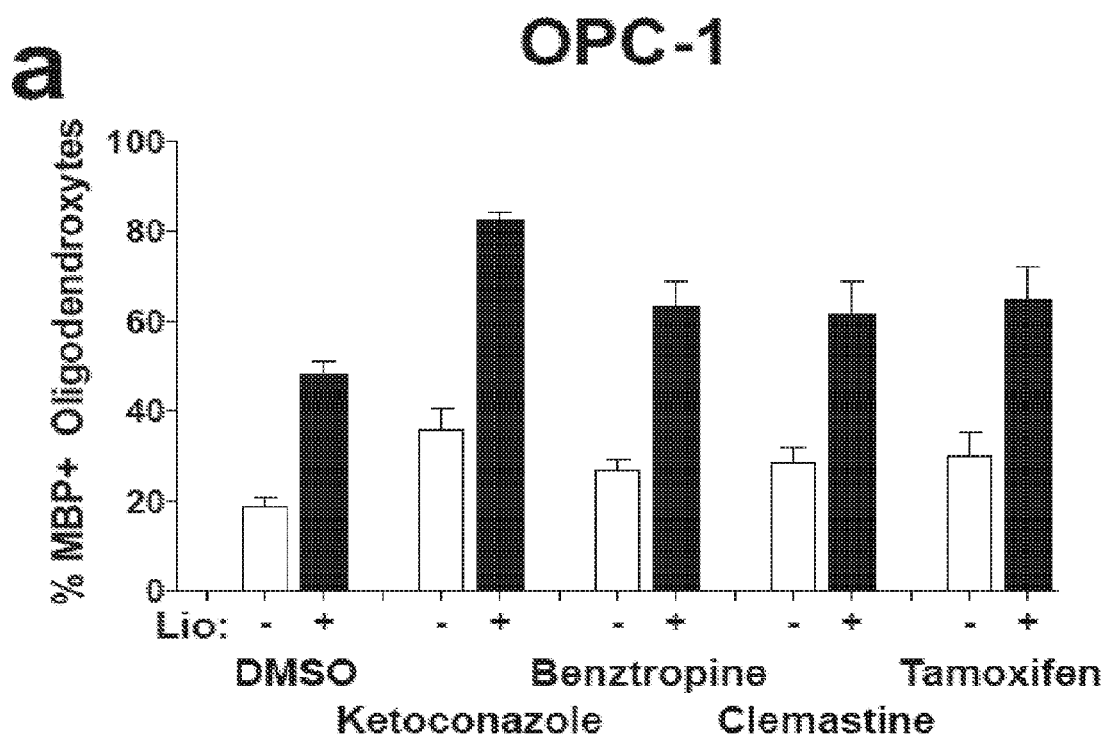
Figure 11D:
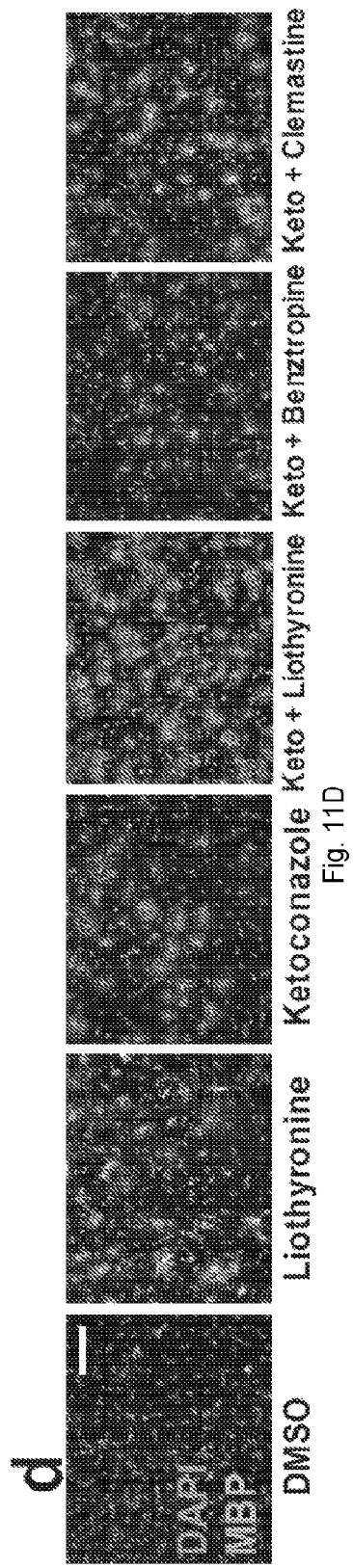

FIGS. 11(A-D) illustrate graphs and images showing the effect of combinations of small-molecule treatments on oligodendrocyte formation. A) Percentage of MBP+oligodendrocytes generated from OPCs at 72 h following treatment with the indicated combinations of liothyronine and enhancers of oligodendrocyte formation. Unless noted, the following concentrations were used: ketoconazole, 2.5 µM; benztropine, 2 µM; clemastine 2 µM; tamoxifen 200 nM; liothyronine, 3 µM. n=4 replicates per treatment condition, with >1,000 cells analyzed per replicate. Lio=liothyronine. B) Percentage of MBP+ oligodendrocytes generated from a second batch of OPCs at 72 h following treatment with the indicated combinations of liothyronine and enhancers of oligodendrocyte formation. n=4 replicates per treatment condition, with >1,000 cells analyzed per replicate. Lio=liothyronine. C) Percentage of MBP+ oligodendrocytes generated from a second, independent derivation of OPCs at 72 h following treatment with the indicated combinations of ketoconazole and enhancers of oligodendrocyte formation. n=4 replicates per treatment condition, with >1,000 cells analyzed per replicate. Keto=ketoconazole. D) Representative images of OPCs treated 72 h with the indicated small molecules. Small molecules concentrations are as in panel a. Scale bar, 100 µm.

FIGS. 12(A-D) illustrate graphs and images showing the effect of sterol-modulating small molecules on oligodendrocytes' ability to track along and wrap electrospun microfibers. A) Fold-increase of MBP+ oligodendrocytes following plating of OPCs onto microfibers and treatment for 14 days with the indicated pathway modulators. n=2. Scale bar, 500 µm. B) Low-magnification images representing the majority of the microfiber area for treatments in panel a. Green, MBP; Blue, DAPI. C) High-resolution images of MBP+ oligodendrocytes tracking along microfibers. Green, MBP; Blue, DAPI. Ketoconazole, 2.5 µM. Scale bar, 50 µm. D) Confocal imaging of OPCs seeded onto aligned microfibers and treated 14 days with ketoconazole (2.5 µM).

FIGS. 13(A-B) illustrate graphs showing the effect of oligodendrocyte-enhancing small molecules on sterol levels in human cells and human cortical spheroids. A) GC/MS-based quantitation of three metabolite levels in human glioma cells (GBM528) treated 24 h with the indicated small molecules at the following concentrations: Tamoxifen, 100 nM, Clemastine 2 µM, Ifenprodil 2 µM, Ketoconazole 2.5 µM, Amorolfine 100 nM. Left, lanosterol; center, zymostenol; right, 14-dehydrozymostenol. n=2 replicates per condition. B) GC/MS-based quantitation of three metabolite levels in two independent batches of human cortical spheroids treated 24 h with the indicated small molecules at 2 µM. Left, lanosterol; center, zymostenol; right, zymosterol. n=3 replicates per condition.

FIG. 14 illustrates the structures of small molecules shown to enhance the formation of oligodendrocytes and to modulate sterol levels in OPCs. Molecules are grouped by enzyme inhibited: CYP51, top; sterol 14-reductase, center; EBP, bottom.

Figure 15:
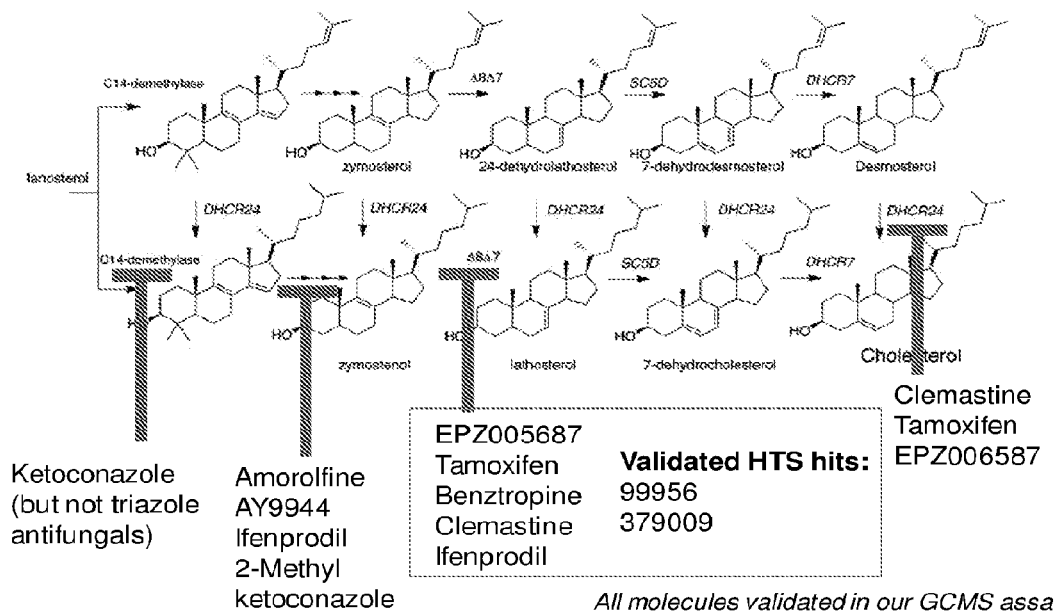

FIG. 15 illustrates hits from bioactive screening validated in GCMS assay inhibit cholesterol synthesis of at least three steps leads to OPC differentiation.

Figure 16:
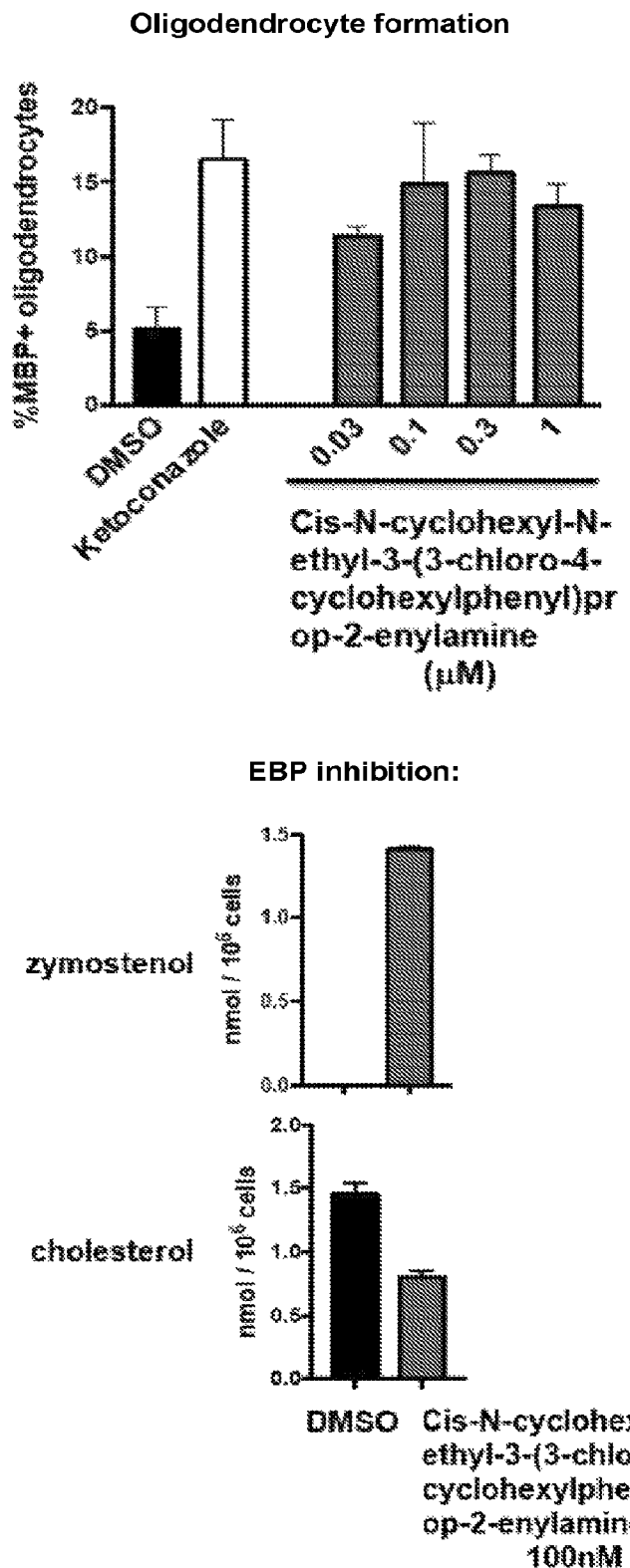

FIG. 16 illustrates graphs showing the effect of the benzene derivative cis-N-cyclohexyl-N-ethyl-3-(3-chloro-4-cyclohexylphenyl)prop-2-enylamine on oligodendrocyte formation and EBP inhibition.

DETAILED DESCRIPTION

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substituents, sulfoxides or sulfinamides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n-1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed agents, in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p 1-92, Elesevier, New York-Oxford (1985).

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

The term "oligodendrocyte precursor cells" or "OPCs" as used herein refers to a neural progenitor cell capable to generate new oligodendrocyte cells. Oligodendrocyte precursor cells can be identified by the expression of a number of surface antigens. For example, the surface antigens known as platelet-derived growth factor-alpha receptor subunit (PDGFRα), NG2 chondroitin sulfate proteoglycan, and ganglioside GD3, are commonly used to identify oligodendrocyte precursor cells.

Immature oligodendrocyte precursors are generated in ventral areas of the developing brain from a common glial progenitor. The immature cells actively migrate, proliferate, and populate the CNS to finally differentiate to premyelinating oligodendrocytes (O4+). Oligodendrocyte precursor differentiation and maturation is characterized by an extension of multiple processes, increase in cell body size and formation of myelin.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal such as, but not limited to, myelination disturbances, myelin deficiencies, myelin loss and ineffective myelin repair) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate.

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano(-CN), isocyano (—$N^+C^-$), cyanato (—O—CN), isocyanato (—$ON^+C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (—$PO_2$), and phosphino (—$PH_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; 6,534,261 and 8,585,526; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; 8,586,526; WO 95/19431; WO 96/06166; WO 98/53057; WO 98/54311; WO 00/27878; WO 01/60970 WO 01/88197, WO 02/099084.

In general, "CRISPRs" (Clustered Regularly Interspaced Short Palindromic Repeats), also known as SPIDRs (SPacer Interspersed Direct Repeats), refer a family of DNA loci that are usually specific to a particular bacterial species. The CRISPR locus comprises a distinct class of interspersed short sequence repeats (SSRs) that were recognized in *E. coli* (Ishino et al. (1987) *J. Bacteriol.*, 169:5429-5433; and Nakata et al., *J. Bacteriol.* (1989) 171:3553-3556), and associated genes. Similar interspersed SSRs have been identified in *Haloferax mediterranei, Streptococcus pyogenes, Anabaena,* and *Mycobacterium tuberculosis* (See, Groenen et al. (1993) *Mol. Microbiol.*, 10:1057-1065; Hoe et al. (1999) *Emerg. Infect. Dis.*, 5:254-263; Masepohl et al. (1996) *Biochim. Biophys. Acta* 1307:26-30; and Mojica et al. (1995) *Mol. Microbiol.*, 17:85-93). The CRISPR loci typically differ from other SSRs by the structure of the repeats, which have been termed short regularly spaced repeats (SRSRs) (Janssen et al. (2002) *OMICS J. Integ. Biol.*, 6:23-33; and Mojica et al. (2000) *Mol. Microbiol.*, 36:244-246). In general, the repeats are short elements that occur in clusters that are regularly spaced by unique intervening sequences with a substantially constant length (Mojica et al. (2000), supra). Although the repeat sequences are highly conserved between strains, the number of interspersed repeats and the sequences of the spacer regions typically differ from strain to strain (van Embden et al., *J. Bacteriol.* (2002) 182:2393-2401). CRISPR loci have been identified in more than 40 prokaryotes including, but not limited to *Aeropyrum, Pyrobaculum, Sulfolobus, Archaeoglobus, Halocarcula, Methanobacteriumn, Methanococcus, Methanosarcina, Methanopyrus, Pyrococcus, Picrophilus, Thernioplasnia, Corynebacterium, Mycobacterium, Streptomyces, Aquifrx, Porphvromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myrococcus, Campylobacter, Wolinella, Acinetobacter, Erwinia, Escherichia, Legionella, Methylococcus, Pasteurella, Photobacterium, Salmonella, Xanthomonas, Yersinia, Treponema,* and *Thermotoga.*

"CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In some embodiments, one or more elements of a CRISPR system is derived from a class 1 type I or type III CRISPR system. In some embodiments, one or more elements of a CRISPR system is derived from a class 2 type II, or type V CRISPR system. In some embodiments, one or more elements of a CRISPR system is derived from a particular organism comprising an endogenous CRISPR system, such as *Streptococcus pyogenes.* In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, a target sequence is located in the nucleus or cytoplasm of a cell. A sequence or template that may be used for recombination into the targeted locus comprising the target sequences is referred to as an "editing template" or "editing polynucleotide" or "editing sequence". In aspects of the invention, an exogenous template polynucleotide may be referred to as an editing template. In an aspect of the invention the recombination is homologous recombination.

"NgAgo" is a prokaryotic Argonaute protein thought to be involved in gene silencing. NgAgo is derived from the archaebacteria *Natronobacterium gregoryi* (See, e.g., Gao et al. (2016) *Nature Biotechnology* 34, 768-773). A "NgAgo system" is all the components required including e.g., single stranded guide DNAs for cleavage by a NgAgo enzyme.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

Embodiments described herein generally relate to agents, compounds, and methods for enhancing oligodendrocyte generation by inducing, promoting, and/or modulating oligodendrocyte precursor cell differentiation, proliferation and/or maturation as well as to methods for the treatment of disease or disorders in subjects where myelination or remyelination is beneficial to the subject.

It was found that the enhancement and/or inducement of the accumulation of Δ8,9-unsaturated sterol intermediates of the cholesterol biosynthesis pathway in oligodendrocyte progenitor cells (OPCs) can induce Oligodendrocyte generation. Enhancement and/or inducement of the accumulation of Δ8,9-unsaturated sterol intermediates can be provided by modulating and/or inhibiting enzymes within the cholesterol biosynthesis pathway in OPCs that inhibit Δ8,9-unsaturated sterol intermediate accumulation and/or for which the Δ8,9-unsaturated sterol intermediates are substrates as well as directly and/or indirectly administering Δ8,9-unsaturated sterol intermediates to the OPCs. Enhancement and/or inducement of the accumulation of Δ8,9-unsaturated sterol intermediates can promote OPC differentiation, survival, proliferation and/or maturation and treat disease and/or disorders in subjects where myelination or remyelination is beneficial to the subject.

In some embodiments, an agent that enhances and/or induces accumulation of Δ8,9-unsaturated sterol intermediates of the cholesterol biosynthesis pathway in the OPCs can be administered to a subject and/or the OPCs at an amount effective to promote and/or induce OPC differentiation, proliferation and/or maturation as well as oligodendrocyte generation. In one example, the agent can include at least one compound that inhibits enzyme mediated synthesis of one or more sterol intermediates in the cholesterol biosynthesis pathway of the OPCs and/or promotes accumulation of Δ8,9-unsaturated sterol intermediates.

In some embodiments, the compound can modulate and/or inhibit one or more enzyme mediated conversion steps of the cholesterol biosynthesis pathway from lanosterol to cholesterol, for example, between lanosterol and/or lathosterol, of OPCs to promote and/or induce oligodendrocyte generation. For example, the compound can inhibit CYP51, sterol 14-reductase, and/or EBP enzyme mediated synthesis of sterol intermediates in the cholesterol biosynthesis pathway. In yet another example, the compound can modulate and/or inhibit enzyme mediated conversion of lanosterol to 4,4-dimethylcholesta-8(9),14,24-trien-3β-ol, 4,4-dimethylcholesta-8(9),14,24-trien-3β-ol to zymostenol, and/or zymostenol to lathosterol to enhance oligodendrocyte generation.

In some embodiments, the compound can modulate and/or inhibit one or more enzyme mediated conversion steps of the cholesterol biosynthesis pathway from lanosterol to dehydrolathosterol or lathosterol.

In some embodiments, a compound used in the methods described herein can inhibit enzyme mediated conversion of zymostenol to lathosterol through the inhibition of emopamil binding protein (EBP) isomerase enzyme activity. Alternatively, a compound used in the methods described herein can inhibit sterol C14 reductase enzyme activity or CYP51 enzyme activity in the cholesterol biosynthesis pathway.

Compounds that are capable of enhancing oligodendrocyte generation by OPC differentiation via modulation and/or inhibition of the cholesterol biosynthesis pathway can be identified by measuring levels of cholesterol and upstream metabolites in OPCs administered the screened compounds. In some embodiments, compounds, which are capable of enhancing OPC differentiation via modulation and/or inhibition of the cholesterol biosynthesis pathway can be identified using a high-throughput small molecule screen (HTS) that is biased to select compounds that have both a high potency and low toxicity in mammal subjects and are able to promote oligodendrocyte precursor differentiation. The term "small molecule" as used herein refers to biologically active organic compounds of low molecular weight (e.g. <550 kDa) which may cross biological membranes and modulate intracellular processes.

The HTS can include a primary screen where small drug-like organic compounds (250-550 kDa) are added to cells seeded and incubated on a 96- or 384-well plate. The cells can then be visually screened for oligodendrocyte precursor morphology changes. In a secondary screen, differentiation and proliferation induced by selected compounds can be further validated by fluorescence microscopy. Further oligodendrocyte precursor proliferation and maturation in response to selected compounds can then be assessed by induction of myelin protein expression as determined by, for example, immunocytochemistry and western blot. Examples of assays that can be used in the primary and secondary screening are described in Najm et al. Nat Methods. 2011 Sep. 25; 8(11):957-62; Bai et al. Neurosci Bull. 2013 April; 29(2):239-50; Yang et al. Dev Biol. 2011 Feb. 1; 350(1):127-38; and Cho et al. Curr Neuropharmacol. 2007 March; 5(1): 19-33.

Compounds can be further screened using a GCMS assay to monitor levels of cholesterol and intermediates en route to cholesterol, including squalene, squalene epoxide, lanosterol, FF-MAS, T-MAS, other meiosis activating sterols, zymosterol, zymostenol, lathosterol, dehydrolathosterol dehydrodesmosterol, desmosterol, 7-DHC, 8-DHC, and others. Such assays are described in Korade et al. J. Med. Chem., 2016 59 (3), 1102-1115, among others. Briefly, cells can be treated with various molecules and then lysed using an organic solvent, such as methanol or chloroform to extract lipophilic metabolites. Following silylation using BTMSA or an equivalent silylating reagent, samples are injected onto the GC-MS and sterol abundance is determined by comparison of integrated peak intensities to genuine sterol reference standards.

In some embodiments, the compounds can be further screened using a brain slice assay that assesses myelination the brains of mammals, (e.g., rats and mice). Such assays are described, for example, in Bai et al. Neurosci Bull. 2013 April; 29(2):239-50, Yang et al. Dev Biol. 2011 Feb. 1; 350(1):127-38, and Cho et al. Curr Neuropharmacol. 2007 March; 5(1): 19-33.

In other embodiments, the compounds can be screened using an in vivo assay that assesses remyelination and reduction of clinical severity in the MOG35-55-induced chronic experimental autoimmune encephalomyelitis (EAE) rodent model of multiple sclerosis.

In other embodiments, the compounds can be screened using an assay that assesses myelination in vivo in a lysolecithin-induced mouse model of focal demyelination. Such an assay is described, for example, in Mi, S et al., Ann Neurol 65, 304-325 (2009).

In certain embodiments, compounds identified that are capable of enhancing OPC differentiation can modulate and/or inhibit the enzyme mediated synthesis of one or more sterol intermediates in the cholesterol biosynthesis pathway of OPCs (See for example, FIG. 15). In some embodiments, the compounds can modulate and/or inhibit the enzyme mediated synthesis of one or more sterol intermediates in the cholesterol biosynthesis pathway of OPCs at an amount effective to promote and/or induce oligodendrocyte precursor cell differentiation, proliferation and/or maturation. For example, the compounds can inhibit the enzyme mediated synthesis of one or more sterol intermediates in the cholesterol biosynthesis pathway of OPCs by at least 5%, 10%, 20%, 25%, 30%, 40%, 50%, 60%, 70%, 75%, 80%, 85%, 90%, 95%, or 99% as compared to the amount of enzyme mediated synthesis of one or more sterol intermediates in the cholesterol biosynthesis pathway in untreated OPCs or subject.

It has been shown that inhibiting cholesterol biosynthesis at steps upstream of the sterol intermediate lanosterol has little-to-no effect on OPC differentiation. Therefore, in some embodiments, compounds identified by the OPC HTS and GCMS can include compounds capable of modulating and/or inhibiting one or more enzyme mediated conversion steps of the cholesterol biosynthesis pathway from lanosterol to cholesterol and/or between lanosterol and lathosterol at an amount effective to promote and/or induce oligodendrocyte precursor cell differentiation, proliferation and/or maturation. For example, the compounds can inhibit one or more enzyme mediated conversion steps of the cholesterol biosynthesis pathway from lanosterol to cholesterol and/or between lanosterol and lathosterol by at least 5%, 10%, 20%, 25%, 30%, 40%, 50%, 60%, 70%, 75%, 80%, 85%, 90%, 95%, or 99% as compared to the amount of enzyme mediated synthesis of one or more sterol intermediates in the cholesterol biosynthesis pathway from lanosterol to cholesterol in untreated OPCs or subject.

In certain embodiments, compounds identified by the OPC HTS screen and GCMS can include compounds capable of modulating and/or inhibiting enzyme mediated conversion of lanosterol to FF-MAS, FF-MAS to T-MAS, zymostenol to lathosterol, T-MAS to zymosterol, zymosterol to dehydrolathosterol and/or desmosterol to cholesterol in the cholesterol biosynthesis pathway at an amount effective to promote and/or induce oligodendrocyte precursor cell differentiation, proliferation and/or maturation. For example, the compounds can inhibit enzyme mediated conversion of lanosterol to FF-MAS, FF-MAS to T-MAS, zymostenol to lathosterol, T-MAS to zymosterol, zymosterol to dehydrolathosterol, and/or desmosterol to cholesterol in the cholesterol biosynthesis pathway by at least 5%, 10%, 20%, 25%, 30%, 40%, 50%, 60%, 70%, 75%, 80%, 85%, 90%, 95%, or 99% as compared to the amount of enzyme mediated conversion of lanosterol to FF-MAS, FF-MAS to T-MAS, zymostenol to lathosterol, T-MAS to zymosterol, zymosterol to dehydrolathosterol, and/or desmosterol to cholesterol in untreated OPCs or subject. Examples of compounds that can inhibit enzyme mediated conversion of lanosterol to FF-MAS, FF-MAS to T-MAS, zymostenol to lathosterol, T-MAS to zymosterol, zymosterol to dehydrolathosterol, and/or desmosterol to cholesterol in the cholesterol biosynthesis pathway include ketoconazole, 2-Methyl ketoconazole, Amorolfine, AY9944, EPZ005687, Tamoxifen, Benztropine, Bexarotene, Clemastine, FR171456, cis-N-cyclohexyl-N-ethyl-3-(3-chloro-4-cyclohexylphenyl)prop-2-enylamine and Ifenprodil.

In some embodiments, the compounds are capable of modulating and/or inhibiting enzyme (e.g., emopamil binding protein) mediated conversion of zymostenol to lathosterol. Emopamil binding protein (EBP, also referred to as A8A7 isomerase, 3-beta-hydroxysteroid-Delta(8),Delta(7)-isomerase, CDPX2, CHO2, CPX, or CPXD) is an enzyme responsible for one of the final steps in the production of cholesterol. Specifically, it converts zymostenol to lathosterol, where other enzymes then modify lathosterol to produce cholesterol (see for example FIG. 15). Thus, in some embodiments, compounds that are capable of inhibiting EBP mediated conversion of zymostenol to lathosterol in the cholesterol biosynthesis pathway of OPCs can promote and/or induce oligodendrocyte precursor cell differentiation, proliferation and/or maturation. For example, the compounds can inhibit EBP mediated enzymatic conversion of zymostenol to lathosterol in the cholesterol biosynthesis pathway by at least 5%, 10%, 20%, 25%, 30%, 40%, 50%, 60%, 70%, 75%, 80%, 85%, 90%, 95%, or 99% as compared to the amount of EBP mediated conversion of desmosterol to cholesterol in untreated OPCs or subject.

In some embodiments, EBP inhibiting compounds used in the methods described herein can have the formula (I):

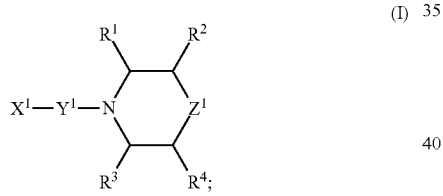

(I)

where (a) $X^1$ is substituted or unsubstituted aryl, heteroaryl, cyclyl or heterocyclyl;
(b) $Y^1$ is a substituted or unsubstituted $C_1$-$C_6$ straight chain or branched alkyl;
(c) $Z^1$ is CR'R", NR' or OR'; and
(d) R', R", $R^1$, $R^2$, $R^3$, or $R^4$ are each independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfonyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH2, —SO$_2$NY$_2$ (wherein Y is independently H, arlyl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incorporating amino acids or other moieties expected to bear positive or negative charge at physiological pH, combinations thereof, and wherein R' and R" may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl.

In some embodiments, compounds having Formula (I) can include compounds having the Formula (II):

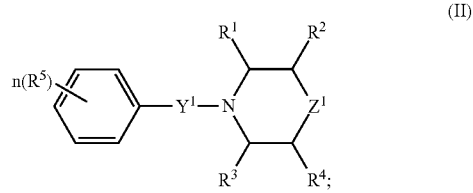

(II)

where (a) $Y^1$ is a substituted or unsubstituted $C_1$-$C_6$ straight chain or branched alkyl;
(b) $Z^1$ is CR'R", NR' or OR';
(c) R', R", $R^1$, $R^2$, $R^3$, $R^4$ and $R^5$ are each independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{21}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), C$_1$-C$_{24}$ alkyl amino, C$_5$-C$_{20}$ aryl amino, C$_2$-C$_{24}$ alkylamido (—NH—(CO)-alkyl), C$_6$-C$_{20}$ arylamido (—NH—(CO)-aryl), imino (—CR=NH where R is hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo sulfonato (—SO$_2$—OH), C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), sulfonamide (—SO$_2$—NH2, —SO$_2$NY$_2$ (wherein Y is independently H, arlyl or alkyl), phosphono (—P(O)(OH)$_2$), phosphonato (—P(O)(O$^-$)$_2$), phosphinato (—P(O)(O$^-$)), phospho (—PO$_2$), phosphino (—PO$_2$), polyalkylethers, phosphates, phosphate esters, groups incorporating amino acids or other moieties expected to bear positive or negative charge at physiological pH, combinations thereof, and wherein R' and R" may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl; and (d) where n is 1-5.

In other embodiments, compounds having Formula (I) can include compounds having the Formula (IIIa):

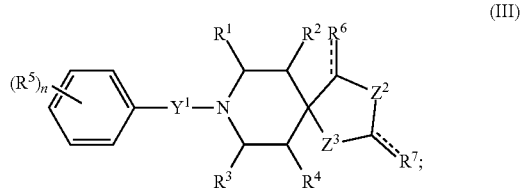

(III)

where (a) Y$^1$ is a substituted or unsubstituted C$_1$-C$_6$ straight chain or branched alkyl;

(b) Z$^2$ and Z$^3$ are each independently selected from the group consisting of NR' or (CHR')n$_1$, wherein either Z$^2$ or Z$^3$ is NR';

(c) R', R', R$^2$, R$^3$, R$^4$, R$^5$, R$^6$, R$^7$ are each independently selected from the group consisting of hydrogen, oxygen, substituted or unsubstituted C$_1$-C$_{24}$ alkyl, C$_2$-C$_{24}$ alkenyl, C$_2$-C$_{24}$ alkynyl, C$_3$-C$_{20}$ aryl, heteroaryl, heterocycloalkenyl containing from 5-6 ring atoms (wherein from 1-3 of the ring atoms is independently selected from N, NH, N(C$_1$-C$_6$ alkyl), NC(O)(C$_1$-C$_6$ alkyl), O, and S), C$_6$-C$_{24}$ alkaryl, C$_6$-C$_{24}$ aralkyl, halo, —Si(C$_1$-C$_3$ alkyl)$_3$, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl (including C$_2$-C$_{24}$ alkylcarbonyl (—CO-alkyl) and C$_6$-C$_{20}$ arylcarbonyl (—CO-aryl)), acyloxy (—O-acyl), C$_2$-C$_{24}$ alkoxycarbonyl (—(CO)—O-alkyl), C$_6$-C$_{20}$ aryloxycarbonyl (—(CO)—O-aryl), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COO$^-$), carbamoyl (—(CO)—NH$_2$), C$_1$-C$_{24}$ alkyl-carbamoyl (—(CO)—NH(C$_1$-C$_{24}$ alkyl)), arylcarbamoyl (—(CO)—NH-aryl), thiocarbamoyl (—(CS)—NH$_2$), carbamido (—NH—(CO)—NH$_2$), cyano(-CN), isocyano (—N$^+$C$^-$), cyanato (—O—CN), isocyanate isothiocyanato (—S—CN), azido (—N=N$^+$=N$^-$), formyl thioformyl (—(CS)—H), amino (—NH$_2$), C$_1$-C$_{24}$ alkyl amino, C$_5$-C$_{10}$ aryl amino, C$_2$-C$_{24}$ alkylamido (—NH—(CO)-alkyl), C$_6$-C$_{20}$ arylamido (—NH—(CO)-aryl), imino (—CR=NH where R is hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR=N(alkyl), where R=hydrogen, alkyl, aryl, alkaryl, aralkyl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), C$_1$-C$_{24}$ alkylsulfanyl (—S-alkyl; also termed "alkylthio"), arylsulfinyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), sulfonamide (—SO$_2$—NH2, —SO$_2$NY$_2$ (wherein Y is independently H, arlyl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incorporating amino acids or other moieties expected to bear positive or negative charge at physiological pH, combinations thereof;

(d) where n is 1-5 and n$_1$ is 1-4; and (e) dashed lines are taken at each occurrence independently to be double or single bonds.

In still other embodiments, compounds having Formula (I) can include compounds having the Formula (IIIb):

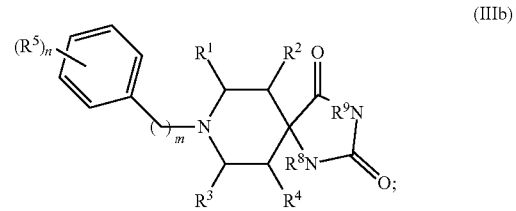

(IIIb)

where (a); R$^1$, R$^2$, R$^3$, R$^4$, R$^5$, R$^8$, and R$^9$ are each independently selected from the group consisting of hydrogen, substituted or unsubstituted C$_1$-C$_{24}$ alkyl, C$_2$-C$_{24}$ alkenyl, C$_2$-C$_{24}$ alkynyl, C$_3$-C$_{20}$ aryl, heteroaryl, heterocycloalkenyl containing from 5-6 ring atoms (wherein from 1-3 of the ring atoms is independently selected from N, NH, N(C$_1$-C$_6$ alkyl), NC(O) (C$_1$-C$_6$ alkyl), O, and S), C$_6$-C$_{24}$ alkaryl, C$_6$-C$_{24}$ aralkyl, halo, —Si(C$_1$-C$_3$ alkyl)$_3$, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl (including C$_2$-C$_{24}$ alkylcarbonyl (—CO-alkyl) and C$_6$-C$_{20}$ arylcarbonyl (—CO-aryl)), acyloxy (—O-acyl), C$_2$-C$_{24}$ alkoxycarbonyl (—(CO)—O-alkyl), C$_6$-C$_{20}$ aryloxycarbonyl (—(CO)—O-aryl), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COM, carbamoyl (—(CO)—NH$_2$), C$_1$-C$_{24}$ alkyl-carbamoyl (—(CO)—NH(C$_1$-C$_{24}$ alkyl)), arylcarbamoyl (—(CO)—NH-aryl), thiocarbamoyl (—(CS)—NH$_2$), carbamido (—NH—(CO)—NH$_2$), cyano(-CN), isocyano (—N$^+$C$^-$), cyanato (—O—CN), isocyanato (—O—N$^+$=C$^-$), isothiocyanato (—S—CN), azido (—N═N⁺═N⁻), formyl thioformyl (—(CS)—H), amino (—NH₂), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR═NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR═N(alkyl), where R═hydrogen, alkyl, aryl, alkaryl, aralkyl, etc.), arylimino (—CR═N(aryl), where R═hydrogen, alkyl, aryl, alkaryl, etc.), nitro (—NO₂), nitroso (—NO), sulfo (—SO₂—OH), sulfonato (—SO₂—O⁻), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO₂-alkyl), $C_5$-$C_{20}$ arylsulfonyl (—SO₂-aryl), sulfonamide (—SO₂—NH2, —SO₂NY₂ (wherein Y is independently H, arlyl or alkyl), phosphono (—P(O)(OH)₂), phosphonato (—P(O)(O⁻)₂), phosphinato (—P(O)(O⁻)), phospho (—PO₂), phosphino (—PH₂), polyalkylethers, phosphates, phosphate esters, groups incorporating amino acids or other moieties expected to bear positive or negative charge at physiological pH, combinations thereof; and (b) n is 1-5 and m is 1-3.

An example of compound of Formula (I) has the following formula:

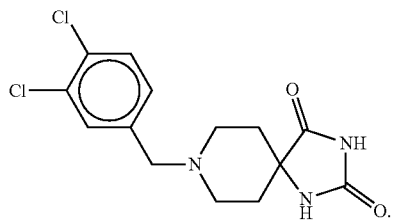

Other embodiments of compounds having Formula (I) include compounds having Formula (IVa):

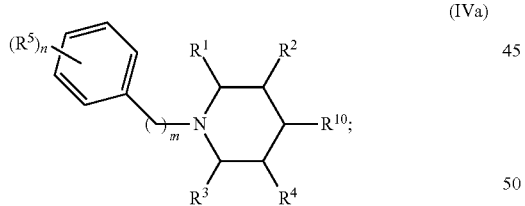

(IVa)

where (a); $R^1$, $R^2$, $R^3$, $R^4$, $R^5$, and $R^{10}$ are each independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)₃, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH₂), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH₂), carbamido (—NH—(CO)—NH₂), cyano(-CN), isocyano (—N⁺C⁻), cyanato (—O—CN), isocyanato (—O—N⁺═C⁻), isothiocyanato (—S—CN), azido (—N═N⁺═N⁻), formyl (—(CO)—H), thioformyl (—(CS)—H), amino (—NH₂), $C_1$-$C_{24}$ alkyl amino, $C_5$-$C_{20}$ aryl amino, $C_2$-$C_{24}$ alkylamido (—NH—(CO)-alkyl), $C_5$-$C_{20}$ arylamido (—NH—(CO)-aryl), imino (—CR═NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR═N(alkyl), where R═hydrogen, alkyl, aryl, alkaryl, aralkyl, etc.), arylimino (—CR═N(aryl), where R═hydrogen, alkyl, aryl, alkaryl, etc.), nitro (—NO₂), nitroso (—NO), sulfo (—SO₂—OH), sulfonato (—SO₂—O⁻), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO₂-alkyl), $C_5$-$C_{20}$ arylsulfonyl (—SO₂-aryl), sulfonamide (—SO₂—NH2, —SO₂NY₂ (wherein Y is independently H, allyl or alkyl), phosphono (—P(O)(OH)₂), phosphonato (—P(O)(O⁻)₂), phosphinato (—P(O)(O⁻)), phospho (—PO₂), phosphino (—PH₂), polyalkylethers, phosphates, phosphate esters, groups incorporating amino acids or other moieties expected to bear positive or negative charge at physiological pH, combinations thereof; and (b) n is 1-5 and m is 1-3.

Still other embodiments of compounds having Formula (I) include compounds having the Formula (IVb):

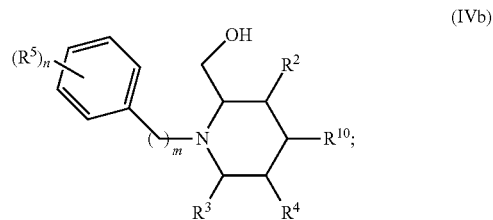

(IVb)

where (a); $R^2$, $R^3$, $R^4$, $R^5$, and $R^{10}$ are each independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), 0, and S), $C_6$-$C_{24}$ alkaryl, $C_6$-$C_{24}$ aralkyl, halo, —Si($C_1$-$C_3$ alkyl)₃, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ acyloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH₂), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH₂), carbamido (—NH—(CO)—NH₂), cyano(-CN), isocyano (—N⁺C⁻), cyanato (—O—CN), isocyanato (—O—N⁺≡C⁻), isothiocyanato (—S—CN), azido (—N=N⁺=N⁻), formyl (—(CO)—H), thioformyl (—(CS)—H), amino (—NH₂), C₁-C₂₄ alkyl amino, C₅-C₂₀ aryl amino, C₂-C₂₄ alkylamido (—NH—(CO)-alkyl), C₆-C₂₀ arylamido (—NH—(CO)-aryl), imino (—CR=NH where R is hydrogen, C₁-C₂₄ alkyl, C₅-C₂₀ aryl, C₆-C₂₄ alkaryl, C₆-C₂₄ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO₂), nitroso (—NO), sulfo (—SO₂—OH), sulfonato (—SO₂—O⁻), C₁-C₂₄ alkylsulfanyl (—S-alkyl; also termed "alkylthio"), arylsulfanyl (—S-aryl; also termed "arylthio"), C₁-C₂₄ alkylsulfinyl (—(SO)-alkyl), C₅-C₂₀ arylsulfinyl (—(SO)-aryl), C₁-C₂₄ alkylsulfonyl (—SO₂-alkyl), C₅-C₂₀ arylsulfonyl (—SO₂-aryl), sulfonamide (—SO₂—NH2, —SO₂NY₂ (wherein Y is independently H, arlyl or alkyl), phosphono (—P(O)(OH)₂), phosphonato (—P(O)(O⁻)₂), phosphinato (—P(O)(O⁻)), phospho (—PO₂), phosphino (—PH₂), polyalkylethers, phosphates, phosphate esters, groups incorporating amino acids or other moieties expected to bear positive or negative charge at physiological pH, combinations thereof; and (b) n is 1-5 and m is 1-3.

An example of compound of Formula (I) has the following formula:

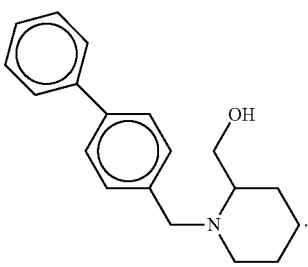

In some aspects, EBP inhibiting compounds identified by the OPC screen and/or GCMS for use in a method described herein can include EPZ005687, Tamoxifen, Benztropine, Clemastine, and Ifenprodil.

Additional examples of EBP inhibiting compounds for use in methods described herein can include:

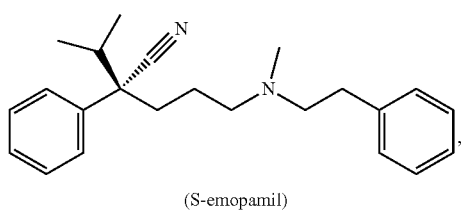

(S-emopamil)

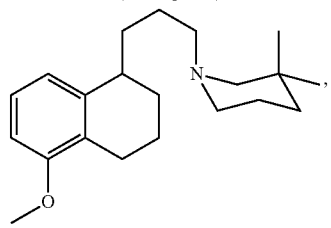

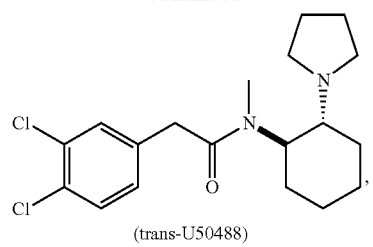

(trans-U50488)

hydroxyzine, p-Fluorohexahydro-Siladifenidol, enclomiphene, raloxifene, nafoxidine, Levormeloxifene, clomiphene, toremifene, raloxifene, bazedoxifene, lasofoxifene, perphenazine, fluphenazine, trifluoperazine, prochlorperazine, hydrazine, triparanol, droloxifene, idoxifen, mixproxifene (TAT 59), clozapine, pramoxine, TMB-8, vesamicol, difenidol analogs, L-745,870, 7-keto-cholesterol, and 7-hydroxy-cholesterol.

In other embodiments, EBP inhibiting compounds for use in the methods described herein can include benzene derivative compounds. Benzene derivatives for use in a method described herein include those described, for example, in U.S. Pat. No. 5,354,781, the subject matter of which is incorporated herein by reference in its entirety. Such benzene derivative compounds can have the general formula:

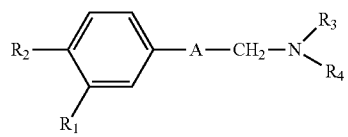

in which: R₁ is hydrogen or a halogen atom;

R₂ is a cyclohexyl or a phenyl;

R₃ is a (C₃-C₆) cycloalkyl;

R₄ is hydrogen, (C₁-C₆) alkyl or (C₃-C₆) cycloalkyl;

A is —CO—CH₂—, —CH(Cl)—CH₂—, —CH(OH)—CH₂—, —CH=CH— and or a pharmaceutical salt thereof.

In some embodiments, the benzene derivative can include a small molecule having the formula

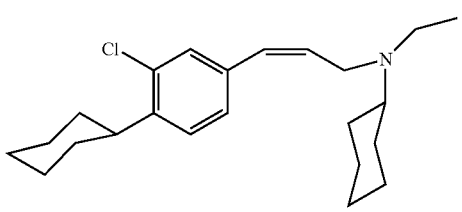 [SMILES: CCN(C/C=C\c1ccc(C2CCCCC2)c(Cl)c1)C1CCCCC1]

cis-N-cyclohexyl-N-ethyl-3-(3-chloro-4-cyclohexylphenyl) prop-2-enylamine), as well as analogs, derivatives and pharmaceutical salts thereof.

In some embodiments, the EBP inhibiting compounds for use in a method described herein can include cis and trans isomers of compounds having the formulas:

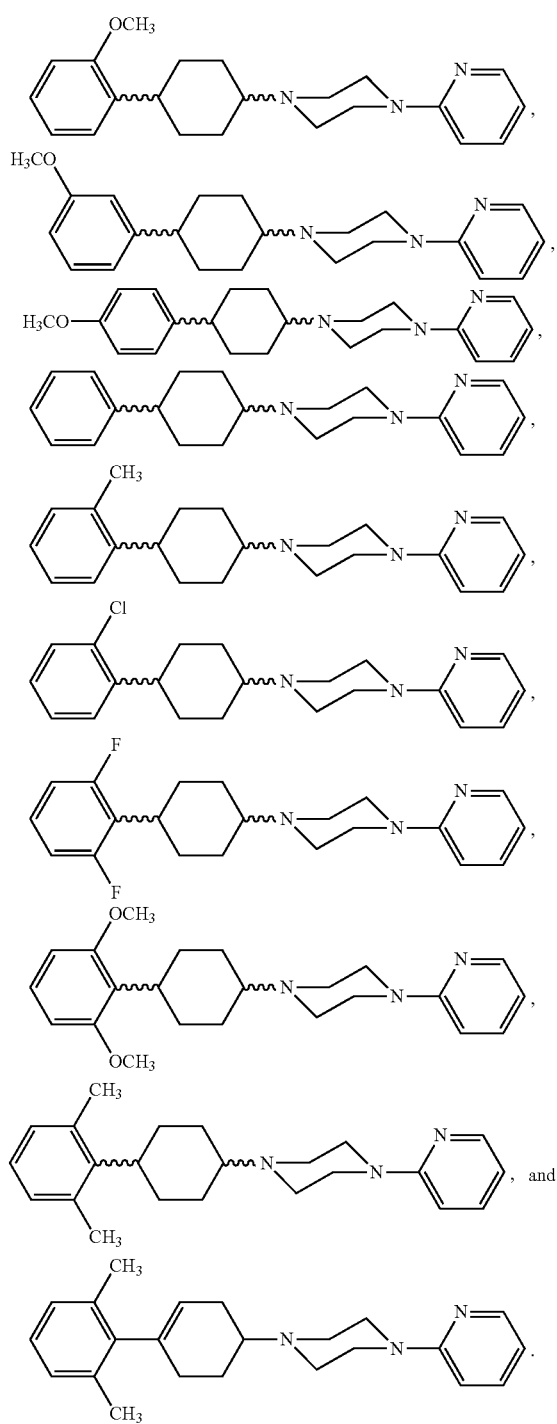
In a particular embodiment, the EBP inhibiting compounds for use in a method described herein can include cis isomers of compounds having the formulas:
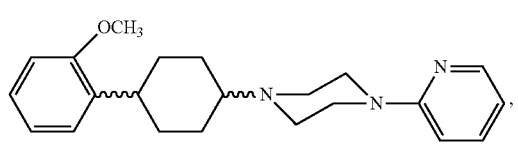
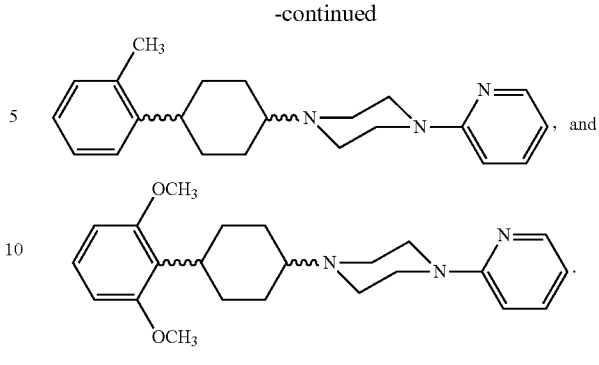
EBP inhibiting compounds for use in a method described herein can also include:
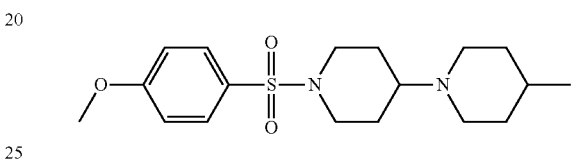
Tasin-1) and analogs thereof.
Examples of Tasin-1 analogs include compounds having the formulas:
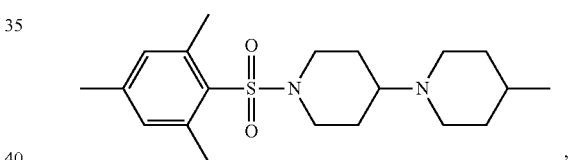
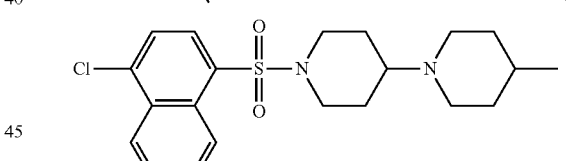
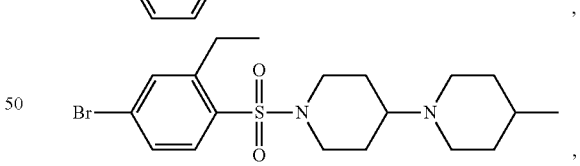
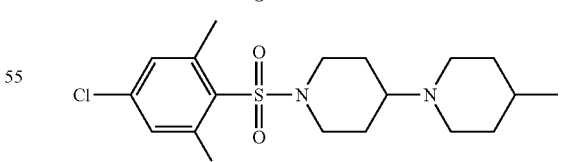
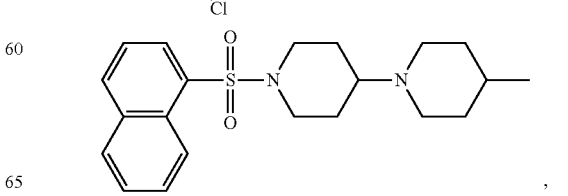

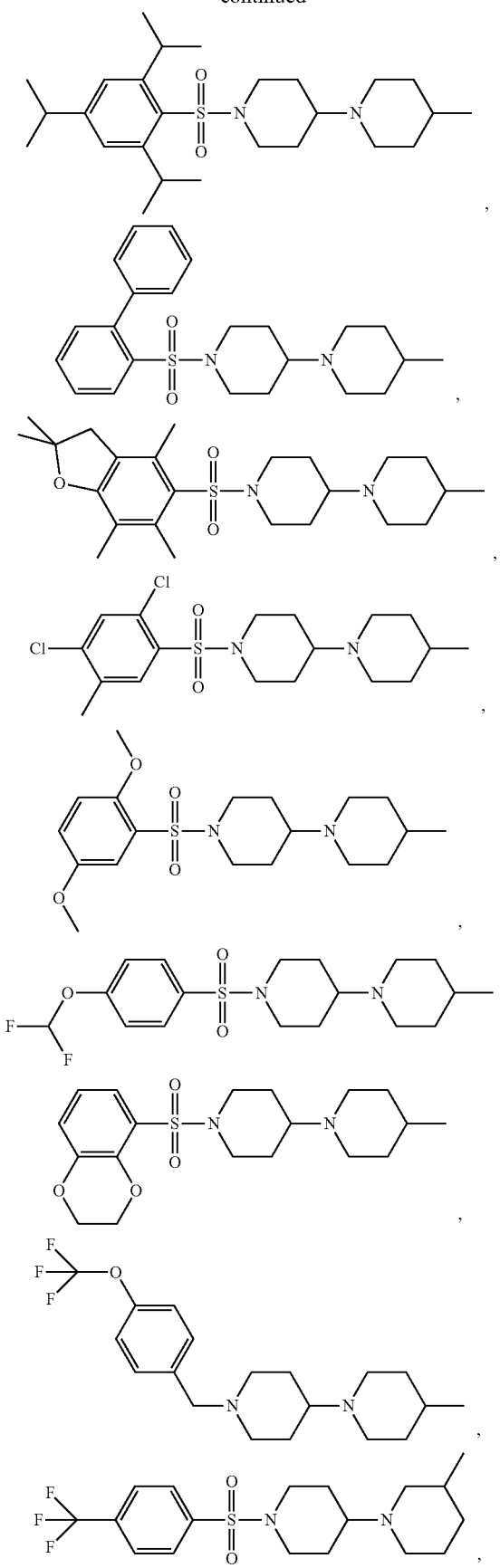
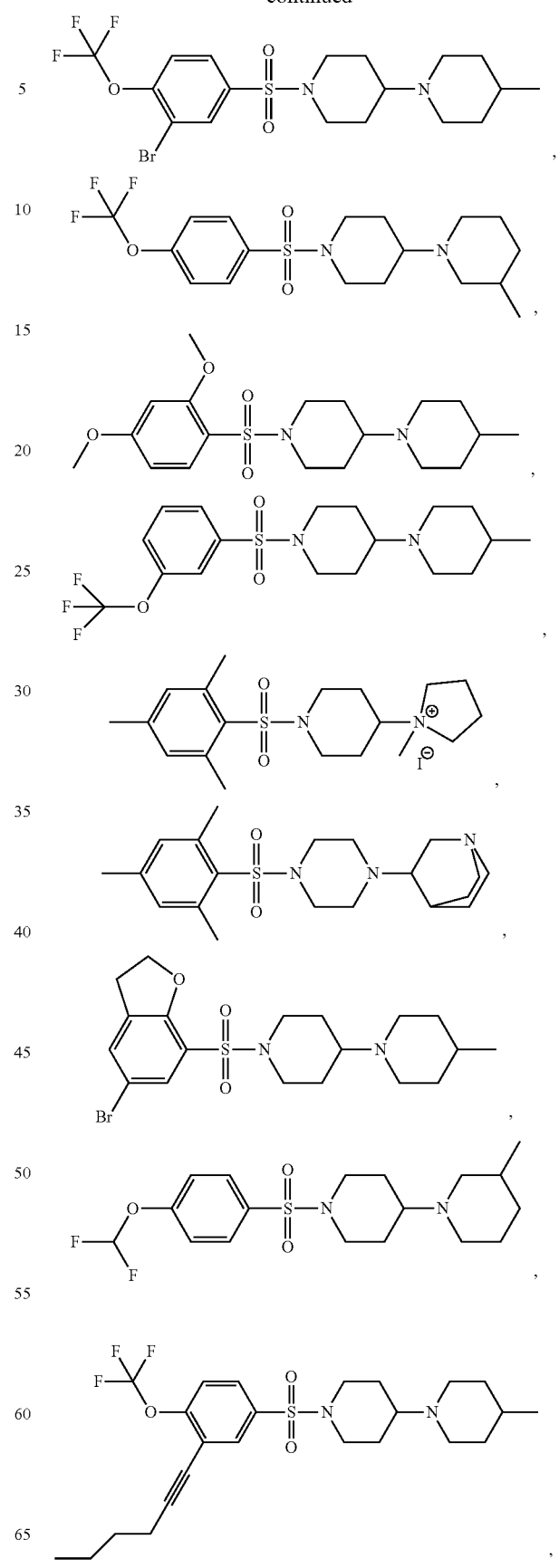

-continued
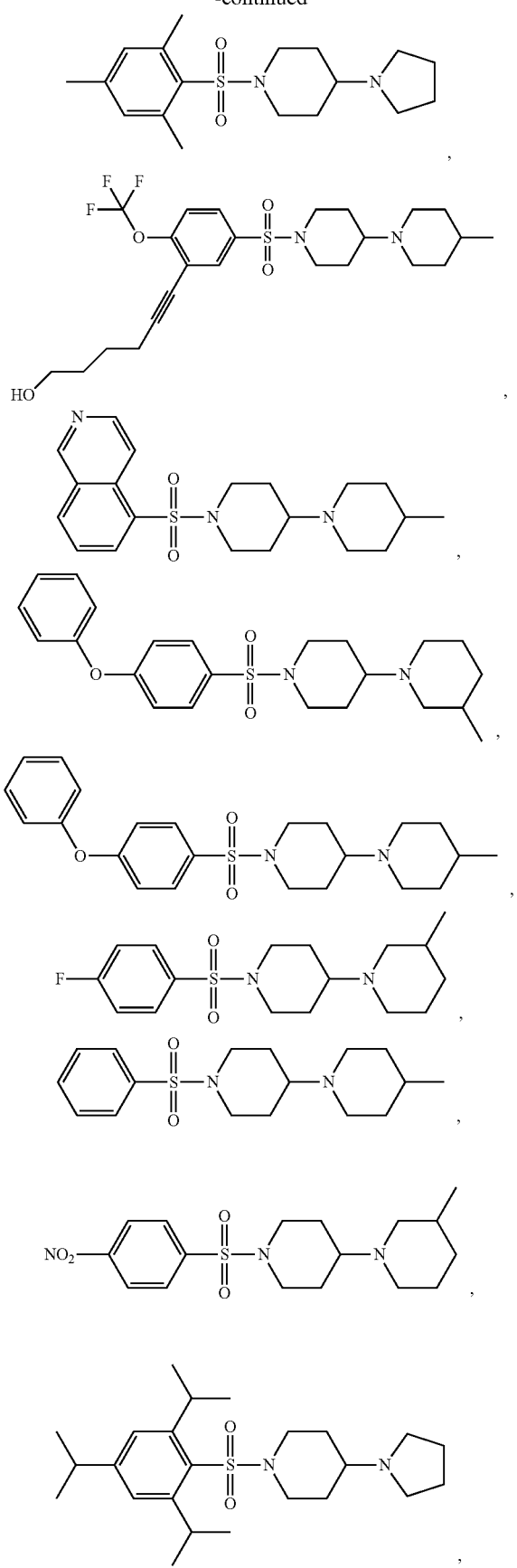
,
-continued
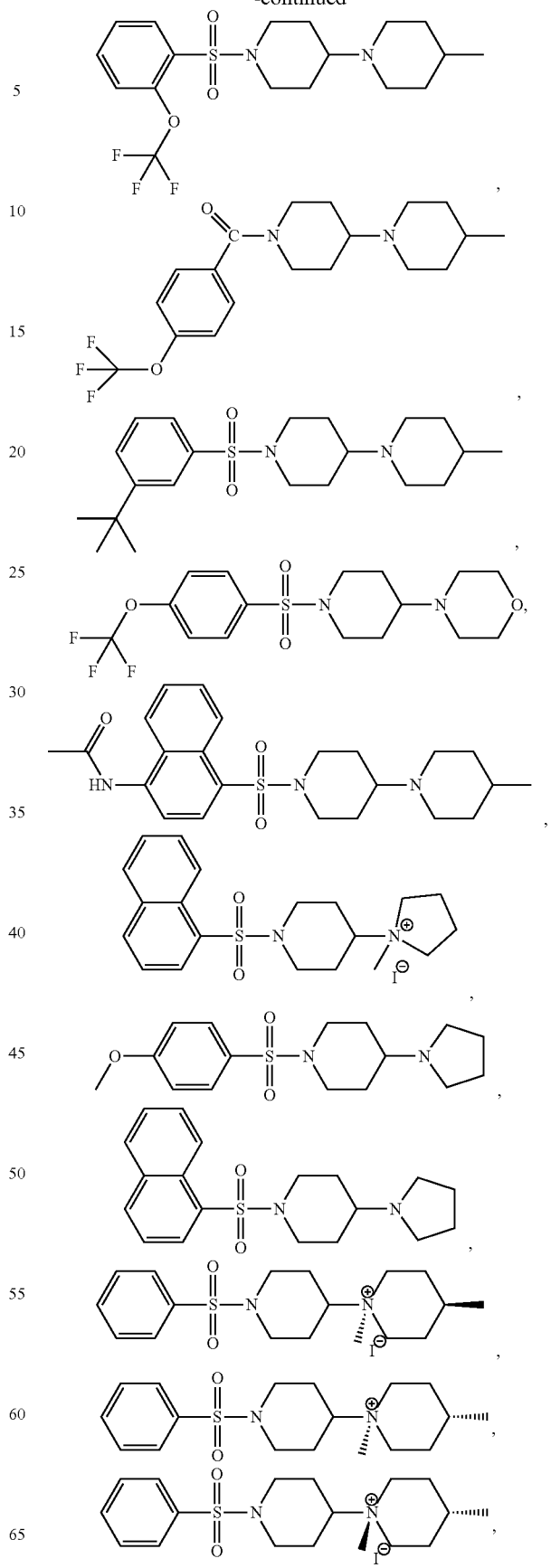

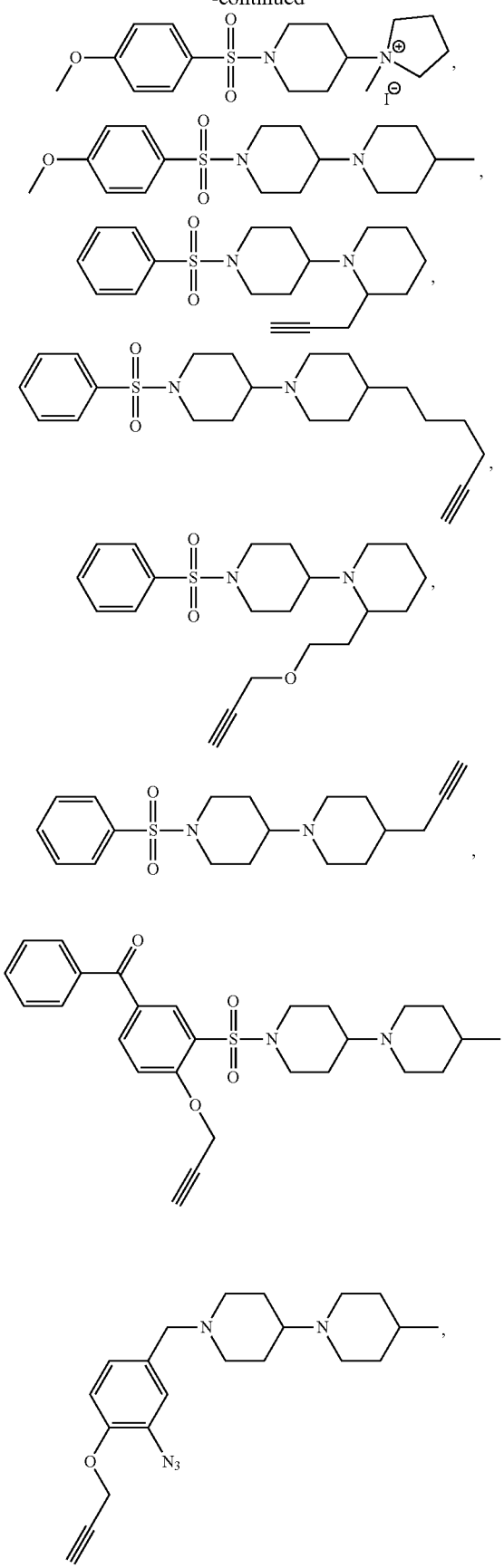
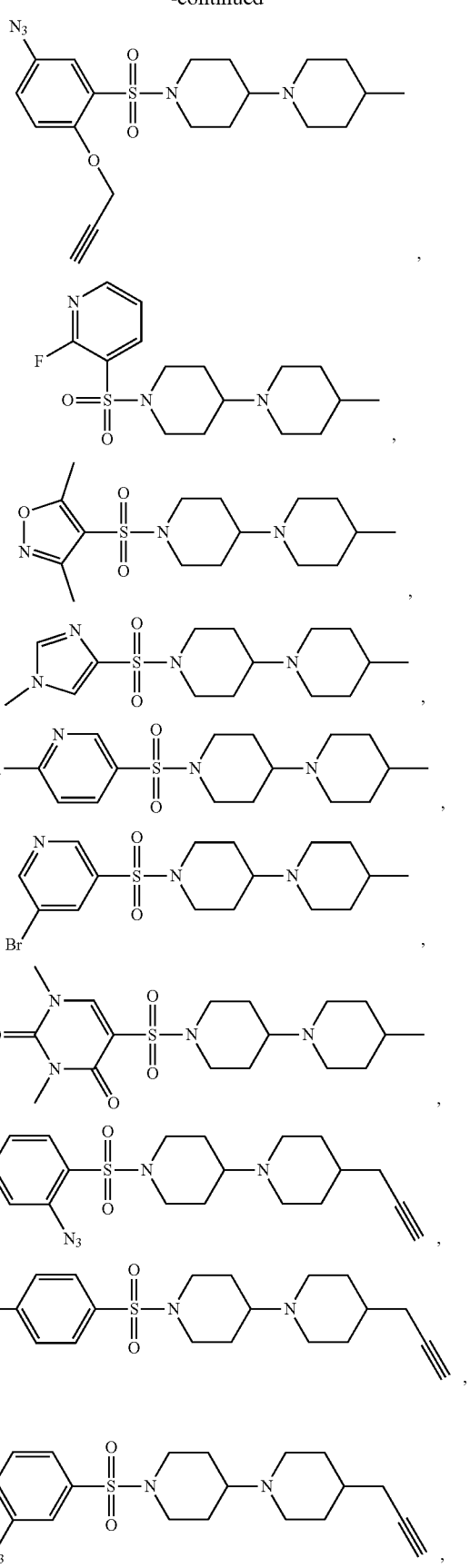

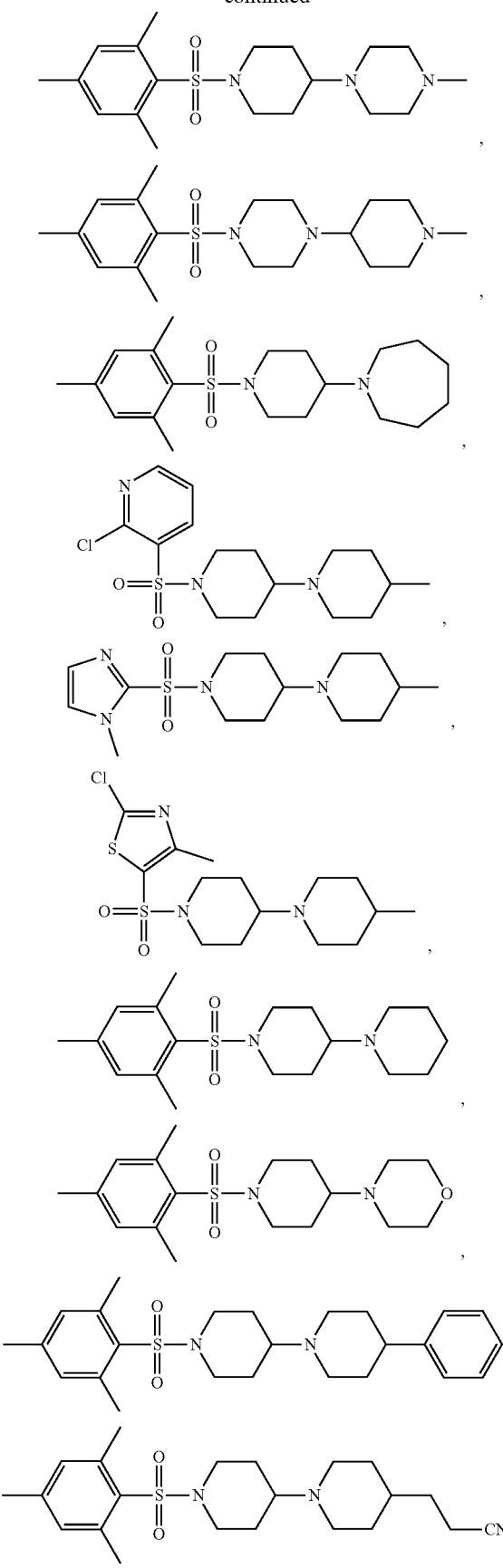
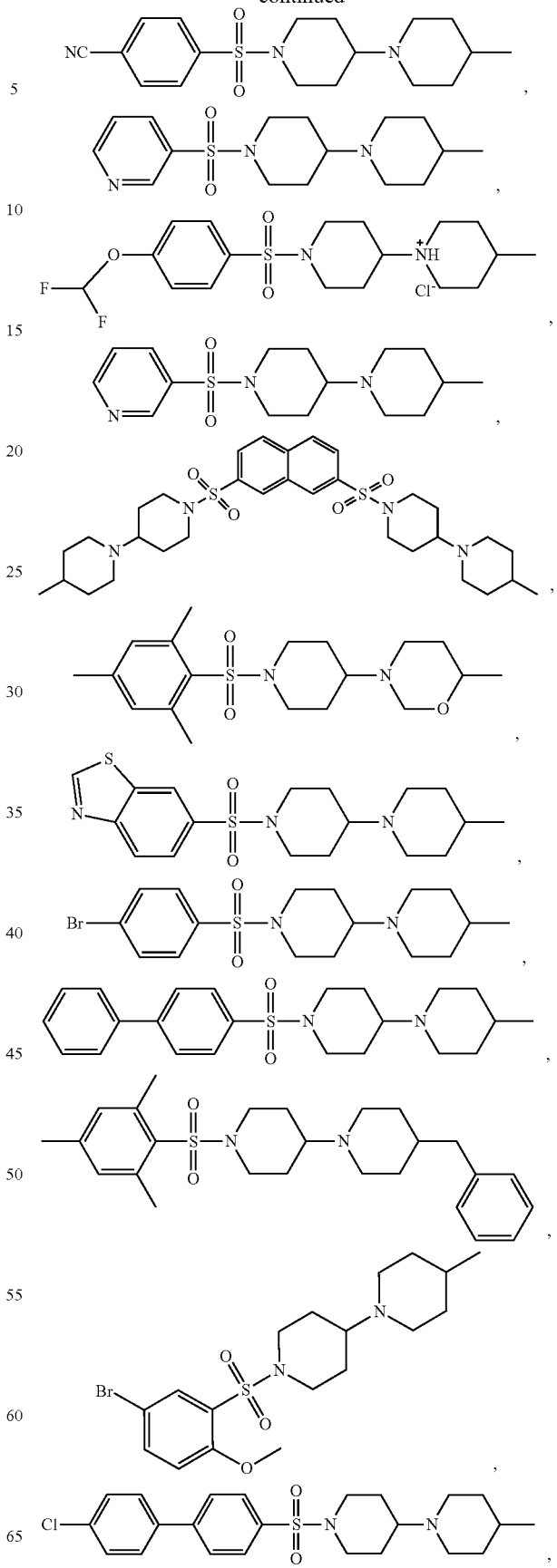

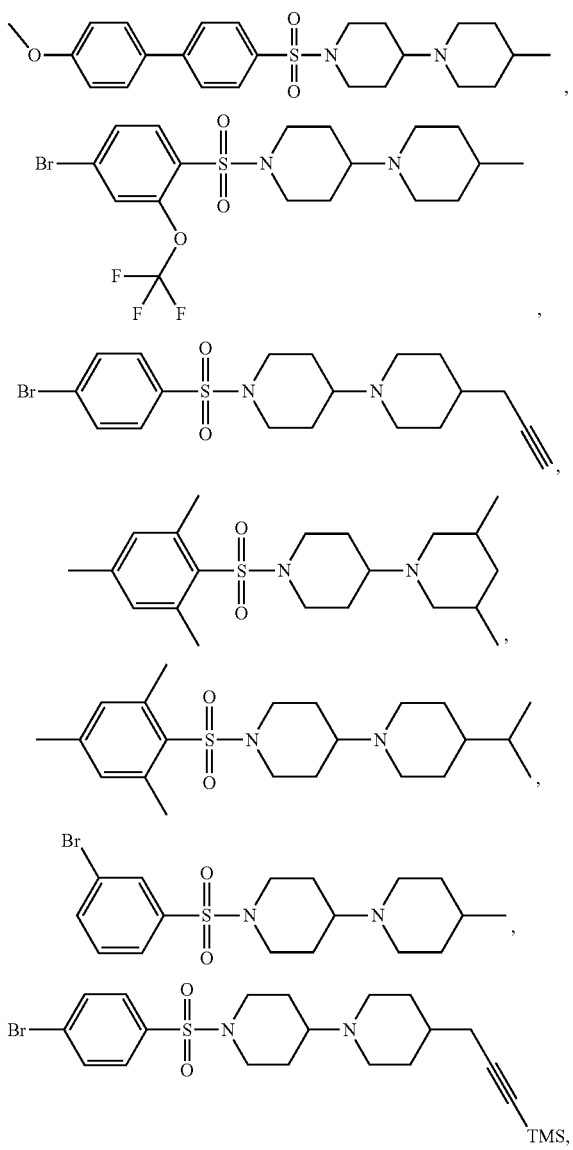

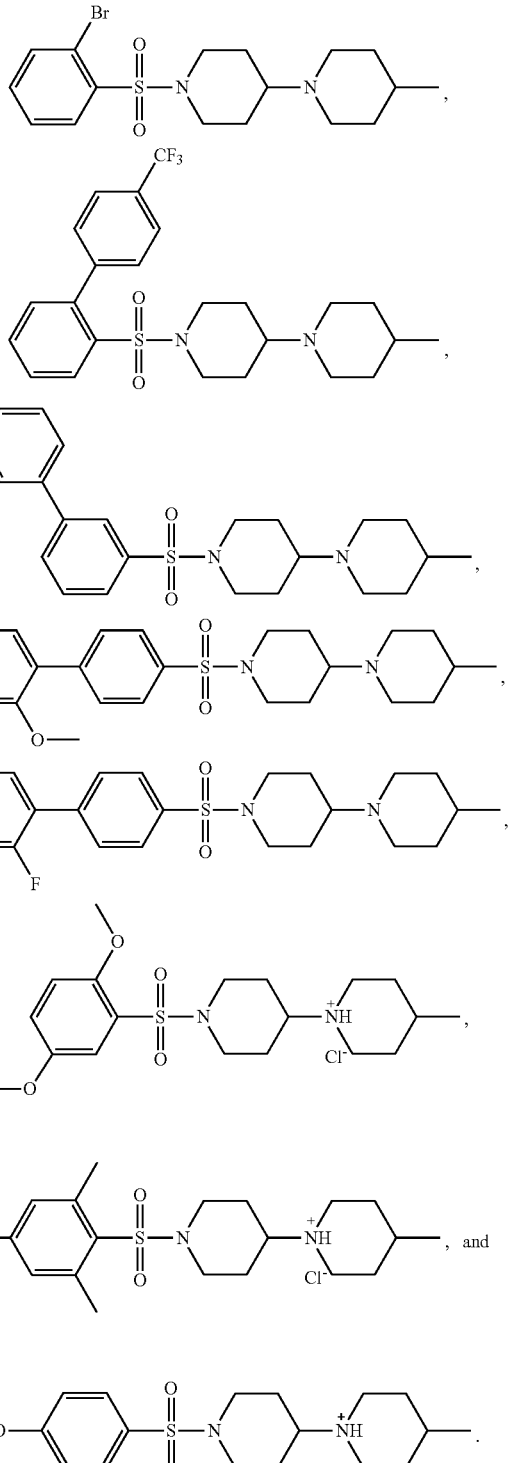

Other EBP inhibiting compounds for use in methods described herein can include derivatives of pyridilethanol (phenylethyl) amines. Derivatives of pyridilethanol (phenylethyl) amines for use in a method described herein include those described, for example, in U.S. Pat. No. 7,560,474 B2, the subject matter of which is incorporated herein by reference in its entirety. Such compounds can have the general formula (I):

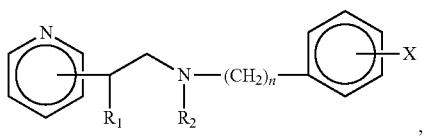

wherein n is an integer from 1 to 4, $R_1$ is a hydrogen atom, hydroxyl group or lower $C_{1-6}$ alkoxy group $R_2$ is a hydrogen atom or a straight or branched lower $C_{1-6}$ alkyl group X, is hydrogen, fluorine, chlorine, bromine, hydroxyl group, trifluoromethyl group, 3,4-di-Cl,2,4-di-Cl or lower $C_{1-6}$ alkoxy group, the enantiomers, diastereoisomers or racemates thereof or the physiologically acceptable acid addition salts thereof.

Examples of derivatives of pyridilethanol (phenylethyl) amines include: 1-(3-pyridyl)-2-(N-(2-phenylethyl)-Npropylamino)ethanol and a dihydrobromide salt of formula II:

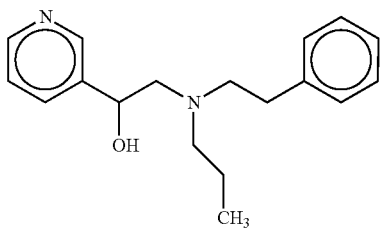

1-(3-pyridyl)-2-(N-(2-(3,4 dichlorophenyl) ethyl)-N-methylamino)ethanol and a dihydrobromide salt of formula III:

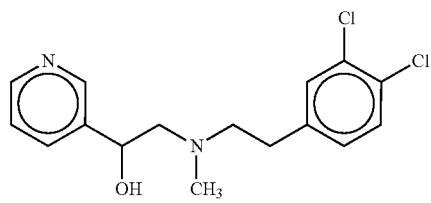

1-(3-pyridyl)-2-(N-(2-(3,4 dichlorophenyl) ethyl)-N-propylamino)ethanol and a dihydrobromide salt of formula IV:

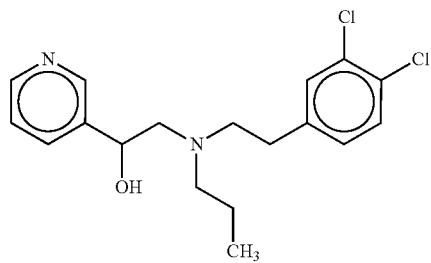

and 1-(4-pyridyl)-2-(N-(2-(3,4 dichlorophenyl)ethyl)-N-methylamino)ethanol and a dihydrobromide salt of formula V:

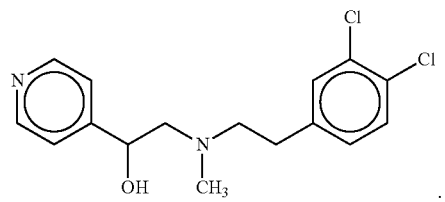

Additional examples of EBP inhibiting compounds for use in the methods described herein can include compounds having the following formulas:

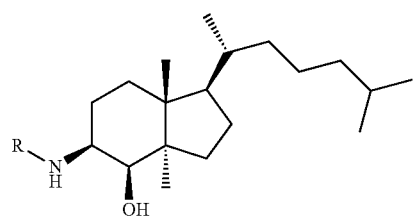

wherein R is selected from benzyl, (5-iodofuran-2yl) methyl, 3-chlorobenzyl, (furan-3-yl)methyl, pent-4-en-1yl, 2,4-dichlorobenzyl, and 2,3-dichlorobenzyl;

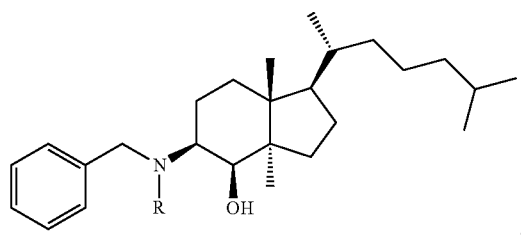

wherein R is selected from methyl, benzyl and pent-4-en-1yl;

and

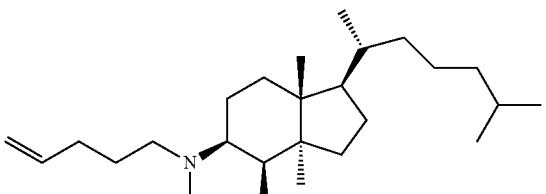

Additional EBP inhibitors for use in the methods described herein can compounds having the following formula:

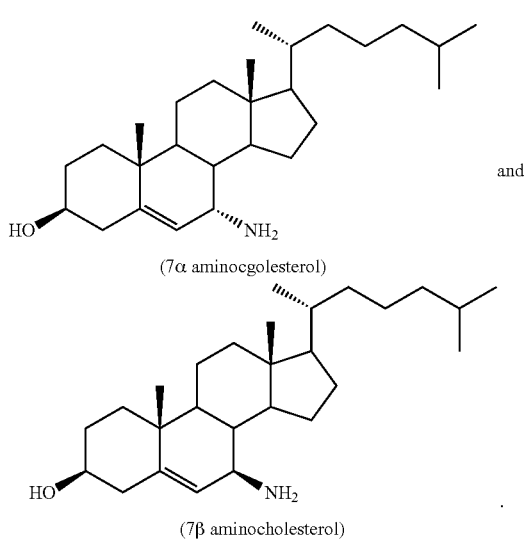

(7α aminocgolesterol)

(7β aminocholesterol)

and

Other examples of EBP inhibiting compounds for use in the methods described herein can include those described in U.S. Pat. No. 6,489,481 B 1, the subject matter of which is incorporated herein by reference in its entirety.

In certain embodiments, compounds for use in the methods described herein can include compounds capable of modulating and/or inhibiting EBP and sterol C14 reductase (also known as DHCR14, ANG1; DHCR14A; NET47; delta(14)-sterol reductase), an enzyme which catalyzes the reduction of sterol intermediates toward zymostenol during cholesterol biosynthesis. Examples of compounds capable of modulating and/or inhibiting both EBP and sterol C14 reductase include:

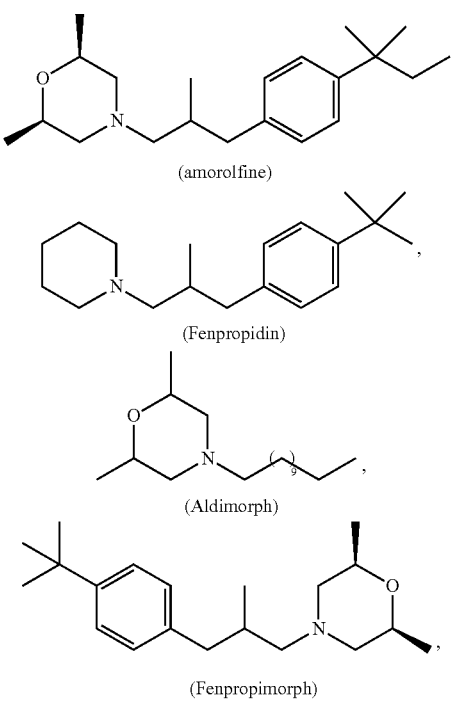

(amorolfine)

(Fenpropidin)

(Aldimorph)

(Fenpropimorph)

and analogs thereof.

Additional compounds for use in the methods described herein, which are capable of modulating and/or inhibiting sterol C14 reductase, include ziprasidone, ifenprodil, 2-methyl ketoconazole and AY9944.

Sterol C14 reductase inhibitors for use in a method described herein can also include *Corydalis* Turtschaninowii Besser extract derivatives. Exemplary *Corydalis* Turtschaninowii Besser are described in U.S. Pat. No. 6,255,317 B 1, the subject matter of which is incorporated herein by reference in its entirety, having the general formula:

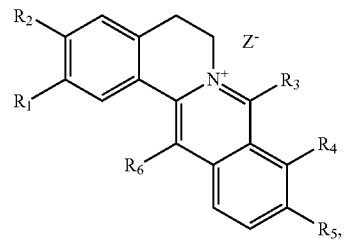

wherein $R_1$ and $R_2$ which may be the same or different from each other, represent a hydroxyl group or an alkoxy group having 1 to 4 carbon atoms or both of $R_1$ and $R_2$ represent a methylenedioxy group; $R_3$ represents a hydrogen atom; $R_4$ and $R_5$ which may be the same or different from each other, represent a hydroxyl group, a hydroxyethylamino group or an alkoxy group having 1 to 4 carbon atoms; $R_6$ represents a hydrogen atom, an alkyl group having 1 to 8 carbon atoms, an alkenyl group having 3 to 8 carbon atoms, a cycloalkylalkyl group having 1 to 7 carbon atoms, a holoalkyl group having 1 to 4 carbon atoms, an ethoxycarbonyl group, an ethoxycarbonylmethyl group, a hydroxycarbonylmethyl group, 1 ethoxycarbonylethyl group, or 2-valerolactonyl group; and Z represents a halogen atom.

Sterol C14 reductase inhibitors for use in methods described herein can also include a 5,6-dihydrodibenzeno[a,g]quinolizinium derivative and salts thereof. Such compounds are described in U.S. Pat. No. 6,030,979, the subject matter of which is incorporated herein by reference in its entirety, having the general formula:

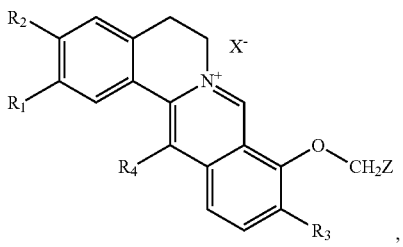

wherein $R_1$ and $R_2$ which may be the same or different from each other, represent hydroxyl group or an alkoxy group having 1 to 4 carbons or $R_1$ and $R_2$ together represent a methylenedioxy group; $R_3$ represents a hydroxyl group or an alkoxy group having 1 to 4 carbons; $R_4$ represents a hydrogen atom, an alkyl group having 1 to 8 carbons, or an alkenyl group having 3 to 8 carbons; X represents inorganic acid ion, organic acid ion or halide, more particularly, nitrate, sulfate, acetate, tartrate, maleate, succinate, citrate, furmarate, aspartate, salicylate, glycerate, ascorbate, fluoride, chloride, iodide or bromide; Z represents an alkyl group having 5 to 12 carbon, or an alkenyl group having 4 to 6 carbon, a N-benzotriazolyl group, a quinolinyl group, a furyl group, a substituted furyl group, or a group represented by the formula

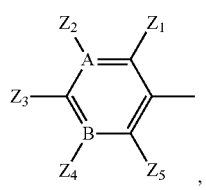

wherein $Z_1$, $Z_2$, $Z_3$, $Z_4$, and $Z_5$ which may be the same or different from each other, represent a hydrogen atom, halogen, an alkyl group having 1 to 5 carbons, a trifluoromethyl group, a phenyl group, a substituted phenyl group, a nitro group, an alkoxy group having 1 to 4 carbons, a methlyenedioxy group, a trifluoro-methoxy group, a hydroxyl group, a benzyloxy group, a phenoxy group, a vinyl group, a benzenesulfonylmethyl group or a methoxycarbonyl group; and A and B which may be the same or different from each other, represent carbon or nitrogen.

In certain embodiments, compounds for use in methods described herein can include compounds capable of modulating and/or inhibiting CYP51 (or lanosterol 14 α-demethylase), an enzyme which catalyzes the conversion of lanosterol to 4,4-dimethylcholesta-8(9),14,24-trien-3β-ol during cholesterol biosynthesis. Examples of compounds capable of modulating and/or inhibiting CYP51 include non-imidazole CYP51 inhibitors, such as (LK-935),

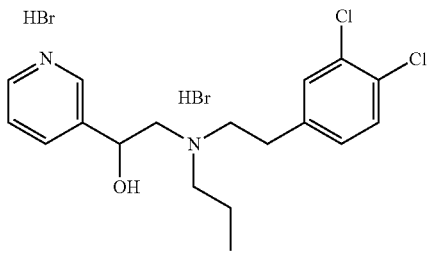 [SMILES: CCCN(CCc1ccc(Cl)c(Cl)c1)CC(O)c1cccnc1 ; Br ; Br]

and analogs having the general formula:

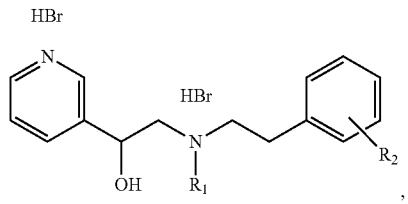

wherein $R_1$ represents an alkyl group having 1 to 3 carbon atoms; and $R_2$ represents hydrogen, (3,4)-diCL, (3,4)-diF, (3,4)-diOMe, (3,4)-diOH, 4-$NO_2$, 4-$CF_3$, or 3-$CF_3$. Additional CYP51 inhibitors can include ketoconazole and derivatives thereof, econazole, isoconazole, bifonazole, clotrimazole, miconazole, butoconazole, medroxyprogesterone acetate and fulvestrant.

In certain embodiments, small molecule compounds for use in methods described herein include compounds identified as capable of both elevating sterol intermediate levels by inhibition of a narrow window of cholesterol biosynthesis enzymes spanning CYP51 to EBP and also capable of enhancing the formation of oligodendrocytes and myelination. Examples of compounds capable of both elevating sterol intermediate levels by inhibiting the cholesterol biosynthesis enzymes spanning CYP51 to EBP and enhancing myelination include: the CYP51 inhibitors bifonazole, clotrimazole, miconazole, butoconazole, ketoconazole, Fulvestrant; the Sterol 14-reductase (TM7SF2/LBR) inhibitors amorolfine, ifenprodil, and ziprasidone; and the EBP inhibitors Tasin-1, tamoxifen, benztropine, clemastine, trans-U50488, EPZ005687, raloxifene, hydroxyzine, vesamicol, L-745,870, TMB-8, cis-N-cyclohexyl-N-ethyl-3-(3-chloro-4-cyclohexylphenyl)prop-2-enylamine, pFluorohexahydro-Siladifenidol, pramoxine, and toremifene. (see FIG. 14)

In some embodiments, compounds for use in methods described herein can include compounds capable of modulating and/or inhibiting NAD(P) dependent steroid dehydrogenase-like (NSDHL or also known as 3β-hydroxysteroid dehydrogenase/C4 decarboylase). NSDHL lies in the cholesterol pathway distal to lanosterol synthase, and catalyzes $NAD^+$-dependent oxidative decarboxylation of 4α-carboxysterolintermediates involved in the C-4 demethylation process of sterol precursors to produce the corresponding 3-keto, C-4 decaboxylated products. In certain embodiments, a NSDHL inhibiting compound for use in methods described herein can include a compound (FR171456) having the formula

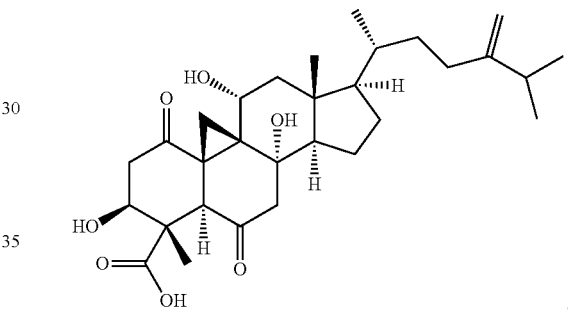

(FR171456)

as well as analogs, derivatives and pharmaceutical salts thereof.

In some embodiments, compounds for use in methods described herein include compounds capable of modulating and/or inhibiting DHCR24 (24-dehydrocholesterol reductase), an enzyme which catalyzes the reduction of the delta-24 double bond of sterol intermediates during cholesterol biosynthesis. For example, compounds for use in a method described herein include compounds capable of inhibiting DHCR24 mediated conversion of desmosterol to cholesterol in the cholesterol biosynthesis pathway at an amount effective to promote and/or induce oligodendrocyte precursor cell differentiation, proliferation and/or maturation. For example, the compounds can inhibit DHCR24 mediated conversion of desmosterol to cholesterol in the cholesterol biosynthesis pathway by at least 5%, 10%, 20%, 25%, 30%, 40%, 50%, 60%, 70%, 75%, 80%, 85%, 90%, 95%, or 99% as compared to the amount of DHCR24 mediated conversion of desmosterol to cholesterol in untreated OPCs or subject.

Compounds described herein may be synthesized using standard synthetic techniques known to those of skill in the art or using methods known in the art in combination with methods described herein. In additions, solvents, temperatures and other reaction conditions presented herein may vary according to the practice and knowledge of those of skill in the art.

The starting material used for the synthesis of compounds described herein can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999) (all of which are incorporated by reference in their entirety).

In other embodiments, the at least one agent that enhances and/or induces accumulation of Δ8,9-unsaturated sterol intermediates of the cholesterol biosynthesis pathway in the OPCs can include an agent that reduces or inhibits expression of enzymes within the cholesterol biosynthesis pathway, such as EBP, C14 reductase, or CYP51 expression, in tissue or cells of a subject in need thereof. "Expression", means the overall flow of information from a gene to produce a gene product (typically a protein, optionally post-translationally modified or a functional/structural RNA).

In some embodiments, the agent can include an RNAi construct that inhibits or reduces expression of the EBP, C14 reductase, or CYP51 expression in a cell. RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner.

As used herein, the term "dsRNA" refers to siRNA molecules or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

As used herein, the term "RNAi construct" is a generic term used throughout the specification to include small interfering RNAs (siRNAs), hairpin RNAs, and other RNA species, which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences.

The choice of promoter and other regulatory elements generally varies according to the intended host cell, such as an OPC. In general, expression vectors of utility in recombinant DNA techniques are often in the form of "plasmids" which refer to circular double stranded DNA loops, which, in their vector form are not bound to the chromosome. In the present specification, "plasmid" and "vector" are used interchangeably as the plasmid is the most commonly used form of vector. However, the application describes other forms of expression vectors that serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, embodiments tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, a modified ribonucleotide can be introduced by in vitro enzymatic or organic synthesis.

Methods of chemically modifying RNA molecules can be adapted for modifying RNAi constructs (see for example, *Nucleic Acids Res,* 25:776-780; *J Mol Recog* 7:89-98; *Nucleic Acids Res* 23:2661-2668; *Antisense Nucleic Acid*

*Drug Dev* 7:55-61). Merely to illustrate, the backbone of an RNAi construct can be modified with phosphorothioates, phosphoramidate, phosphodithioates, chimeric methylphosphonate-phosphodiesters, peptide nucleic acids, 5-propynylpyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount, which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules described herein can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (*Proc Natl Acad Sci USA*, 98:9742-9747; *EMBO J*, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, *Genes Dev*, 2002, 16:948-58; *Nature*, 2002, 418:38-9; *RNA*, 2002, 8:842-50; and *Proc Natl Acad Sci*, 2002, 99:6047-52. Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an example of a vector for bi-directional transcription of a transgene to yield both sense and antisense RNA transcripts of the same transgene in a eukaryotic cell. Accordingly, certain embodiments provide a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

In some embodiments, a lentiviral vector can be used for the long-term expression of a siRNA, such as a short-hairpin RNA (shRNA), to knockdown expression of the RPTP in a cancer cell. Although there have been some safety concerns about the use of lentiviral vectors for gene therapy, self-inactivating lentiviral vectors are considered good candidates for gene therapy as they readily transfect mammalian cells.

By way of example, short-hairpin RNA (shRNA) down regulation of the AKR1A1 expression can be created using OligoEngene software (OligoEngine, Seattle, WA) to identify sequences as targets of siRNA. The oligo sequences can be annealed and ligated into linearized pSUPER RNAi vector (OligoEngine, Seattle, WA) and transformed in *E. coli* strain DH5a cells. After positive clones are selected, plasmid can be transfected into 293T cells by calcium precipitation. The viral supernatant collected containing shRNA can then be used to infect mammalian cells in order to down regulate the EBP, C14 reductase, or CYP51 enzyme.

In another embodiment, the EBP, C14 reductase, or CYP51 inhibitor can include antisense oligonucleotides. Antisense oligonucleotides are relatively short nucleic acids that are complementary (or antisense) to the coding strand (sense strand) of the mRNA encoding a particular protein. Although antisense oligonucleotides are typically RNA based, they can also be DNA based. Additionally, antisense oligonucleotides are often modified to increase their stability.

The binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding a specific protein. Accordingly, antisense oligonucleotides decrease the expression and/or activity of a particular protein (e.g., EBP, C14 reductase, or CYP51).

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups, such as peptides (e.g., for targeting host cell receptors), or agents facilitating transport across the cell membrane (see, e.g., *Proc Natl Acad Sci* 86:6553-6556; *Proc Natl Acad Sci* 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents (See, e.g., *BioTechniques* 6:958-976) or intercalating agents. (See, e.g., *Pharm Res* 5:539-549). To this end, the oligonucleotide may be conjugated or coupled to another molecule.

Oligonucleotides described herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209), methylphosphonate oligonucleotides can be prepared by use of controlled pore glass polymer supports (*Proc Natl Acad Sci* 85:7448-7451).

The selection of an appropriate oligonucleotide can be performed by one of skill in the art. Given the nucleic acid sequence encoding a particular protein, one of skill in the art can design antisense oligonucleotides that bind to that protein, and test these oligonucleotides in an in vitro or in vivo system to confirm that they bind to and mediate the degradation of the mRNA encoding the particular protein. To design an antisense oligonucleotide that specifically binds to and mediates the degradation of a particular protein, it is important that the sequence recognized by the oligonucleotide is unique or substantially unique to that particular protein. For example, sequences that are frequently repeated across protein may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for a particular protein.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense oligonucleotide sufficient to suppress translation on endogenous mRNAs in certain instances. Therefore, another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Expression of the sequence encoding the antisense RNA can be by a promoter known in the art to act in mammalian, preferably human cells. Such promoters can be inducible or constitutive. Such promoters include but are not limited to: the SV40 early promoter region (*Nature* 290:304-310), the promoter contained in the 3' long terminal repeat of Rous sarcoma virus (*Cell* 22:787-797), the herpes thymidine kinase promoter (*Proc Natl Acad Sci* 78:1441-1445), the regulatory sequences of the metallothionein gene (*Nature* 296:39-42), etc. A type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

In some embodiments, endogenous expression of an enzyme that synthesizes one or more sterol intermediates in the cholesterol biosynthesis pathway of OPC cells can be reduced in OPCs through the use of a nuclease to edit (e.g., mutate) genes encoding the enzyme or a genetic regulatory elements thereof. Nucleases and related systems for use in method described herein can include, but are not limited to a zinc finger nuclease (ZFN), a TALE-effector (TALEN), a CRISPR/Cas system or an NgAgo system. In some embodiments, the endogenous genes encoding EBP, C14 reductase, and/or CYP51 enzymes or a genetic regulatory element thereof can be edited using CRISPR/Cas9 guide RNAs. In certain aspects the nuclease can include a class 2 CRISPR/Cas system. For example, the class 2 CRISPR/Cas system can include a type II Cas9-based CRISPR system or a type V Cpf1-based CRISPR system.

In further embodiments, the agent that enhances and/or induces accumulation of $\Delta 8,9$-unsaturated sterol intermediates of the cholesterol biosynthesis pathway in the OPCs can include at least one $\Delta 8,9$-unsaturated sterol intermediates of the cholesterol biosynthesis pathway in OPCs or a derivative thereof that enhances generation of oligodendrocytes from the OPCs. In some embodiments, the $\Delta 8,9$-unsaturated sterol intermediates includes at least one of lanosterol, 14-dehydrozymostenol, FF-MAS, MAS-412, zymosterol, zymostenol and derivatives thereof.

Agents that enhance and/or induce accumulation of $\Delta 8,9$-unsaturated sterol intermediates of the cholesterol biosynthesis pathway in the OPCs described herein, can be provided and administered in the form of pharmaceutical compositions for the in vivo promotion of oligodendrocyte precursor differentiation and/or maturation. The pharmaceutical compositions can be administered to any subject that can experience the beneficial effects of the oligodendrocyte precursor differentiation and/or maturation compounds of the present invention. Foremost among such animals are humans, although the present invention is not intended to be so limited.

Pharmaceutical compositions for use in the methods of the present invention preferably have a therapeutically effective amount of the compound or salts thereof in a dosage in the range of 0.01 to 1,000 mg/kg of body weight of the subject, and more preferably in the range of from about 10 to 100 mg/kg of body weight of the patient.

The overall dosage will be a therapeutically effective amount depending on several factors including the overall health of a subject, the subject's disease state, severity of the condition, the observation of improvements and the formulation and route of administration of the selected agent(s). Determination of a therapeutically effective amount is within the capability of those skilled in the art. The exact formulation, route of administration and dosage can be chosen by the individual physician in view of the subject's condition.

The present invention provides a method of treating diseases in a subject by promoting the differentiation and/or proliferation of oligodendrocyte precursors in a subject. The method includes administering to the subject in need thereof a therapeutically effective amount of a pharmaceutical compound in accordance with the present invention. As described above, one or more of the compounds can be administered in association with one or more non-toxic, pharmaceutically acceptable carriers and/or diluents and/or adjuvants and if desired other active ingredients.

The "therapeutically effective amount" of compounds and salts thereof used in the methods of the present invention varies depending upon the manner of administration, the age and body weight of the subject, and the condition of the subject to be treated, and ultimately will be decided by those skilled in the art. The term "therapeutically effective amount" refers to an amount (dose) effective in treating a subject, having, for example, a neurodegenerative disease (e.g. multiple sclerosis).

In certain embodiments, compounds described herein may be administered in an amount effective to promote myelination of CNS neurons in a subject by an increase in the amount of myelin proteins (e.g., MBP) of at least 5%, 10%, 20%, 25%, 30%, 40%, 50%, 60%, 70%, 75%, 80%, 85%, 90%, 95%, 100%, 110%, 120%, 130%, 140%, 150%, 160%, 170%, 180%, 190%, 200%, 250%, 300%, 350%, 400%, 450%, 500%, 550%, 600%, 650%, 700%, 750%, 800%, 850%, 900%, 950%, or 1000% as compared to the level of myelin proteins of an untreated CNS neurons or subject.

In other embodiments, compounds described herein may be administered in an amount effective to promote survival of CNS neurons in a subject by an increase in the number of surviving neurons of at least 5%, 10%, 20%, 25%, 30%, 40%, 50%, 60%, 70%, 75%, 80%, 85%, 90%, 95%, 100%, 110%, 120%, 130%, 140%, 150%, 160%, 170%, 180%, 190%, 200%, 250%, 300%, 350%, 400%, 450%, 500%, 550%, 600%, 650%, 700%, 750%, 800%, 850%, 900%, 950%, or 1000% as compared to the number of surviving neurons in an untreated CNS neurons or subject.

In some embodiments, compounds described herein may be administered in an amount effective enhance generation of OPCs in the subject's central nervous system by an increase in the amount of OPC generation of at least 5%, 10%, 20%, 25%, 30%, 40%, 50%, 60%, 70%, 75%, 80%, 85%, 90%, 95%, 100%, 110%, 120%, 130%, 140%, 150%, 160%, 170%, 180%, 190%, 200%, 250%, 300%, 350%, 400%, 450%, 500%, 550%, 600%, 650%, 700%, 750%, 800%, 850%, 900%, 950%, or 1000% as compared to the amount of OPC generation in untreated OPCs or subject.

In some embodiments, compounds described herein may be administered in an amount effective to induce endogenous oligodendrocyte precursor cell (OPC) differentiation in the subject's central nervous system by an increase in the amount of OPC differentiation of at least 5%, 10%, 20%, 25%, 30%, 40%, 50%, 60%, 70%, 75%, 80%, 85%, 90%, 95%, 100%, 110%, 120%, 130%, 140%, 150%, 160%, 170%, 180%, 190%, 200%, 250%, 300%, 350%, 400%, 450%, 500%, 550%, 600%, 650%, 700%, 750%, 800%, 850%, 900%, 950%, or 1000% as compared to the amount of OPC differentiation in untreated OPCs or subject.

In some embodiments, compounds described herein may be administered in an amount effective to modulate the cholesterol biosynthesis pathway in a OPC cells in a subject by a decrease in the amount of cholesterol and/or one or more sterol intermediates synthesis in OPCs of at least 5%, 10%, 20%, 25%, 30%, 40%, 50%, 60%, 70%, 75%, 80%, 85%, 90%, 95%, or 99% as compared to the amount of cholesterol and/or one or more sterol intermediates synthesis in untreated OPCs or subject.

"Treating" or "treatment" as used herein, refers to the reduction in severity and/or frequency of symptoms, elimination of symptoms and/or underlying cause, prevention of the occurrence of symptoms and/or their underlying cause, and improvement or remediation of disease. Such treatment need not necessarily completely ameliorate the disease. For example, treatment of a subject with a neurodegenerative disease by administration of oligodendrocyte precursor differentiation compounds of the present invention can encompass inhibiting or causing regression of the disease. Further, such treatment can be used in conjunction with other traditional treatments for neurodegenerative diseases known to those of skill in the art.

The pharmaceutical compositions of the present invention can be administered to a subject by any means that achieve their intended purpose. For example, administration can be by parenteral, subcutaneous, intravenous, intraarticular, intrathecal, intramuscular, intraperitoneal, or intradermal injections, or by transdermal, buccal, oromucosal, ocular routes or via inhalation. Alternatively, or concurrently, administration can be by the oral route.

Formulation of the pharmaceutical compounds for use in the modes of administration noted above (and others) are known in the art and are described, for example, in Remington's Pharmaceutical Sciences (18th edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y., U.S.A., 2005; and Mathiowitz et al., eds., Bioadhesive Drug Delivery Systems, Drugs and the Pharmaceutical Sciences Series, Marcel Dekker, Inc., N.Y., U.S.A., 1999. Compounds of the invention can be formulated into pharmaceutical compositions containing pharmaceutically acceptable non-toxic excipients and carriers. The excipients are all components present in the pharmaceutical formulation other than the active ingredient or ingredients. Suitable excipients and carriers useful in the present invention are composed of materials that are considered safe and effective and may be administered to an individual without causing undesirable biological side effects, or unwanted interactions with other medications. Suitable excipients and carriers are those, which are composed of materials that will not affect the bioavailability and performance of the agent. As generally used herein "excipient" includes, but is not limited to surfactants, emulsifiers, emulsion stabilizers, emollients, buffers, solvents, dyes, flavors, binders, fillers, lubricants, and preservatives. Suitable excipients include those generally known in the art such as the "Handbook of Pharmaceutical Excipients", 4th Ed., Pharmaceutical Press, 2003.

The compounds can be administered to a subject to treat neurodegenerative diseases and disorders. A neurodegenerative disease, as contemplated for treatment by methods of the present invention, can arise from but is not limited to an inherited genetic abnormality, stroke, heat stress, head and spinal cord trauma (blunt or infectious pathology), and/or bleeding that occurs in the brain.

The neurodegenerative disease contemplated for treatment by some aspects of the present invention can include a myelin related disorder. Myelin disorders can include any disease, condition (e.g., those occurring from traumatic spinal cord injury and cerebral infarction), or disorder related to demylination, insufficient myelination and remyelination, or dysmyelination in a subject. A myelin related disorder as used herein can arise from a myelination related disorder or demyelination resulting from a variety of neurotoxic insults. "Demyelination" as used herein, refers to the act of demyelinating, or the loss of the myelin sheath insulating the nerves, and is the hallmark of some neurodegenerative autoimmune diseases, including multiple sclerosis, transverse myelitis, chronic inflammatory demyelinating polyneuropathy, and Guillain-Barre Syndrome. Leukodystrophies are caused by inherited enzyme deficiencies, which cause abnormal formation, destruction, and/or abnormal turnover of myelin sheaths within the CNS white matter. Both acquired and inherited myelin disorders share a poor prognosis leading to major disability. Thus, some embodiments of the present invention can include methods for the treatment of neurodegenerative autoimmune diseases in a subject. Remyelination of neurons requires oligodendrocytes. The term "remyelination", as used herein, refers to the re-generation of the nerve's myelin sheath by replacing myelin producing cells or restoring their function.

Myelin related diseases or disorders which may be treated or ameliorated by the methods of the present invention include diseases, disorders or injuries which relate to dysmyelination or demyelination in a subject's brain cells, e.g., CNS neurons. Such diseases include, but are not limited to, diseases and disorders in which the myelin which surrounds the neuron is either absent, incomplete, not formed properly, or is deteriorating. Such disease include, but are not limited to, multiple sclerosis (MS), neuromyelisits optica (NMO), progressive multifocal leukoencephalopathy (PML), encephalomyelitis (EPL), central pontine myelolysis (CPM), adrenoleukodystrophy, Alexander's disease, Pelizaeus Merzbacher disease (PMD), Vanishing White Matter Disease, Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, Bassen-Kornzweig syndrome, Marchiafava-Bignami syndrome, metachromatic leukodystrophy, trigeminal neuralgia, acute dissmeminated encephalitis, Guillian-Barre syndrome, Charcot-Marie-Tooth disease Bell's palsy, and mental health disorders such as schizophrenia.

In some embodiments, myelin related diseases or disorders which may be treated or ameliorated by the methods of the present invention include leukodystrophies. Leukodystrophies are a group of progressive, metabolic, genetic diseases that affect the brain, spinal cord and often the peripheral nerves. Each type of leukodystrophy is caused by a specific gene abnormality that leads to abnormal development or destruction of the myelin sheath of the brain. Each type of leukodystrophy affects a different part of the myelin sheath, leading to a range of neurological problems. Exemplary leukodystrophies which may be treated or ameliorated by the methods of the present invention include, but are not limited to, adult-onset autosomal dominant leukodystrophy (ADLD), Aicardi-Goutieres syndrome, Alexander disease, CADASIL, Canavan disease, CARASIL, cerebrotendionous xanthomatosis, childhood ataxia and cerebral ypomyelination (CACH)/vanishing white matter disease (VWMD), Fabry disease, fucosidosis, GM1 gangliosidosis, Krabbe disease, L-2-hydroxyglutaric aciduria, megalencephalic leukoencephalopathy with subcortical cysts, metachromatic leukodystrophy, multiple sulfatase deficiency, Pelizaeus-Merzbacher disease (PMD), Pol III-related leukodystrophies, Refsum disease, salla disease (free sialic acid storage disease), Sjogren-Larsson syndrome, X-linked adrenoleukodystrophy, and Zellweger syndrome spectrum disorders.

Myelin related diseases or disorders which may be treated or ameliorated by the methods of the present invention include a disease or disorder characterized by a myelin deficiency. Insufficient myelination in the central nervous system has been implicated in a wide array of neurological disorders. Among these are forms of cerebral palsy in which a congenital deficit in forebrain myelination in children with periventricular leukomalacia, contributes to neurological morbidity (Goldman et al., 2008) Goldman, S. A., Schanz, S., and Windrem, M. S. (2008). Stem cell-based strategies for treating pediatric disorders of myelin. Hum Mol Genet. 17, R76-83. At the other end of the age spectrum, myelin loss and ineffective repair may contribute to the decline in cognitive function associated with senescence (Kohama et al., 2011) Kohama, S. G., Rosene, D. L., and Sherman, L. S. (2011) Age (Dordr). Age-related changes in human and non-human primate white matter: from myelination disturbances to cognitive decline. Therefore, it is contemplated that effective compounds and methods of enhancing myelination and/or remyelination may have substantial therapeutic benefits in halting disease progression and restoring function in MS and in a wide array of neurological disorders.

In some embodiments, the compounds of the present invention can be administered to a subject that does not have, and/or is not suspected of having, a myelin related disorder in order to enhance or promote a myelin dependent process. In some embodiments, compounds described herein can be administered to a subject to promote myelination of CNS neurons in order to enhance cognition, which is known to be a myelin dependent process, in cognitive healthy subjects. In certain embodiments, compounds described herein can be administered in combination with cognitive enhancing (nootropic) agents. Exemplary agents include any drugs, supplements, or other substances that improve cognitive function, particularly executive functions, memory, creativity, or motivation, in healthy individuals. Non limiting examples include racetams (e.g., piracetam, oxiracetam, and aniracetam), nutraceuticals (e.g., bacopa monnieri, panax ginseng, ginko biloba, and GABA), stimulants (e.g., amphetamine pharmaceuticals, methylphenidate, eugeroics, xanthines, and nicotine), L-Theanine, Tolcapone, Levodopa, Atomoxetine, and Desipramine.

One particular aspect of the present invention contemplates the treatment of multiple sclerosis in a subject. The method includes administering to the subject a therapeutically effective amount of one or more oligodendrocyte differentiation promoting compound(s) described above.

Multiple sclerosis (MS) is the most common demyelinating disease. In multiple sclerosis, the body's failure to repair myelin is thought to lead to nerve damage, causing multiple sclerosis associated symptoms and increasing disability. The demyelination observed in MS is not always permanent and remyelination has been documented in early stages of the disease. It is contemplated that methods of the present invention can promote oligodendrocyte precursor cell differentiation in a subject, therefore leading to endogenous remyelination.

Another particular aspect of the present invention contemplates the treatment of a genetic myelin disorder which results from the loss of myelin (demyelination) in a subject.

The method includes administering to the subject a therapeutically effective amount of one or more agents(s) that enhance and/or induce accumulation of Δ8,9-unsaturated sterol intermediates of the cholesterol biosynthesis pathway in OPCs described above. In certain embodiments, the genetic myelin disorder is a leukodystrophy such as, but not limited to Pelizaeus Merzbacher Disease (PMD)

Another strategy for treating a subject suffering from a neurodegenerative disease or disorder is to administer a therapeutically effective amount of a compound described herein along with a therapeutically effective amount of additional oligodendrocyte differentiation and/or proliferation inducing agent(s) and/or anti-neurodegenerative disease agent. Examples of anti-neurodegenerative disease agents include L-dopa, cholinesterase inhibitors, anticholinergics, dopamine agonists, steroids, and immunomodulators including interferons, monoclonal antibodies, and glatiramer acetate.

Therefore, in a further aspect of the invention, the oligodendrocyte precursor differentiation and/or proliferation inducing compounds described herein can be administered as part of a combination therapy with adjunctive therapies for treating neurodegenerative and myelin related disorders.

The phrase "combination therapy" embraces the administration of the oligodendrocyte precursor differentiation inducing compounds described herein and a therapeutic agent as part of a specific treatment regimen intended to provide a beneficial effect from the co-action of these therapeutic agents. When administered as a combination, the oligodendrocyte precursor differentiation inducing compound and a therapeutic agent can be formulated as separate compositions. Administration of these therapeutic agents in combination typically is carried out over a defined time period (usually minutes, hours, days or weeks depending upon the combination selected).

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (e.g., surgery).

In another aspect of the invention, the therapeutic agents administered in a combination therapy with the oligodendrocyte differentiation and/or proliferation inducing compounds described herein can include at least one anti-neurodegenerative agent such as but not limited to, an immunotherapeutic agent.

An immunotherapeutic agent for use in the methods of the present invention can include therapies which target the immune component of the disease and/or the acute inflammatory response evidenced during an acute attack in remitting-relapsing multiple sclerosis. Examples include, but are not limited to immunomodulators such as interferon beta-la and beta-1b (Avonex and Betaseron respectively), natalizumab (Copaxone) natalizumab (Tysabri), glatiramer acetate (Copaxone) or mitoxantrone.

The invention is further illustrated by the following example, which is not intended to limit the scope of the claims.

EXAMPLE

In this Example we show that regeneration of myelin is mediated by oligodendrocyte progenitor cells (OPCs), an abundant stem cell population in the CNS and the principal source of new myelinating oligodendrocytes. Loss of myelin-producing oligodendrocytes in the central nervous system (CNS) underlies a number of neurological diseases, including multiple sclerosis and diverse genetic diseases. Using high throughput chemical screening approaches, we have identified small molecules that promote myelination by stimulating oligodendrocyte formation from OPCs, and functionally enhance remyelination in vivo. Here, we demonstrate that a broad range of these pro-myelinating molecules function not through their canonical targets but by directly inhibiting CYP51, sterol 14-reductase, and EBP, a narrow range of enzymes within the cholesterol biosynthesis pathway. We found that chemical or genetic inhibition of these enzymes resulted in accumulation of Δ8,9-unsaturated sterol intermediates, which when independently supplied to OPCs enhanced formation of new oligodendrocytes. Functional studies showed that small molecule inhibitors of CYP51, sterol 14-reductase, and EBP induce accumulation of Δ8,9-unsaturated sterols in human brain tissue in vitro and mouse brain tissue in vivo. At the same doses, these molecules also enhance the rate of myelination in vivo in a lysolecithin-induced mouse model of focal demyelination. Collectively, our results provide a unifying mechanism-of-action for most known small-molecule enhancers of oligodendrocyte formation and highlight specific targets for the development of optimal remyelinating therapeutics.

Methods

No statistical methods were used to predetermine sample size.

Small Molecules

The identity and purity of small molecules were authenticated by LC/MS before use. The following compounds were purchased from Sigma-Aldrich as a solid: Ketoconazole, Miconazole, Clotrimazole, Fluconazole, Fulvestrant, Ifenprodil, Benztropine, Liothyronine, Bexarotene, Tamoxifen, Ospemifene, GSK343, Trans-U50488 and Cholesterol. The following compounds were purchased from Cayman Chemicals as a solid: Clemastine, AY9944, YM53601 and Ro-48-8071. The following compounds were obtained from Janssen Pharmaceuticals as a solid: R-trans-Ketoconazole, and S-trans-Ketoconazole. Mevastatin was purchased as a solid from Selleck Chemicals. The following compounds were purchased from Selleck Chemicals as a 10 mM DMSO solution: Bifonazole, Butoconazole, Amorolfine, Toremifene, EPZ005687, EPZ6438, UNC1999, Hydroxyzine, Ziprasidone, p-Fluorohexahydro-sila-difenidol (abbreviated in figures as Sigma H127), Vesamicol, Raloxifene, L-745,870, TMB-8, Pramoxine, Varespladib, Tanshinone-I, Levofloxacin, Nateglinide, Abiraterone, Allopurinol, Detomidine, Rivastigmine, Beta carotene, BEZ-235, Scopolamine, and Homatropine. Pirenzepine and Telenzepine were purchased from Sigma-Aldrich as a 10 mM DMSO solution. Cholesterol biosynthetic intermediates were purchased from Avanti Polar Lipids as a solid: Lanosterol, Zymosterol, Zymostenol, Lathosterol, Desmosterol, 7-dehydrodesmosterol and T-MAS. 14-dehydrozymostenol (cholesta-8,14-dien-β-ol) was provided by Franz Bracher, Ludwig-Maximilians University of Munich. Imidazole 124, TAS1N-1, and MG139 were synthesized as reported.

Mouse OPC Preparation

To rigorously assess effects of small molecule and genetic treatments on OPCs, all treatments were assayed in two batches of epiblast stem cell-derived OPCs, and key results were confirmed using mouse primary OPCs. OPCs were generated from two separate EpiSC lines, EpiSC5 (giving rise to OPC-5 OPCs) and 129O1 (giving rise to OPC-1 OPCs). Unless otherwise noted, results in OPC-5 cells are presented in FIGS. 1-4 while results in OPC-1 are presented in FIG. 5-11.

EpiSC-derived OPCs were obtained using in vitro differentiation protocols and culture conditions described previously. To ensure uniformity throughout all in vitro screening experiments, EpiSC-derived OPCs were sorted to purity by fluorescence activated cell sorting at passage five with conjugated CD 140a-APC (eBioscience, 17-1401; 1:80) and NG2-AF488 (Millipore, AB5320A4; 1:100) antibodies. Sorted batches of OPCs were expanded and frozen down in aliquots. OPCs were thawed into growth conditions for one passage before use in further assays. Cultures were regularly tested and shown to be mycoplasma free.

To obtain mouse primary OPCs, whole brain was removed from post-natal day 2 pups anesthetized on ice. Brains were placed in cold DMEM/F12, and the cortices were isolated and the meninges were removed. The cortices were manually chopped and processed with the Tumor Dissociation Kit (Miltenyi) and incubated at 37° C. for 10 minutes. The cell suspension was filtered through a 70 μM filter and centrifuged at 200×g for 4 minutes at room temperature. The cells were washed in DMEM/F12, re-centrifuged and plated in poly-Ornithine and Laminin-treated flasks containing DMEM/P12 supplemented with $N_2$ Max, B27 (ThermoFisher), 20 ng/mL FGF, and 20 ng/mL PDGF. Small molecules were passaged once prior to treatment. Media was changed every 48 hours.

In Vitro Phenotypic Screening of OPCs

EpiSC-derived OPCs were grown and expanded in poly-ornithine (PO) and laminin-coated flasks with growth medium (DMEM/F12 supplemented with N2-MAX (R&D Systems), B-27 (ThermoFisher), GlutaMax (Gibco), FGF2 (10 μg/mL, R&D systems, 233-FB-025) and PDGF-AA (10 μg/mL, R&D systems, 233-AA-050) before harvesting for plating. The cells were seeded onto poly-D-lysine 96-well CellCarrier plates (PerkinElmer) coated with laminin (Sigma, L2020; 15 μg/ml) using multi-channel pipet. For the experiment, 800,000 cells/mL stock in differentiation medium (DMEM/F12 supplemented with N2-MAX and B-27) was prepared and stored on ice for 2 h. Then, 40,000 cells were seeded per well in differentiation medium and allowed to attach for 30 min before addition of drug. For dose-response testing of all molecules except sterols, a 1000× compound stock in dimethyl sulphoxide (DMSO) was added to assay plates with 0.1 μL solid pin multi-blot replicators (V & P Scientific; VP 409), resulting in a final primary screening concentration of 1×. Sterols were added to cells as an ethanol solution (0.2% final ethanol concentration). Positive control wells (ketoconazole, 2.5 μM) and DMSO vehicle controls were included in each assay plate. Cells were incubated under standard conditions (37° C., 5% $CO_2$) for 3 days and fixed with 4% paraformaldehyde (PFA) in phosphate buffered saline (PBS) for 20 min. Fixed plates were washed with PBS (200 μL per well) twice, permeabilized with 0.1% Triton X-100 and blocked with 10% donkey serum (v/v) in PBS for 40 min. Then, cells were labelled with MBP antibodies (Abeam, ab7349; 1:200) for 16 h at 4° C. followed by detection with Alexa Fluor conjugated secondary antibodies (1:500) for 45 min. Nuclei were visualized by DAPI staining (Sigma; 1 μg/ml). During washing steps, PBS was added using a multi-channel pipet and aspiration was performed using Biotek EL406 washer dispenser (Biotek) equipped with a 96-well aspiration manifold.

High-Content Imaging and Analysis

Plates were imaged on the Operetta High Content Imaging and Analysis system (PerkinElmer) and a set of 6 fields captured from each well resulting in an average of 1200 cells being scored per well. Analysis (PerkinElmer Harmony and Columbus software) began by identifying intact nuclei stained by DAPI; that is, those traced nuclei that were larger than 300 μm$^2$ in surface area. Each traced nucleus region was then expanded by 50% and cross-referenced with the mature myelin protein (MBP) stain to identify oligodendrocyte nuclei, and from this the percentage of oligodendrocytes was calculated. In some experiments, the total process length of MBP+ oligodendrocytes was calculated as previously described.

High-Throughput Screening of 3,000 Bioactive Small Molecules

EpiSC-derived OPCs were grown and expanded in poly-ornithine and laminin-coated flasks before harvesting for plating. Cells were dispensed in differentiation media supplemented with Noggin (R&D Systems; 100 ng/ml), Neurotrophin 3 (R&D Systems; 10 ng/ml), cAMP (Sigma; 50 μM), and IGF-1 (R&D Systems; 100 ng/ml)) using a Biotek EL406 Microplate Washer Dispenser (Biotek) equipped with 5 μL dispense cassette (Biotek), into poly-D-lysine/laminin (Sigma, L2020; 4 μg/ml)-coated sterile, 384-well, CellCarrier ultra plates (PerkinElmer), to a final density of 12,500 cells per well and allowed to attach for 45 min before addition of drug. A 3 mM stock of bioactive compound library in dimethylsulphoxide (DMSO) were prepared in an Abgene storage 384-well plate (ThermoFisher Scientific; AB1055). These were added to assay plates using a 50 nL solid pin tool attached to Janus automated workstation (Perkin Elmer), resulting in a final screening concentration of 2 μM. Cells were incubated at 37° C. for 1 hour and then T3 (Sigma; 40 ng/ml) was added to all wells except negative controls, to which FGF (20 ng/ml) was added instead. Negative controls and T3-alone were included in each assay plate. After incubation at 37° C. for 72 h, cells were fixed, washed and stained similar to 96-well OPC assay protocol, although all the washing steps were performed using a Biotek EL406 Microplate Washer Dispenser (Biotek) equipped with a 96-well aspiration manifold. Cells were stained with DAPI (Sigma; 1 μg/ml) and MBP antibody (Abeam, ab7349; 1:100). Plates were imaged on the Operetta High Content Imaging and Analysis system (PerkinElmer) and a set of 4 fields captured from each well resulting in an average of 700 cells being scored per well. Analysis was performed as in High-Content Imaging and Analysis, above. All plates for the primary screen were processed and analyzed simultaneously to minimize variability. Molecules causing more than 20% reduction in nuclear count relative to DMSO control wells were removed from consideration, and hits were called on the basis of largest fold-increase in percentage of MBP+ oligodendrocytes relative to DMSO controls within the same plate. When selecting the leading hits for further experiments, molecules obtained in previous screens were omitted, including imidazole antifungals and clemastine.

GC/MS-Based Sterol Profiling

EpiSC-derived OPCs were plated at one million cells per well in PDL- and laminin-coated six well plates with differentiation media. After 24 hours, cells were dissociated with Accutase, rinsed with saline, and cell pellets were frozen. For sterol analyses, cells were lysed in methanol (Sigma-Aldrich) with agitation for 30 minutes and cell debris removed by centrifugation at 10,000 rpm for 15 min. Cholesterol-d7 standard (25,26,26,26,27,27,27-$^2$H$_7$-cholesterol, Cambridge Isotope Laboratories) was added before drying under nitrogen stream and derivatization with 55 µl of bis(trimethylsilyl)trifluoroacetamide/trimethylchlorosilane to form trimethylsilyl derivatives. Following derivatization at 60° C. for 20 minutes, 1 µl was analyzed by gas chromatography/mass spectrometry using an Agilent 5973 Network Mass Selective Detector equipped with a 6890 gas chromatograph system and a HP-5MS capillary column (60 m×0.25 µm×0.25 mm). Samples were injected in splitless mode and analyzed using electron impact ionization. Ion fragment peaks were integrated to calculate sterol abundance, and quantitation was relative to cholesterol-d7. The following m/z, ion fragments were used to quantitate each metabolite: cholesterol-d7 (465), FF-Mas (482), cholesterol (368), zymostenol (458), zymosterol (456), desmosterol (456, 343), 7-dehydrocholesterol (456, 325), lanosterol (393), lathosterol (458), 14-dehydrozymostenol (456). Calibration curves were generated by injecting varying concentrations of sterol standards and maintaining a fixed amount of cholesterol-D7. The human glioma cell line GBM528 was a gift of Jeremy Rich (Cleveland Clinic). Cortical organoids were generated as described previously.

CYP51 Enzymatic Assay

CYP51 enzymatic activity was measured using a reported method with slight modifications: rat CYP51 (Cypex, Inc.) was used as enzyme; reaction volume was 500 µl; reaction time was 30 minutes; lanosterol concentration was 50 µM; and reactions were quenched with 500 µl isopropanol. Finally, 15 µl of each reaction/isopropanol mixture was injected onto a SCIEX Triple Quad 6500 LC-MS/MS system using an APCI ion source in positive ion mode with a Shimadzu UFLC-20AD HPLC and a Phenomenex Kinetix C18XB 50×2.1×2.6 column at 40° C.

EBP Enzymatic Assay

EBP enzymatic activity was measured using a reported method with slight modifications: active EBP was obtained from mouse microsomes, inhibitors were added, zymostenol was added at a final concentration of 25 µM in a final reaction volume of 500 µl, and the reaction incubated at 37° C. for 2 h. Sterols were extracted using 3×1 ml hexanes, cholesterol-d7 was added to enable quantitation, and the pooled organics were dried (Na$_2$SO$_4$) and evaporated under nitrogen gas. Samples were then silylated and analyzed using GC/MS as described above.

siRNA Treatments

Cell-permeable siRNAs were obtained as pools of 4 individual siRNAs targeting mouse CYP51, or a non-targeting control (Accell siRNAs, Dharmacon). For differentiation analysis, cells were plated in 96-well plate (as detailed above) and treated with 1 µM pooled siRNA suspended in RNAse free water diluted in differentiation media (as detailed above). For sterol analysis cells were plated in a six-well plate at 300,000 cells per well in standard differentiation media supplemented with PDGF (R&D Systems, 20 ng/ml), neurotrophin 3 (R&D Systems; 10 ng/ml), cAMP (Sigma; 50 µM), IGF-1 (R&D Systems; 100 ng/ml), noggin (R&D Systems; 100 ng/ml). At 24 hours, 1 µM siRNA was added to the media. Cells were grown for three more days in siRNA containing media, with growth factor supplementation every 48 h, before harvesting and processing for GC/MS analysis as detailed above.

Focal Demyelination, Drug Treatment and Histological Analysis

Focal demyelination in the dorsal column of the spinal cord was induced by the injection of 1% LPC solution. 12 week old C57BL/6 female mice were anesthetized using isoflurane and T10 laminectomies were performed. 1 µl of 1% LPC was infused into the dorsal column at a rate of 15 µl/hour. At day 4, animals were randomized into treatment groups prior to treatment (2 animals were excluded due to surgical complications). Between days 4 and 11 post laminectomy, animals received daily injections of either vehicle or drug intraperitoneally. Drugs were dissolved in DMSO or corn oil and then diluted with sterile saline for injections such that final doses were 2 mg/kg for Tamoxifen and 10 mg/kg for Ifenprodil. This experiment was done in a blinded manner: compounds were coded to ensure the researchers performing the experiments were unaware of the treatment being administered to each animal. All animals were euthanized 12 days post laminectomy (n=4-6 per group). Mice were anesthetized using ketamine/xylazine rodent cocktail and then euthanized by transcardial perfusion with 4% PFA, 2% glutaraldehyde, and 0.1 M sodium cacodylate. Samples were osmicated, stained en bloc with uranyl acetate and embedded in EMbed 812, an Epon-812 substitute (EMS). 1 µm sections were cut and stained with toluidine blue and visualized on a light microscope (Leica DM5500B). The number of myelinated axons per unit areas was counted from sections in the middle of each lesion and then averaged over each treatment group. A Mann-Whitney statistical analysis was performed to assess statistical significance.

Analysis of Mouse Brain Sterol Levels

Ten to twelve week old male C57BL/6 mice were injected with 2 mg/kg tamoxifen, 10 mg/kg ifenprodil, or 10 mg/kg miconazole dissolved in corn oil (tamoxifen) or DMSO (ifenprodil, miconazole) in sterile saline daily for three days. Mice were anaesthetized with isoflurane and perfused with phosphate buffered saline to remove blood from the brain. Brains were collected and flash frozen using liquid nitrogen. The samples were pulverized and 50-100 milligrams of tissue were collected for further processing. A modified Folch protocol was used for extraction of sterols. Briefly, samples were resuspended in a 2:1 chloroform/methanol mixture and homogenized. Cell debris was removed by centrifugation at 4000 g for 10 min. The solution was dried under air and resuspended in hexane with a cholesterol-D7 standard and dried again. Lipids were derivatized with 70 µl of bis(trimethylsilyl)trifluoroacetamide; 2 µls were injected and analyzed by GC/MS as described above.

Estrogen-Dependent Cell Proliferation Assay

Estrogen-dependent cell proliferation was measured as previously described with minor modifications. After growth in estrogen-free media (Phenol red-free RPMI supplemented with 10% charcoal stripped fetal bovine serum) for 5 days, cells were seeded at 2,500 cells/well into 96 well plates. The following day 3× drug containing media was added to triplicate wells and cells were allowed to grow for an additional 5 days at 37° C. in standard a 5% CO, humidified incubator. Total DNA per well was measured using an adaptation of the method of Labarca and Paigen. At this time media was removed, cells were washed one time with 0.25×PBS and 100 ul of distilled water was added. Plates were frozen and thawed to enhance cell lysis and 200 µl of 10 µg/ml Hoechst 33258 (Sigma-Aldrich, St. Louis, MO.) in 2M NaCl, 1 mM EDTA, 10 mM Tris-HCl pH 7.4 was added. After incubation at room temperature for 2 hours, plates were read in a SpectraMax i3 fluorescent plate reader (Molecular Devices, Sunnyvale, CA) with excitation at 360 nm and emission at 460 nm. All values were converted to microgram DNA per well using a standard curve derived from purified salmon testes DNA.

Oligodendrocyte Formation and Imaging on Electrospun Microfibers

A 12-well plate containing Mimetex aligned scaffold (microfiber plate, AMSBIO, AMS.TECL-006-1X, Electrospun poly-L-lactide Scaffold, 2 µM fibre diameter cell crown inserts) was prepared as previously described. Briefly, inserts were sterilized with 70% ethanol and washed with PBS before being coated with polyornithine and laminin. After laminin coating, 100,000 cells/mL of EpiSC-derived OPCs were plated in differentiation medium. After 24 h the media was replaced with fresh media containing small molecule treatments. Every 48 h the media was replaced with fresh compound containing media for a total of 14 days. Plates were fixed with 4% PFA, permeabilized with 0.1% Triton X-100, and blocked with 10% donkey serum (v/v) in PBS for 60 min. Plates were stained for MBP (Abcam, ab7349; 1:100) and DAPI staining (Sigma; 5 µg/ml). After staining, the inserts were moved into new 12-well plate and covered with 2 mL of PBS before imaging in Operetta high content Imaging and analysis system. Plates were imaged on the Operetta High Content Imaging and Analysis system (PerkinElmer) and a set of 8 fields captured from each well resulting in an average of 45,000 cells being scored per well. Analysis (PerkinElmer Harmony and Columbus software) identified intact nuclei stained by DAPI and calculated the MBP signal intensity per cell per well. Microfiber insert tracking images were taken using a Leica DMi8 with a 20× Dry/NA 0.40 objective. Microfiber plate inserts were mounted using Flouromount-G (SouthernBiotech) and allowed to partially harden before coverslips were added and the insert ring was removed. Confocal images were obtained on a Leica SP8 confocal scanning microscope, with 40× oil/NA 1.30 objective. Confocal stacks of 0.336 m z-steps were taken at 1024×1024. Each fluorophore was excited sequentially and all contrast and brightness changes were applied consistently between images.

CYP51 qPCR

Cells were plated at 500,000 cells per well in a six-well plate and were grown in standard differentiation media supplemented with PDGF, neurotrophin 3, cAMP, TGF-1, and noggin for four days as described above. At 24 hours, cells were treated with 1 µM siRNA. Growth factors were added every 48 hours. After three days of siRNA treatment, RNA was isolated with the RNeasy Mini Kit (Qiagen), and cDNA was made using High-Capacity RNA-to-cDNA™ Kit (Applied Biosystems). Exon spanning primers for ActinB (Thermo-Fisher, Taqman, Mm02619580_g1) and CYP51 (Thermo-Fisher, Taqman, Mm00490968_m1) were used for detection of relative RNA levels by quantitative real time PCR (Applied Biosystems, 7300 Realtime PCR system). Cycle time and outliers were calculated using Applied Biosystems' 7300 System Sequence Detection Software version 1.4.

Muscarinic Receptor Antagonism Assay

GeneBLAzer M1-NFAT-bla CHO-K1 cells (or M3- or M5-NFAT-bla CHO-K1 cells)(ThermoFisher) were thawed into Assay Media (DMEM, 10% dialyzed FBS, 25 mM HEPES pH 7.3, 0.1 mM NEAA). 10,000 cells/well were added to a 384-well TC treated assay plate and incubated 16-24 h at 37° C. 4 µl of a 10× stock of antimuscarinic molecules was added to the plate and incubated 30 min 4 µl of 10× control agonist Carbachol at the pre-determined EC80 concentration was added to wells containing antimuscarinic molecules. The plate was incubated 5 h and 8 µl of 1 µM Substrate+Solution D Loading Solution was added to each well and the plate was incubated 2 h at room temperature before reading on a fluorescence plate reader.

Results

High-throughput phenotypic screening has emerged as a promising route to identifying small molecules that enhance the generation of new oligodendrocytes from OPCs. Multiple groups have identified screening hits that show functional benefit in animal models of demyelination. However, translation of these findings to humans has been impeded by lack of knowledge of the functional targets of these molecules in enhancing oligodendrocyte formation. Previously we used mouse pluripotent stem cell-derived OPCs to identify structurally-diverse imidazole antifungal drugs as a robust class of hits that stimulate the generation of new mouse and human oligodendrocytes and enhance remyelination in mouse disease models. Imidazole antifungals are known to mediate their effects in yeast by inhibiting sterol 14-α-demethylase (CYP51), an essential enzyme for sterol biosynthesis in both fungal and mammalian cells. However, the mechanism of action of imidazole antifungal drugs in OPCs has remained undefined.

Figure 1B:
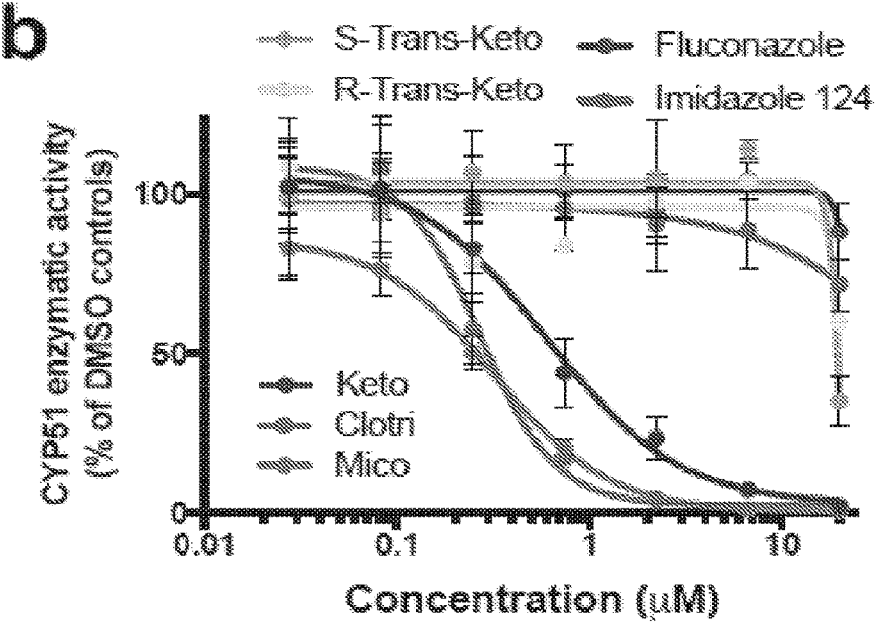
Figure 1C:
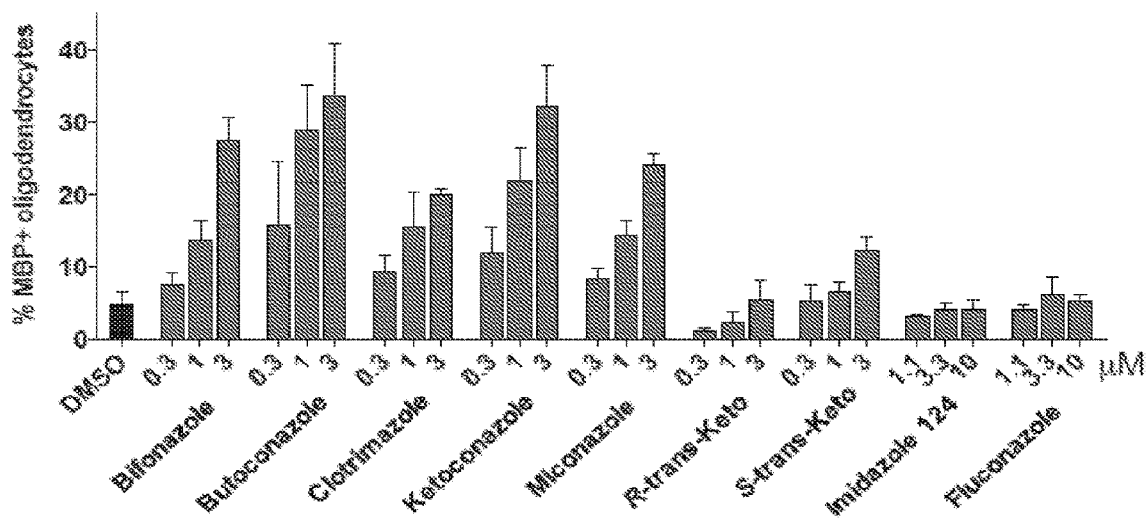
Figure 1D:
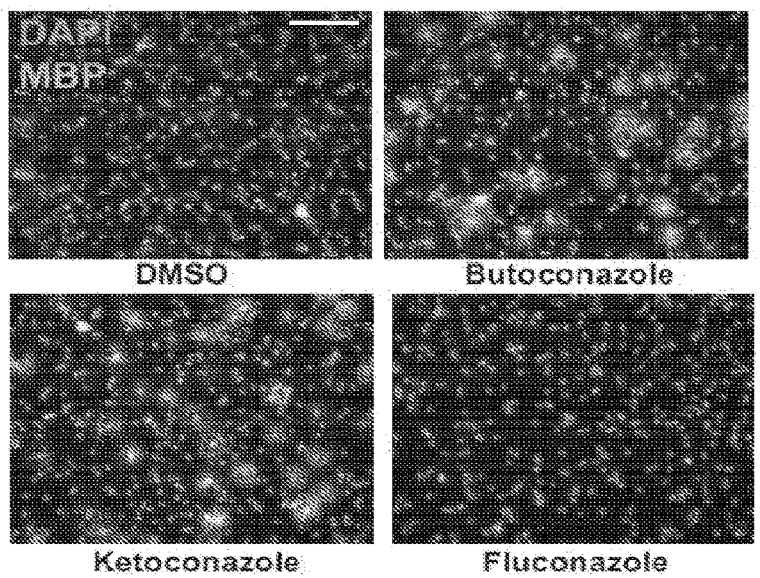
Figure 1E:
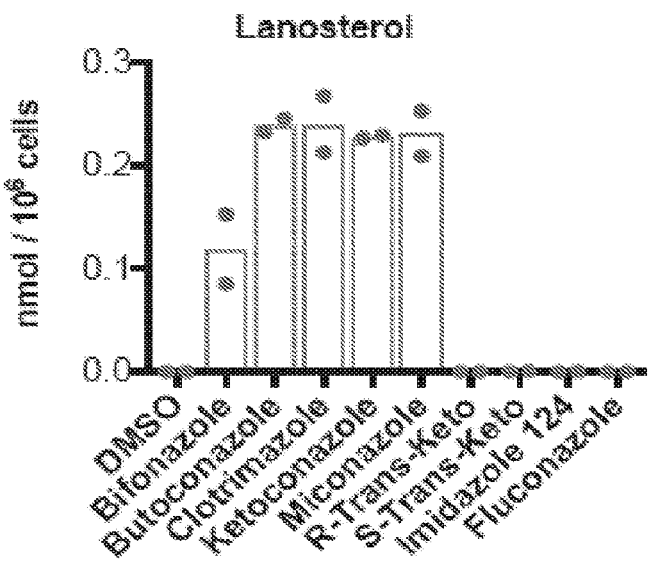
Figure 1F:
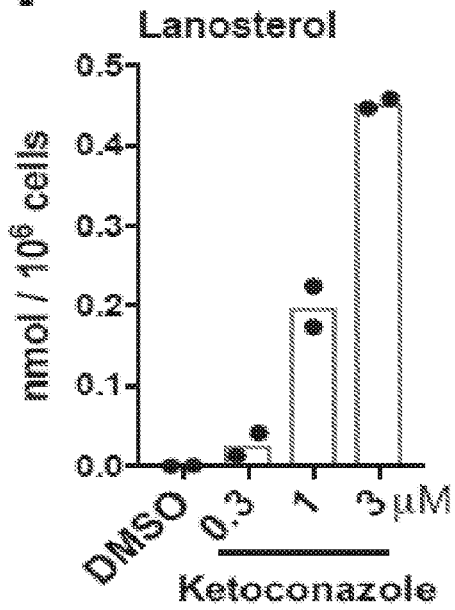

To test whether CYP51 inhibition is responsible for the effect of imidazole antifungal drugs in promoting the generation of oligodendrocytes from OPCs, we assembled a collection of nine azole-containing molecules with wide-ranging potency for mammalian CYP51 inhibition (FIG. 1A). We used a mass spectrometry-based biochemical assay to confirm that FDA-approved imidazole antifungals (miconazole, clotrimazole, and ketoconazole) showed clear inhibition of rodent CYP51 in vitro with similar $IC_{50}$ values ranging from 300-700 nM (FIG. 1B). Three close analogs of ketoconazole known to lack antifungal activity were strikingly less effective at inhibiting mammalian CYP51: namely, the R-trans and S-trans diastereomers of ketoconazole and a truncated analog, Imidazole 124 (FIG. 1A,B). Additionally, we confirmed that the triazole antifungal fluconazole, which selectively targets yeast CYP51, did not inhibit mammalian CYP51 in vitro (FIG. 1B). For each molecule in our panel, potency for inhibition of mammalian CYP51 in vitro paralleled the enhanced formation of mature myelin basic protein-positive (MBP+) oligodendrocytes from mouse epiblast stem cell-derived OPCs (FIG. 1C,D). These findings suggest that imidazole antifungals act by their canonical target, CYP51, to enhance oligodendrocyte formation.

Since CYP51 is known to function in cholesterol biosynthesis in mammalian cells, we assessed functional inhibition of CYP51 in OPCs using gas chromatography/mass spectrometry (GC/MS) to measure cellular sterol levels. Mouse OPCs were treated with each azole-containing molecule for 24 hours, at which point they were lysed for analysis by GC/MS and levels of lanosterol, the substrate of CYP51, as well as downstream cholesterol levels were quantified. Lanosterol accumulated in OPCs only after treatment with each of five active imidazole antifungals, mirroring the effects of these molecules on CYP51 function in our biochemical assay (FIGS. 1B,E, FIG. 5A). Notably, to eliminate potential cell source or assay artifacts, we confirmed all effects of small molecules on oligodendrocyte formation and sterol levels using a second, independently isolated batch of mouse epiblast stem cell-derived OPCs (Extended Data FIG. 1b-d; see Methods for details of OPC derivations). Additionally, the effects of azole molecules on oligodendrocyte formation and lanosterol levels were confirmed using primary mouse OPCs (FIG. 5E,F), using an orthogonal image quantitation approach measuring total process length (FIG. 1G), and using PLP1 as a second marker of oligodendrocyte formation (FIG. 1H). For ketoconazole, the dose-response for accumulation of lanosterol closely resembled the dose-response for enhanced oligodendrocyte formation (compare FIG. 1F, 1C; FIG. 5I, 5B). The tight correlation between CYP51 inhibition and enhanced formation of oligodendrocytes among these highly structurally diverse azole-containing small molecules suggests that CYP51 is the relevant target in OPCs.

We next used genetic manipulation and metabolite supplementation to independently confirm the role of CYP51 in oligodendrocyte formation. We used cell-permeable siRNA reagents to deplete CYP51 transcript levels in OPCs by 80% (FIG. 1G). Suppression of CYP51 led to significant accumulation of lanosterol and enhanced formation of MBP+ oligodendrocytes, although this effect was smaller than seen for ketoconazole treatment, likely due to the siRNA treatment's slower kinetics and incomplete target suppression (FIG. 1H,I, FIG. 5J; confirmed in an independent OPC batch in FIG. 5K,L). Additionally, we treated OPCs directly with purified lanosterol and observed enhanced formation of MBP+ oligodendrocytes in a dose-responsive fashion (FIG. 1J, FIG. 5M, confirmed in FIG. 5N). This finding suggests that accumulation of sterol intermediates may play a direct role in enhancing oligodendrocyte formation from OPCs.

Figure 2A:
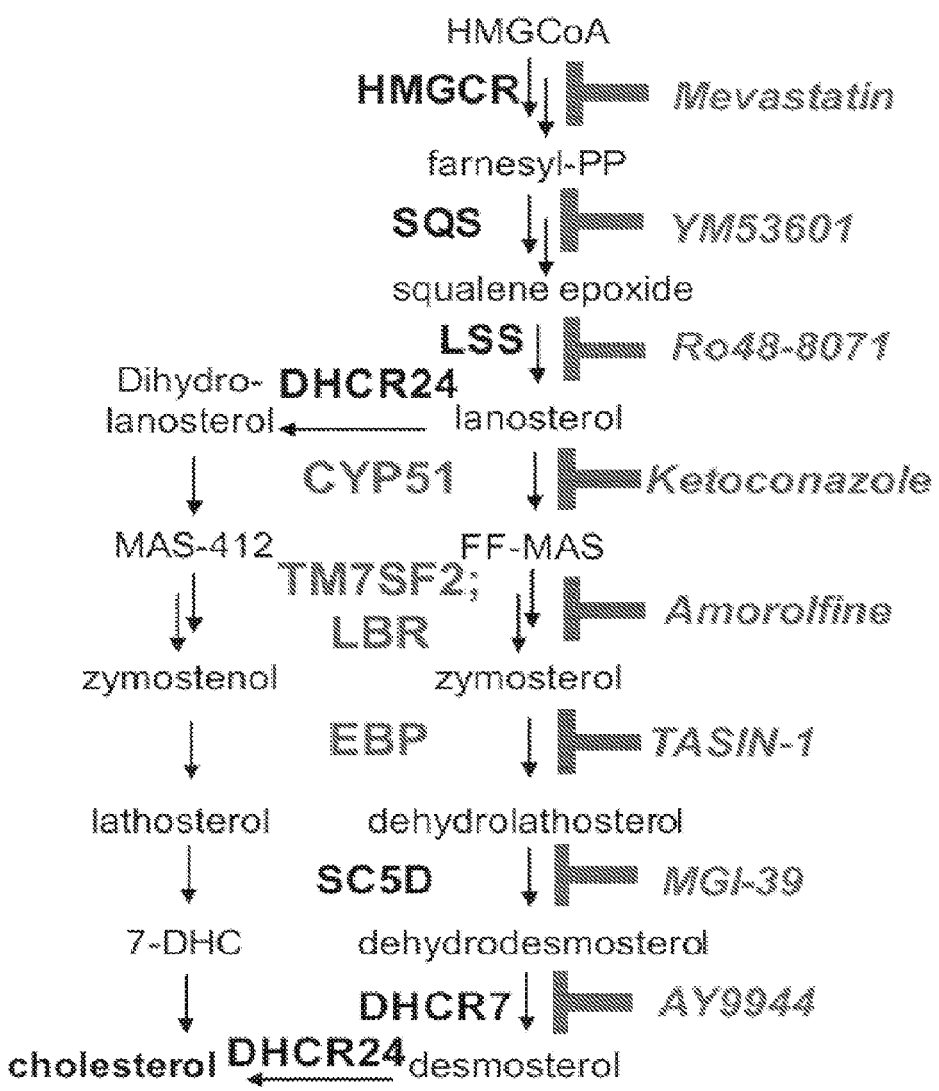
FIGS. 2(A-D) illustrate a schematic drawing and graphs showing the effect of small-molecule inhibition of enzymes in the cholesterol biosynthesis pathway on enhancing oligodendrocyte formation. A) Abbreviated cholesterol biosynthesis pathway, with intermediate metabolites and selective inhibitors labeled. B) Percentage of MBP+ oligodendrocytes generated from OPCs at 72 h following treatment with the indicated pathway inhibitors. n=4 replicates per condition, with >1,000 cells analyzed per replicate. C) GC/MS-based quantitation of 14-dehydrozymostenol levels in OPCs treated 24 h with the indicated doses of amorolfine or TASIN-1. n=2 replicates per condition. D) Percentage of MBP+ oligodendrocytes generated from OPCs at 72 h following treatment with the indicated purified sterol intermediates. n=4 replicates per condition, with >1,000 cells analyzed per replicate.
Figure 2B:
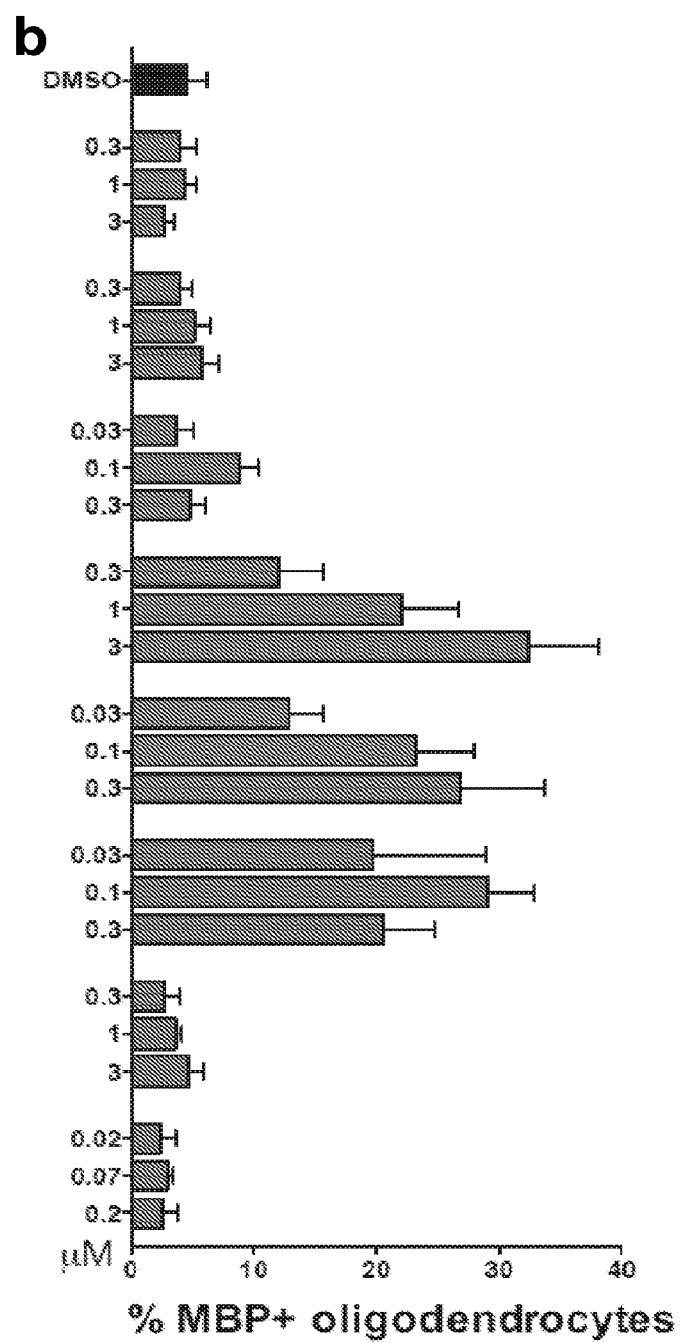
Figure 7E:
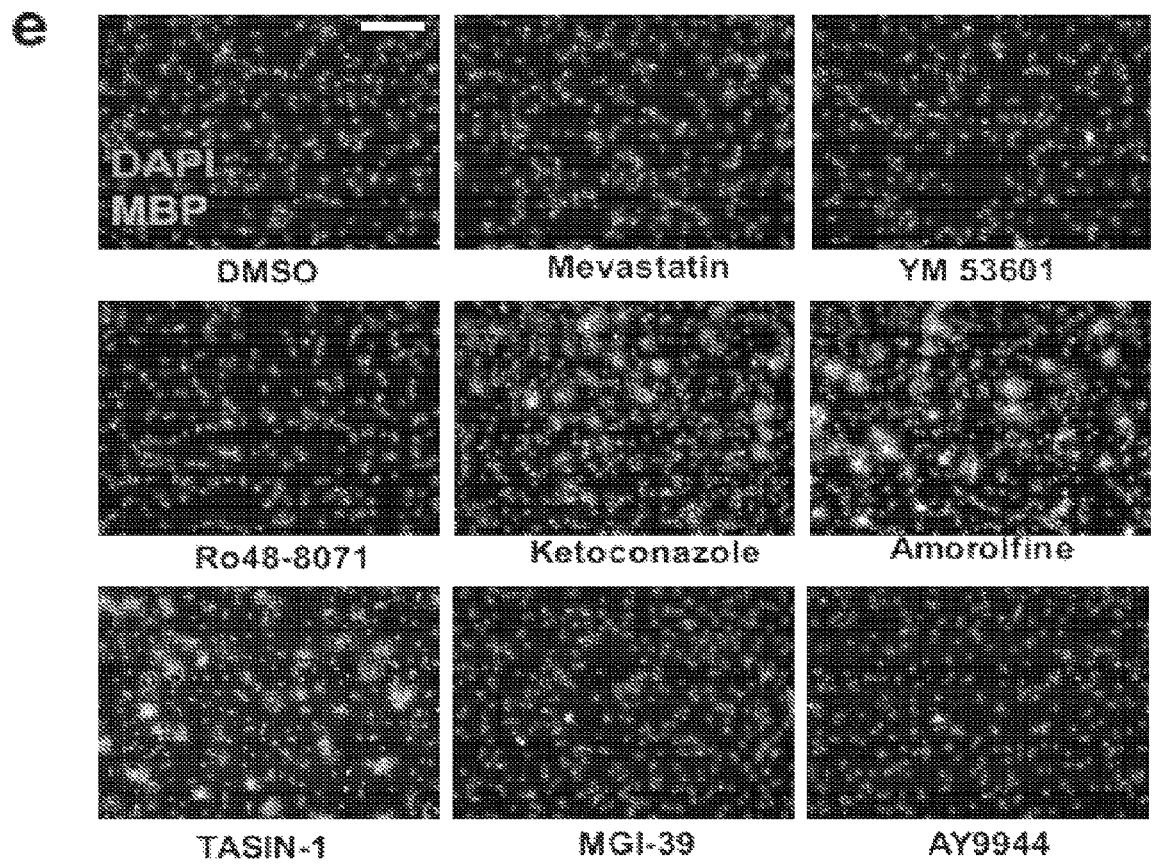

Since CYP51 inhibition was sufficient to induce the formation of oligodendrocytes, we used a chemical genetics approach to test whether modulation of other steps in cholesterol biosynthesis has a similar effect. Cholesterol biosynthesis is a long, intricately regulated pathway for which many high-quality small-molecule probes and approved drugs are available (FIG. 2A, FIG. 6). We collected selective small-molecule inhibitors of eight enzymes throughout the cholesterol biosynthesis pathway and assessed their impact on oligodendrocyte generation and sterol levels in OPCs. We confirmed that inhibitors targeting sterol-metabolizing enzymes selectively caused the accumulation of the expected upstream sterol intermediates in OPCs, and for all probes we confirmed reduced levels of one or both of the pathway's terminal products, desmosterol and cholesterol (FIG. 7A-D). We evaluated the effects of each of these eight pathway inhibitors on OPC differentiation to oligodendrocytes. Only molecules targeting CYP51 (ketoconazole), sterol 14-reductase (amorolfine), and EBP (TA-SIN-1) enhanced formation of MBP+ oligodendrocytes, whereas inhibitors of the five other pathway enzymes were ineffective (FIG. 2B, FIG. 7E, confirmed in Extended Data FIG. 3f, validated in primary OPCs in FIG. 7G,H). Treatments had minimal effect on total cell number during the 3 d assay (FIG. 7E). Amorolfine and TASIN-1 were effective at doses below 100 nM, with potency for accumulation of 14-dehydrozymostenol and zymostenol mirroring potency for enhancement of oligodendrocyte formation (FIG. 2C, FIG. 7I). Direct treatment of OPCs with 14-dehydrozymostenol and zymostenol enhanced the formation of MBP+ oligodendrocytes, whereas other sterols associated with steps downstream of EBP, including cholesterol itself, were ineffective (FIG. 2D, FIG. 7J,K,). In total, this chemical genetic analysis suggests that inhibition of the cholesterol biosynthesis pathway within a limited window spanning CYP51 to EBP is sufficient for enhancing the formation of oligodendrocytes. The mechanism of this effect is not mediated by simple reduction of sterol levels as statin drugs and various other pathway inhibitors that we confirmed as depleting cholesterol and desmosterol levels did not modulate OPC differentiation (FIG. 2B, FIG. 7A,B). Notably, the sterol intermediates that accumulate following inhibition of steps between CYP51 and EBP are unified by the presence of an $\Delta 8,9$ unsaturation, suggesting a chemical basis for their functional effect to enhance oligodendrocyte formation (FIG. 6).

Figure 8F:
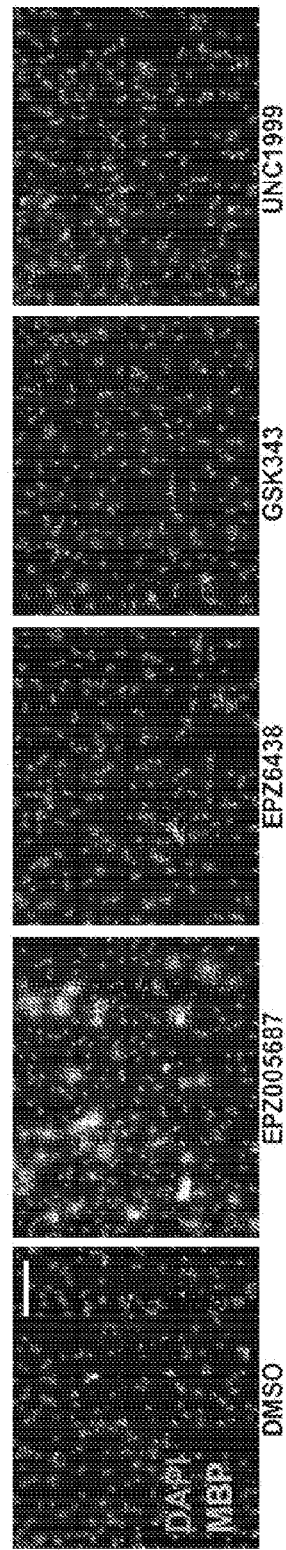
Figure 8I:
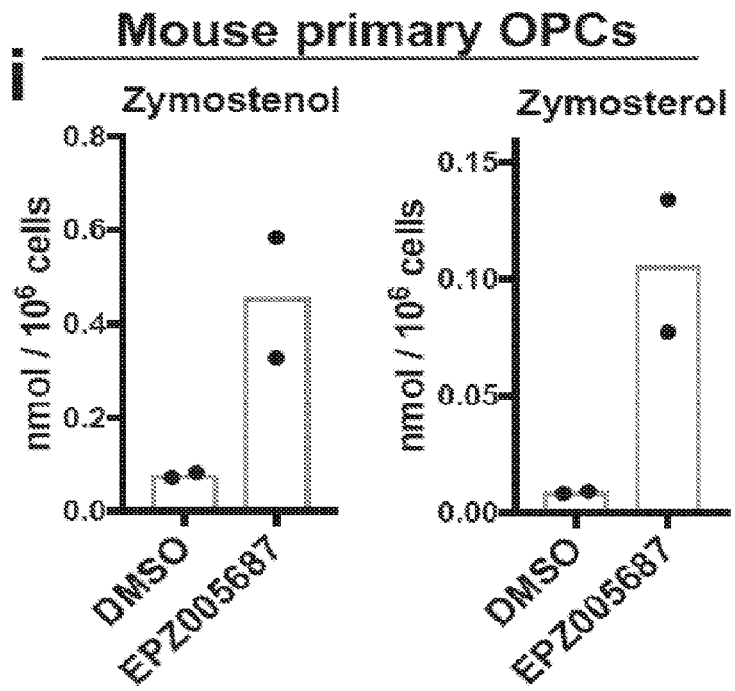

In parallel, we executed a screen of over 3,000 bioactive small molecules and approved drugs at a uniform dose of 2 µM (FIG. 8A). This library contains many approved drugs screened previously, as well as a wide range of non-approved drug candidates and well-annotated chemical probes. Among our hits, we obtained nine imidazole antifungals as well as other molecules previously annotated as enhancing OPC differentiation, including clemastine (Extended Data Table 1). We also identified many confirmed hits with known targets that did not cluster into easily discernible categories (Extended Data Table 1). Among molecules not previously reported to modulate OPC differentiation, our top hit was EPZ005687, an inhibitor of the histone methyltransferase EZH2. EPZ005687 enhanced oligodendrocyte formation in both our mouse epiblast stem cell-derived OPCs and mouse primary OPCs (FIG. 8B-F). Surprisingly, we verified that three structurally analogous EZH2 inhibitors had no effect on OPC differentiation, suggesting that EPZ005687 had an idiosyncratic off-target effect beyond EZH2 (FIGS. 8C,D,F). We examined the effects of these four EZH2 inhibitors in our GC/MS-based sterol profiling assay and found that EPZ005687 uniquely caused accumulation of zymosterol and zymostenol in OPCs, indicative of EBP inhibition (FIGS. 8G-I). Among these four closely-related EZH2 inhibitors, structural differences relating to the presence of the morpholine and indazole rings appear to enable EPZ005687 alone to inhibit EBP in OPCs and enhance the formation of oligodendrocytes.

TABLE 1

Enhancers of oligodendrocyte formation identified by screening of a 3,000-molecule bioactives library

| Name | Total Cells | % Oligos | MW | DMSO % oligos_Mean | DMSO % oligos_StdDev | cell viability (% relative to DMSO) | fold-change in % MBP + oligodendrocytes |
|---|---|---|---|---|---|---|---|
| Isoconazole nitrate | 584 | 53.25 | 479.14 | 7.95 | 3.66 | 106.98 | 6.70 |
| EPZ005687 | 610 | 50.00 | 539.67 | 8.47 | 2.61 | 91.36 | 5.90 |

TABLE 1-continued

Enhancers of oligodendrocyte formation identified by screening of a 3,000-molecule bioactives library

| Name | Total Cells | % Oligos | MW | DMSO % oligos_Mean | DMSO % oligos_StdDev | cell viability (% relative to DMSO) | fold-change in % MBP + oligodendrocytes |
|---|---|---|---|---|---|---|---|
| Clotrimazole | 666 | 27.93 | 344.85 | 4.75 | 2.75 | 122.50 | 5.88 |
| Ketoconazole | 847 | 52.77 | 531.44 | 9.33 | 3.87 | 121.51 | 5.65 |
| Butoconazole nitrate | 809 | 46.85 | 474.79 | 8.92 | 2.63 | 122.03 | 5.25 |
| Sertaconazole nitrate | 777 | 39.38 | 500.78 | 7.52 | 1.87 | 134.49 | 5.23 |
| Pyrimethamine | 604 | 43.87 | 248.71 | 8.92 | 2.63 | 91.11 | 4.92 |
| Ifenprodil Tartrate | 693 | 41.41 | 475.53 | 8.47 | 2.61 | 103.79 | 4.89 |
| Varenicline tartrate | 783 | 22.86 | 361.36 | 4.75 | 2.75 | 144.02 | 4.81 |
| Raloxifene HCl | 777 | 35.01 | 510.04 | 7.29 | 3.37 | 114.37 | 4.80 |
| Hydroxyzine 2HCl | 896 | 40.63 | 447.83 | 8.47 | 2.61 | 134.19 | 4.80 |
| Ziprasidone HCl | 1003 | 34.10 | 449.40 | 7.29 | 3.37 | 147.64 | 4.68 |
| Bifonazole | 820 | 40.98 | 310.39 | 8.92 | 2.63 | 123.69 | 4.59 |
| SB408124 | 704 | 39.63 | 356.37 | 8.92 | 2.63 | 106.19 | 4.44 |
| Sulconazole Nitrate | 700 | 37.57 | 460.76 | 8.47 | 2.61 | 104.84 | 4.44 |
| Pentamidine isethionate | 758 | 41.29 | 592.69 | 9.33 | 3.87 | 108.75 | 4.42 |
| Clemastine fumarate | 449 | 20.49 | 459.97 | 4.75 | 2.75 | 82.59 | 4.31 |
| Raltegravir (MK-0518) | 768 | 38.02 | 444.42 | 8.92 | 2.63 | 115.85 | 4.26 |
| Fenticonazole Nitrate | 687 | 35.66 | 518.41 | 8.92 | 2.63 | 103.63 | 4.00 |
| Mubritinib (TAK 165) | 779 | 31.45 | 468.47 | 7.95 | 3.66 | 142.71 | 3.95 |
| Pramoxine HCl | 755 | 32.98 | 329.86 | 8.47 | 2.61 | 113.08 | 3.89 |
| TMB-8 hydrochloride | 758 | 18.47 | 432.00 | 4.75 | 2.75 | 139.42 | 3.89 |
| (±)-Vesamicol | 821 | 34.23 | 295.86 | 8.84 | 3.16 | 112.02 | 3.87 |
| Clotrimazole | 748 | 34.36 | 344.84 | 8.92 | 2.63 | 112.83 | 3.85 |
| Fulvestrant | 758 | 18.21 | 606.79 | 4.75 | 2.75 | 139.42 | 3.83 |
| Raloxifene hydrochloride | 924 | 33.33 | 510.06 | 8.84 | 3.16 | 126.07 | 3.77 |
| Praziquantel | 728 | 33.24 | 312.41 | 8.92 | 2.63 | 109.81 | 3.72 |
| Ziprasidone hydrochloride monohydrate | 851 | 32.78 | 467.42 | 8.84 | 3.16 | 116.11 | 3.71 |
| LY2784544 | 480 | 28.75 | 469.94 | 7.95 | 3.66 | 87.93 | 3.62 |
| ifenprodil tartrate | 739 | 33.69 | 801.00 | 9.33 | 3.87 | 106.02 | 3.61 |
| L-745,870 hydrochloride | 647 | 32.61 | 363.29 | 9.33 | 3.87 | 92.82 | 3.49 |
| Hexahydro-sila-difenidol hydrochloride, p-fluoro analog | 654 | 26.76 | 386.03 | 7.68 | 3.55 | 95.08 | 3.49 |

We further examined the top 10 confirmed hits after EPZ005687 (exclusive of imidazole antifungals and other molecules identified in previously published screens) and found that all 10 induced altered sterol profiles at the screening dose (FIGS. 3A-B, FIGS. 9A-B). Seven molecules inhibited EBP, two molecules inhibited sterol 14-reductase activity, and one molecule (fulvestrant) targeted CYP51 (FIGS. 9C-D). Four of these molecules have previously been shown to modulate sterol 14-reductase or EBP activity in CNS-derived cells: ziprasidone, ifenprodil, hydroxyzine, and raloxifene. Among 10 library molecules that we independently confirmed do not affect OPC differentiation to oligodendrocytes at the screening dose, none enhanced levels of 8,9-unsaturated sterol intermediates (FIGS. 3A-B, FIGS. 9A-B). These data show that modulation of sterol synthesis appears to be a dominant mechanism-of-action for enhancing the formation of oligodendrocytes among small molecules identified by high-throughput screening.

Figure 9H:
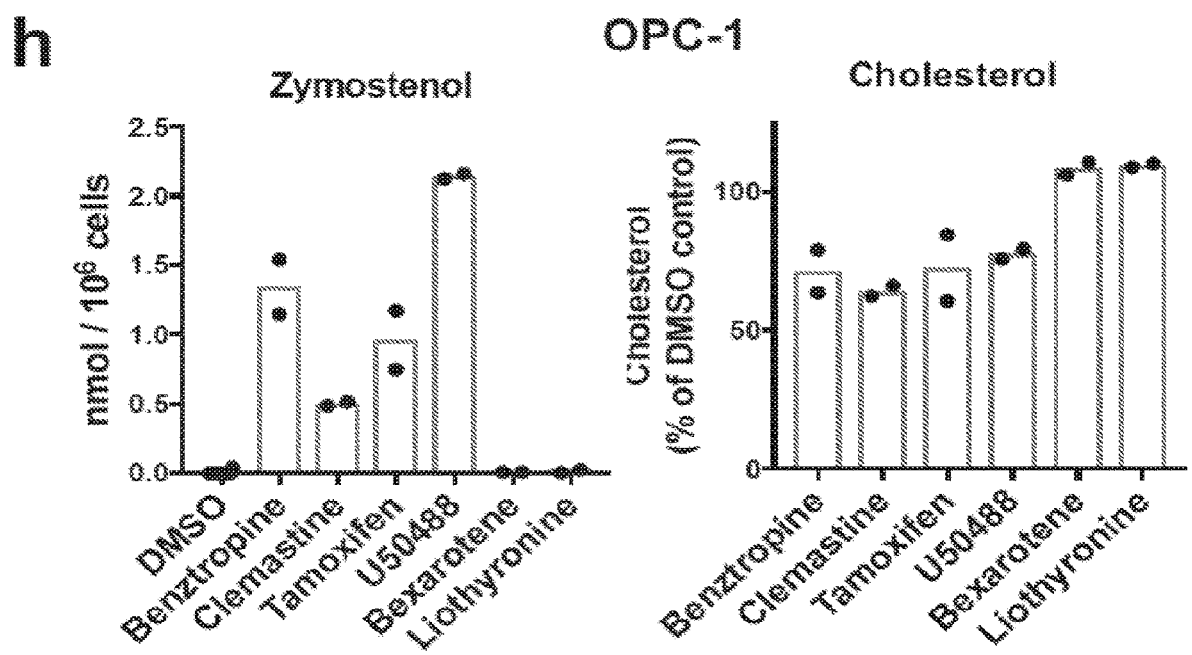

Given the frequency of cholesterol pathway modulators within our top screening hits, we assessed whether any previously-reported enhancers of remyelination might also induce sterol intermediate accumulation. We assembled a collection of molecules reported to induce OPC differentiation through a variety of canonical targets: benztropine (muscarinic receptor), clemastine (H1 receptor and muscarinic receptor), tamoxifen (estrogen receptor), U50488 (κ-opioid receptor), bexarotene (RXR), and liothyronine (thyroid hormone receptor). We identified the dose at which each molecule shows near-maximal upregulation of oligodendrocyte formation and then evaluated each molecule in our GC/MS sterol profiling assay (FIGS. 9E-G). Benztropine, clemastine, tamoxifen, and U50488 induced accumulation of zymostenol and zymosterol and decreased basal sterol levels, indicative of inhibition of EBP (FIGS. 3C-D, FIG. 9H). Tamoxifen has been shown previously to inhibit EBP in a biochemical assay, in cell culture models, and in cancer patients undergoing chemotherapy. By contrast, liothyronine and bexarotene showed minimal effects on sterol levels, consistent with their known functions as regulators of transcription factor function and confirming that many, but not all, treatments that enhance oligodendrocyte formation cause sterol intermediate accumulation.

Inhibition of EBP in OPCs following treatment with clemastine, tamoxifen, or other small molecules could result from direct targeting of EBP or could reflect a downstream consequence of each molecule inhibiting its canonical protein target. We assessed direct inhibition of EBP in vitro using a GC/MS-based biochemical assay of EBP enzymatic activity. We observed clear inhibition by the selective EBP inhibitor TASIN-1 as well as by benztropine, clemastine, tamoxifen, and U50488, with more potent cellular EBP inhibitors showing a greater magnitude of inhibition (FIG. 3E). We also annotated two molecules identified in our bioactives screen, EPZ005687 and hydroxyzine, as directly inhibiting EBP enzymatic activity in this biochemical assay, suggesting that many enhancers of oligodendrocyte formation directly target EBP in OPCs.

We sought additional evidence that muscarinic receptor antagonists and selective estrogen receptor modulators (SERMs) mediate enhanced oligodendrocyte formation in OPCs by acting on EBP as their functional target. Although clemastine and benztropine have been validated as inducers of OPC differentiation to oligodendrocytes, previous work suggested that many other muscarinic receptor antagonists do not share this functional property. Using our bioactives screening data, we selected four muscarinic receptor antagonists with varying isoform selectivity and independently confirmed that all four do not enhance MBP+ oligodendrocyte generation at 2 μM (FIGS. 10A-C). However, in independent cellular activity assays also performed at 2 μM, these four molecules and clemastine showed comparable, near-complete inhibition of the of the muscarinic receptor M1, M3, and M5 isoforms, suggesting that muscarinic receptors may not be the functional target in OPCs (FIG. 10D). In contrast to clemastine and benztropine, which enhance 8,9-unsaturated sterol accumulation and directly inhibit EBP enzymatic activity, profiling of cellular sterol levels for the muscarinic receptor antagonists that do not enhance oligodendrocyte formation revealed no effect on zymostenol or other sterol intermediates in OPCs, and no inhibition of EBP was observed in an enzymatic activity assay (FIG. 3E, FIGS. 10E-F). These findings suggest that only muscarinic receptor antagonists that inhibit EBP can enhance formation of oligodendrocytes.

The ability to inhibit EBP in OPCs also predicts enhanced formation of oligodendrocytes among selective estrogen receptor modulators (SERMs). Multiple SERMs have been shown to potently target EBP in other cell types, with the tertiary amine functionality of SERMs like tamoxifen and toremifene believed to mimic EBP's sterol C8 cation-like transition state when protonated at physiological pH. We confirmed that toremifene inhibited EBP and enhanced MBP+ oligodendrocyte generation over a wide dose range (FIG. 10G-L). Ospemifene is also an FDA-approved SERM that is structurally identical to toremifene except for the substitution of a primary alcohol for toremifene's tertiary amine functionality. This change prevents ospemifene from bearing a positive charge at physiological pH and should eliminate EBP inhibitory activity. Indeed, ospemifene did not inhibit EBP in OPCs and did not enhance differentiation to MBP+ oligodendrocytes (FIG. 10G-L). Notably, toremifene and ospemifene demonstrated comparable anti-estrogen effects in an independent estrogen-dependent cell proliferation assay, suggesting that among structurally near-identical SERMs the ability to inhibit EBP, and not modulation of the estrogen receptor, predicts enhanced oligodendrocyte formation (FIG. 10L).

Because our results suggest that sterol modulation is a shared function of many (but not all) compounds that enhance oligodendrocyte formation, we tested the potential for combinations of small molecules to show additive or non-additive effects. Combining the thyroid hormone agonist liothyronine with a range of sterol-modulating OPC differentiation-inducing treatments produced additive effects on oligodendrocyte formation, indicating that these molecules likely function by mechanisms other than thyroid hormone receptor signaling to enhance oligodendrocyte generation (FIGS. 11A,B). In contrast, combinations of ketoconazole at a maximally effective dose with any of four previously-reported enhancers of OPC differentiation (benztropine, clemastine, tamoxifen, and U50488) did not enhance differentiation above levels seen for ketoconazole alone (FIG. 3F, FIG. 11C). This non-additive effect is consistent with these molecules sharing 8,9-unsaturated sterol accumulation as a common mechanism for induction of oligodendrocyte formation. By inhibiting pathway flux at CYP51 with ketoconazole, inhibitors of EBP can no longer cause further sterol accumulation or enhance oligodendrocyte formation.

Since our in vitro OPC assays only model the initial differentiation event into oligodendrocytes, we next tested whether sterol pathway modulation also enhanced subsequent oligodendrocyte maturation and myelination in vitro and in vivo. We cultured OPCs for 14 days on electrospun microfibers to assess the effects of sterol pathway modulators on oligodendrocytes' ability to track and wrap along axon-like substrates. Ketoconazole (CYP51), amorolfine (sterol 14-reductase), and TASIN-1 (EBP), each of which function to accumulate sterol intermediates in OPCs, significantly enhanced MBP+ oligodendrocyte tracking along and wrapping of the microfibers (FIGS. 12A-C). Inhibition of other enzymes, up- or downstream in the pathway, had no effect on oligodendrocyte maturation and ensheathment of microfibers (FIGS. 12A-B).

Previously we established that the imidazole antifungal miconazole, which targets CYP51, penetrates the mouse blood brain barrier and enhances remyelination in mouse models of demyelination. To assess whether inhibition of other sterol pathway enzymes may also enhance remyelination in vivo, we selected one inhibitor of sterol 14-reductase (ifenprodil) and one inhibitor of EBP (tamoxifen) for further evaluation. Both ifenprodil and tamoxifen are known to cross the mouse blood brain barrier. We first used GC/MS-based sterol profiling to test target engagement in vivo in the CNS. Miconazole (10 mg per kg (body weight)), ifenprodil (10 mg per kg), and tamoxifen (2 mg per kg) each induced significant accumulation of 8,9-unsaturated sterols in the brain of adult wild type mice following 3 days of intraperitoneal dosing (FIG. 4A). These data demonstrate that the sterol modulators miconazole, ifenprodil, and tamoxifen can functionally engage CYP51, sterol 14-reductase, and EBP respectively in the mouse CNS.

Figure 4C:
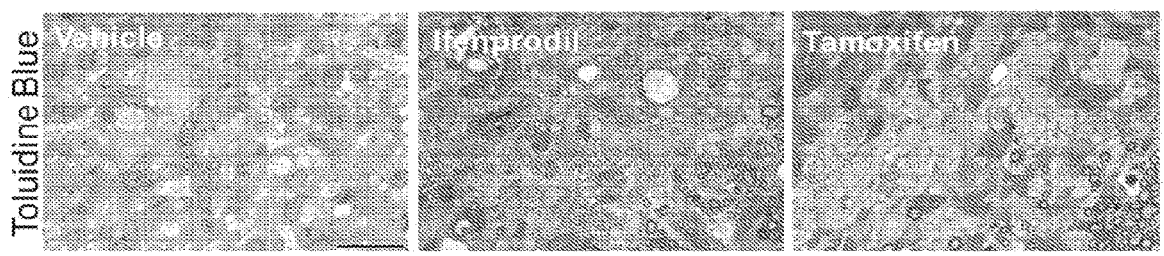
FIGS. 4(A-D) illustrate graphs and images showing the effect of small molecules on sterol intermediate accumulation and enhancement of remyelination in vivo. A) GC/NIS-based quantitation of sterol levels in mouse brain following daily dosing with miconazole (10 mg per kg), ifenprodil (10 mg per kg), and tamoxifen (2 mg per kg) for three days. n=4 animals per group. B) Quantitation of remyelinated axons within toluidine blue stained sections of LPC-lesioned spinal cord from mice treated 8 days with molecules at the doses stated in panel a. n=6 animals per group except vehicle, n=4. Data are presented as mean+/−S.E.M. C) Representative images of toluidine blue stained sections of LPC-lesioned dorsal spinal cord from mice treated 8 days with molecules at doses stated in panel a. Scale bar, 20 μm. D) Representative electron microscopy images of sections of LPC-lesioned dorsal spinal cord from mice treated 8 days with molecules at doses stated in panel a. Scale bar, 5 μm.
Figure 4D:
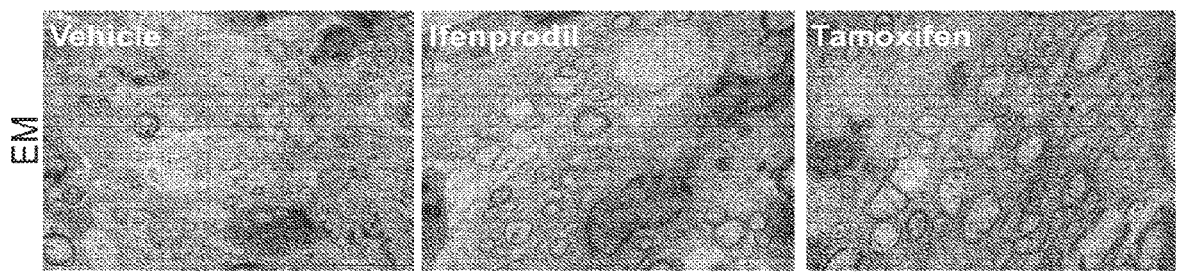

Previously we demonstrated the positive effects of miconazole on remyelination using a well-established mouse model where injection of lysolecithin is used to create focal lesions of demyelination in the dorsal column white matter of the adult spinal cord. To test whether accumulation of other 8,9-unsaturated sterols enhances remyelination in vivo, we treated lesioned mice with ifenprodil (10 mg per kg) or tamoxifen (2 mg per kg) by daily intraperitoneal injection. Treatment began 4 days after lesion, and the effects on remyelination were quantified histologically 8 days later (FIG. 4B). In vehicle treated animals, profiles of sparsely distributed remyelinating axons characterized by thin myelin sheaths were detected mainly at the periphery of the lesion (FIG. 4C), while ultrastructural analyses revealed unmyelinated axons or axons with a single wrap of myelin (FIG. 4D). By contrast, following 8 days of treatment with ifenprodil or tamoxifen, remyelination was widespread throughout the lesion (FIG. 4C). In both central and peripheral regions of the lesion the majority of axons were surrounded by thin myelin sheaths (FIG. 4D). No obvious differences in axonal diameter were apparent between unmyelinated and myelinated axons, and both small diameter and larger diameter axons appeared equally myelinated in both treatments. Collectively, these data show that small molecule inhibitors of CYP51, sterol 14-reductase, and EBP can significantly enhance remyelination in mice.

Figure 13B:
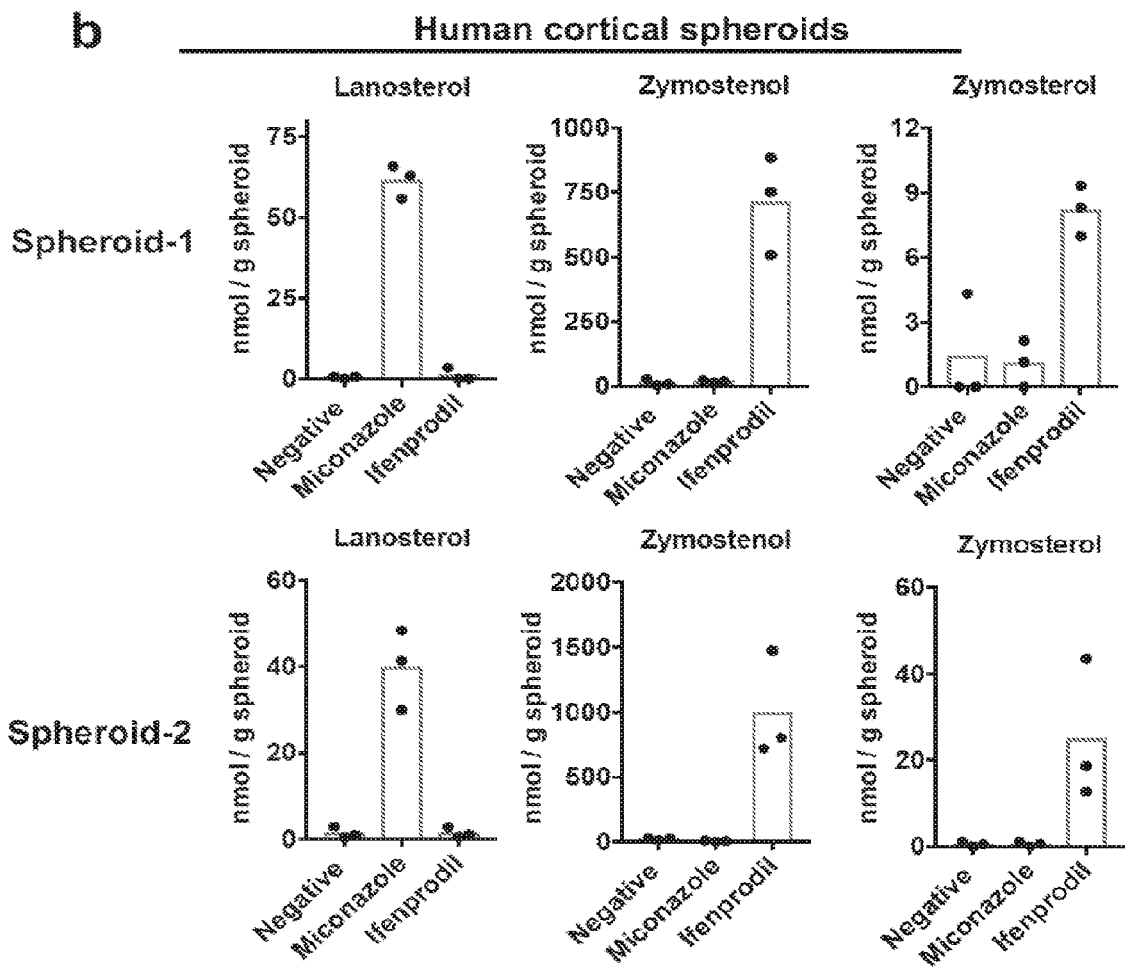

Finally, we also established that the sterol-modulating activities of miconazole, ifenprodil, and tamoxifen are not limited to murine cells but extend to human cells and tissue. We performed sterol profiling in a human glioma cell line and established that these molecules caused accumulation of the expected sterol intermediates (FIG. 13A). Likewise, miconazole and ifenprodil led to 8,9-unsaturated sterol accumulation within human induced pluripotent stem cell-derived cortical spheroids, further confirming that these molecules similarly engage the sterol synthesis pathway in mouse and human cells and CNS tissue (FIG. 13B).

Although multiple groups have identified small-molecule enhancers of oligodendrocyte formation, a key hurdle to clinical translation of these findings to patients with diseases of white matter is the incomplete understanding of these molecules' functional targets in OPCs. Here we define a dominant mechanism shared by many small molecule enhancers of remyelination: elevation of sterol intermediate levels by inhibition of a narrow window of cholesterol biosynthesis enzymes spanning CYP51 to EBP. In all we have characterized twenty-four small molecules with wide-ranging canonical targets as both enhancing myelination and elevating sterol intermediate levels (FIG. 14). No molecules have yet been identified that inhibit steps between CYP51 and EBP but are ineffective at enhancing oligodendrocyte formation. Several of these molecules have previously been shown to elevate 8,9-unsaturated sterol levels in mouse CNS cells and in human patients. Supplying OPCs with 8,9-unsaturated sterols was sufficient to enhance the formation of oligodendrocytes, whereas depleting cholesterol levels was ineffective, suggesting that sterol intermediate accumulation plays a positive role in facilitating oligodendrocyte formation from OPCs. Notably, accumulation of 8,9-unsaturated sterol intermediates has been observed in other cell state transitions, and altering the sterol composition of membranes can perturb membrane structure and signaling. Moreover, other labs have independently shown that multiple molecules annotated here as enhancing sterol intermediate levels have reversed paralysis in mice with MS-like disease, suggesting that altering sterol levels in vivo can regenerate functional myelin. Ultimately, our work demonstrates that modulating the sterol landscape in OPCs can enhance the formation of oligodendrocytes and points to new therapeutic targets, potent inhibitors for these targets, and metabolite-based biomarkers to accelerate the development of optimal remyelinating therapeutics.

It should be understood that the methods described herein may be carried out in a number of ways and with various modifications and permutations thereof that are well known in the art. It may also be appreciated that any theories set forth as to modes of action should not be construed as limiting this invention in any manner, but are presented such that the methods of the invention can be more fully understood.

All publications and patents mentioned in the above specification are herein incorporated by reference.

Having described the invention, the following is claimed:

1. A method of treating multiple sclerosis (MS), amylotrophic lateral sclerosis (ALS), Alzheimer's disease, Huntington's disease, or Parkinson's disease in a subject wherein myelination or remyelination is beneficial to the subject, the method comprising administering to the subject a therapeutically effective amount of an agent that inhibits expression of an enzyme that synthesizes one or more sterol intermediates of the cholesterol biosynthesis pathway in oligodendrocyte progenitor cells (OPCs), wherein the agent:
   (1) comprises an interfering RNA targeting said enzyme, or an antisense oligonucleotide targeting said enzyme, or
   (2) a polynucleotide encoding said interfering RNA, or said antisense oligonucleotide;
   wherein said enzyme functions in the cholesterol biosynthesis pathway spanning CYP51 and emopamil binding protein (EBP).

2. The method of claim 1, wherein myelination is promoted in a subject's CNS demyelinated lesion related to the myelin related disorder.

3. The method of claim 1, wherein the agent comprises said antisense oligonucleotide targeting said enzyme, or said polynucleotide encoding said antisense oligonucleotide targeting said enzyme.

4. The method of claim 1, wherein said enzyme is CYP51, sterol 14-reductase, or emopamil binding protein (EBP).

5. The method of claim 1, wherein said enzyme is emopamil binding protein (EBP).

6. The method of claim 5, wherein the agent comprises said antisense oligonucleotide targeting EBP.

7. The method of claim 5, wherein the agent comprises said polynucleotide encoding said antisense oligonucleotide targeting EBP.

8. The method of claim 1, wherein said enzyme is CYP51.

9. The method of claim 8, wherein the agent comprises said antisense oligonucleotide targeting CYP51.

10. The method of claim 8, wherein the agent comprises said polynucleotide encoding said antisense oligonucleotide targeting CYP51.

* * * * *